United States Patent [19]

Bender et al.

[11] Patent Number: 4,818,748
[45] Date of Patent: Apr. 4, 1989

[54] RENIN INHIBITORS AND AMINOACID AND AMINOALDEHYDE DERIVATIVES

[75] Inventors: Wolfgang Bender; Rolf Henning, both of Wuppertal; Andreas Knorr, Erkrath; Johannes-Peter Stasch, Wuppertal, all of Fed. Rep. of Germany

[73] Assignee: Bayer Aktiengesellschaft, Leverkusen, Fed. Rep. of Germany

[21] Appl. No.: 22,710

[22] Filed: Mar. 6, 1987

[30] Foreign Application Priority Data

Mar. 12, 1986 [DE]  Fed. Rep. of Germany ....... 3608209
Aug. 23, 1986 [DE]  Fed. Rep. of Germany ....... 3628650

[51] Int. Cl.⁴ .................. A61K 37/02; C07K 7/06; C07K 5/08; C07K 5/10
[52] U.S. Cl. ......................... 514/16; 514/17; 514/18; 514/19; 530/328; 530/329; 530/330; 530/331
[58] Field of Search ............... 530/328, 331, 329, 330; 514/18, 16, 17, 19

[56] References Cited

U.S. PATENT DOCUMENTS 4,661,473  4/1987  Boger et al. ............... 514/16
4,668,663  5/1987  Boger ........................ 514/15
4,668,770  5/1987  Boger et al. ............... 530/331

FOREIGN PATENT DOCUMENTS 0104041  3/1984  European Pat. Off. .

OTHER PUBLICATIONS

Matsueda et al., Chemistry Letters, pp. 1041–1044, 1985.
M. Szelke, B. Leckie, A. Hallet, D. M. Jones, J. Sueiras, B. Atrash, Y. A. F. Lever, Potent New Inhibitors Human Renin, Nature, vol. 299, pp. 555–557, Oct. 7, 1982.

Primary Examiner—Delbert R. Phillips
Attorney, Agent, or Firm—Sprung Horn Kramer & Woods

[57] ABSTRACT

Anti-hypertensive compounds of the formula

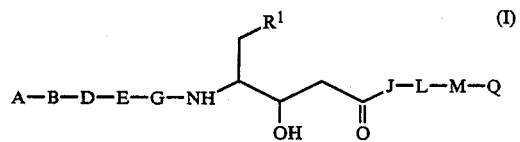

in which
A represents hydrogen, $C_1$–$C_8$-alkyl, $C_7$–$C_{14}$-aralkyl, phenylsulphonyl, tolylsulphonyl or $C_1$–$C_8$-alkylsulphonyl, or represents an aminoprotective group,
B represents a direct bond, or represents sarcosyl, or represents a group of the formula

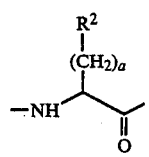

D represents a direct bond, or represents a group of the formula

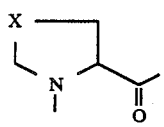

wherein
X represents methylene, ethylene or sulphur,
E, G, J, K, L and M independently have the same meanings as B,
$R^1$ is an optionally substituted phenyl radical, and
Q is a hydroxy, alkoxy or amino group, or a physiologically acceptable salt thereof.

14 Claims, No Drawings

RENIN INHIBITORS AND AMINOACID AND AMINOALDEHYDE DERIVATIVES

The invention relates to renin-inhibitory peptides, processes for their preparation and their use in medicaments, in particular in medicaments which influence the circulation, and to aminoacid derivatives and aminoaldehyde derivatives.

Renin is a proteolytic enzyme which is chiefly produced by the kidneys and secreted into the plasma. It is known that renin splits off the decapeptide angiotensin I from angiotensinogen in vivo. Angiotensin I is in turn degraded in the lung, the kidneys or other tissues to give the octapeptide angiotensin II, which has an effect on blood pressure. The various effects of angiotension II, such as vasoconstriction, Na+ retention in the kidney, release of aldosterone in the adrenal gland and increase in the tonus of the sympathetic nervous system, act synergistically in the context of an increase in blood pressure.

For this reason, the renin-angiotensin system plays an important role in regulation of cardiovascular homoeostasis and in certain forms of hypertension.

The activity of the renin-angiotension system can be manipulated pharmacologically by inhibiting the activity of renin or angiotensin conversion enzyme (ACE) and by blocking angiotensin II receptors. The development of ACE inhibitors which can be used orally has thus led to new antihypertensives.

A more recent use is to intervene in the renin-angiotensin cascade at an earlier point in time, in particular by inhibition of the highly specific peptidase renin.

Various types of renin inhibitors have so far been developed: renin-specific antibodies, phospholipids, peptides with the N-terminal sequence of prorenin, synthetic peptides as substrate analogues and modified peptides.

The most potent renin inhibitors known to date belong to the last two groups mentioned. However, they have a number of disadvantages, thus, for example, poor water-solubility, low bioavailability, a short duration of action on parenteral administration or only a weak activity, if at all, on oral administration.

The present invention relates to peptides containing up to 8 aminoacid groupings of the general formula (I)

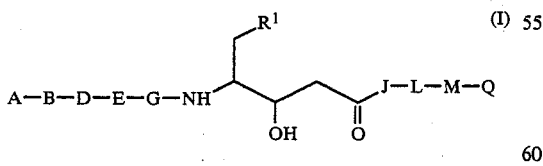

in which

A represents hydrogen, $C_1$-$C_8$-alkyl, $C_7$-$C_{14}$-aralkyl, phenylsulphonyl, tolylsulphonyl or $C_1$-$C_8$-alkylsulphonyl, or represents an amino-protective group, B represents a direct bond, or represents sarcosyl, or represents a group of the formula

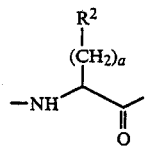

wherein a denotes the number 0, 1, 2, 3 or 4 and
$R^2$ denotes hydrogen, $C_1$-$C_6$-alkyl, hydroxy-$C_1$-$C_2$-alkyl, a group of the formula —$CH_2$—CO—$NHR^3$ or —$CH_2$—NH—$R^3$, wherein $R^3$ represents hydrogen, $C_1$-$C_6$-alkyl, $C_7$-$C_{14}$-aralkyl, tolylsulphonyl, phenylsulphonyl or $C_1$-$C_6$-alkylsulphonyl, or represents an amino-protecting group, or $R^2$ denotes guanidinomethyl, mercaptomethyl, methylthiomethyl, carboxymethyl, $C_1$-$C_6$-alkoxycarbonylmethyl, $C_7$-$C_{14}$-aralkoxycarbonylmethyl, halogen, indolylmethyl, 4-imidazolylmethyl, pyridyl, triazolylmethyl, pyrazolylmethyl or aryl, which can be mono-, di- or trisubstituted by identical or different substituents from the group comprising $C_1$-$C_4$-alkyl, $C_1$-$C_4$-alkoxy, trifluoromethyl, halogen, hydroxyl, nitro and a group of the formula

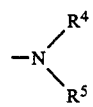

wherein $R^4$ and $R^5$ are identical or different and represent hydrogen, $C_1$-$C_6$-alkyl, aryl, aralkyl, phenylsulphonyl, tolylsulphonyl, $C_1$-$C_6$-alkylsulphonyl, acetyl or benzoyl, or represent an amino-protective group, D represents a direct bond, or represents a group of the formula

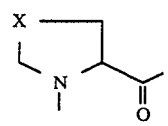

wherein

X represents methylene, ethylene or sulphur,
E has the same meaning as B and is identical to or different from this radical,
G has the same meaning as B and is identical to or different from this radical,
$R^1$ represents a group of the formula

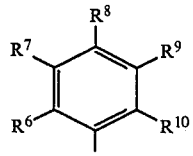

wherein $R^6$, $R^7$, $R^8$, $R^9$ and $R^{10}$ are identical or different and represent hydrogen, $C_1$-$C_6$-alkyl, $C_1$-$C_6$-alkoxy, aryl, halogen, hydroxyl, cyano, trifluoromethyl, trifluoromethoxy, trifluoromethylthio or nitro, or represent a group of the formula

wherein
$R^{11}$ and $R^{12}$ have the same meaning as $R^4$ and $R^5$ and are identical to or different from these radicals,
with the proviso that at least one of the substituents $R^6$, $R^7$, $R^8$, $R^9$ or $R^{10}$ must represent nitro or the group $-NR^{11}R^{12}$,
J, L and M are in each case identical or different and have the same meaning as B and are identical to or different from this radical, and
Q represents a radical of the formula $-OR^{13}$, $-NHR^{14}$, $-NR^{14}R^{15}$ or $-NH-NHR^3$,
wherein
$R^{13}$ represents hydrogen, or represents $C_1-C_{20}$-alkyl, which is optionally interrupted in the chain by an oxygen atom and which can be substituted by halogen, hydroxyl, phenyl or pyridyl,
$R^{14}$ represents hydrogen or $C_1-C_{10}$-alkyl, which can be substituted by aryl, it being possible for this aryl radical in turn to carry substituents from the series comprising nitro, $C_1-C_4$-alkyl, $C_1-C_4$-alkoxy, halogen or cyano, or by halogen, adamantyl, quinuclidine, piperidine, N-methylpiperazine, N-phenylpiperazine, N-benzylpiperazine, pyridyl or morpholine, or represents aryl, which can be mono-, di- or trisubstituted by identical or different substituents from the group comprising nitro, halogen, $C_1-C_4$-alkoxy and $C_1-C_4$-alkyl, it being possible for alkyl in turn to carry substituents from the series comprising hydroxyl, amino, carboxyl and/or $C_1-C_4$-alkoxycarbonyl, or represents adamantyl or quinuclidine, and
$R^{15}$ represents $C_1-C_6$-alkyl, or
$R^{14}$ and $R^{15}$ together form a 5- to 7-membered ring which can contain, as a further hetero atom, an oxygen atom, a sulphur atom or the group $-NH$, $-N-C_1-C_6$-alkyl, $-N$-dimethylamino-$C_1-C_4$-alkyl, $-N$-aryl or $-N$-aralkyl, or which can be substituted by $C_1-C_4$-alkyl or aralkyl, and
$R^3$ has the meaning given,
and physiologically acceptable salts thereof.

In the context of the present invention, aryl represents an aromatic hydrocarbon radical with 6 to 14 carbon atoms. Aryl preferably represents phenyl or naphthyl.

In the context of the invention, alkyl represents straight-chain or branched alkyl groups with in each case the stated number of carbon atoms. Alkyl also includes cycloalkyl, cycloalkylalkyl or alkylcycloalkyl.

In the context of the invention, aralkyl represents an aromatic hydrocarbon radical with has 6 to 14 carbon atoms and is bonded via an alkyl chain with 1 to 6 carbon atoms. Aralkyl preferably represents benzyl, phenethyl or naphthylmethyl.

In the context of the invention, an amino-protective group represents the customary amino-protective groups used in peptide chemistry.

These include, preferably: benzyloxycarbonyl, 4-bromobenzyloxycarbonyl, 2-chlorobenzyloxycarbonyl, 3-chlorobenzyloxycarbonyl, dichlorobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 4-nitrobenzyloxycarbonyl, 2-nitrobenzyloxycarbonyl, 2-nitro-4,5-dimethoxybenzyloxycarbonyl, 3,4,5-trimethoxybenzyloxycarbonyl, methoxycarbonyl, ethoxycarbonyl, propoxycarbonyl, isopropoxycarbonyl, butoxycarbonyl, isobutoxycarbonyl, tert-butoxycarbonyl, pentoxycarbonyl, isopentoxycarbonyl, hexoxycarbonyl, cyclohexoxycarbonyl, octoxycarbonyl, 2-ethylhexoxycarbonyl, 2-iodohexoxycarbonyl, 2-bromoethoxycarbonyl, 2-chloroethoxycarbonyl, 2,2,2-trichloroethoxycarbonyl, 2,2,2-trichloro-tert-butoxycarbonyl, benzhydryloxycarbonyl, bis-(4-methoxyphenyl)methoxycarbonyl, phenacyloxycarbonyl, 2-trimethylsilylethoxycarbonyl, 2-(di-n-butyl-methylsilyl)ethoxycarbonyl, 2-triphenylsilylethoxycarbonyl, 2-(dimethyl-tert-butylsilyl)ethoxycarbonyl, menthyloxycarbonyl, vinyloxycarbonyl, allyloxycarbonyl, phenoxycarbonyl, tolyloxycarbonyl, 2,4-dinitrophenoxycarbonyl, 4-nitrophenoxycarbonyl, 2,4,5-trichlorophenoxycarbonyl, naphthyloxycarbonyl, fluorenyl-9-methoxycarbonyl, valeroyl, isovaleroyl, butyryl, ethylthiocarbonyl, methylthiocarbonyl, butylthiocarbonyl, tert-butylthiocarbonyl, phenylthiocarbonyl, benzylthiocarbonyl, methylaminocarbonyl, ethylaminocarbonyl, propylaminocarbonyl, isopropylaminocarbonyl, formyl, acetyl, propionyl, pivaloyl, 2-chloroacetyl, 2-bromoacetyl, 2-iodoacetyl, 2,2,2-trifluoroacetyl, 2,2,2-trichloroacetyl, benzoyl, 4-chlorobenzoyl, 4-methoxybenzoyl, 4-nitrobenzyl, 4-nitrobenzoyl, naphthylcarbonyl, phenoxyacetyl, adamantylcarbonyl, dicyclohexylphosphoryl, diphenylphosphoryl, dibenzylphosphoryl, di-(4-nitrobenzyl)-phosphoryl, phenoxyphenylphosphoryl, diethylphosphinyl, diphenylphosphinyl, phthaloyl or phthalimido.

Particularly preferred amino-protective groups are benzyloxycarbonyl, 3,4-dimethoxybenzyloxycarbonyl, 3,5-dimethoxybenzyloxycarbonyl, 4-methoxybenzyloxycarbonyl, 4-nitrobenzyloxycarbonyl, 2-nitrobenzyloxycarbonyl, 3,4,5-trimethoxybenzyloxycarbonyl, methoxycarbonyl, ethoxycarbonyl, propoxycarbonyl, isopropoxycarbonyl, butoxycarbonyl, isobutoxycarbonyl, tert-butoxycarbonyl, cyclohexoxycarbonyl, hexoxycarbonyl, octoxycarbonyl, 2-bromoethoxycarbonyl, 2-chloroethoxycarbonyl, phenoxyacetyl, naphthylcarbonyl, adamatylcarbonyl, phthaloyl, 2,2,2-trichloroethoxycarbonyl, 2,2,2-trichloro-tert-butoxycarbonyl, menthyloxycarbonyl, vinyloxycarbonyl, allyloxycarbonyl, phenoxycarbonyl, 4-nitrophenoxycarbonyl, fluorenyl-9-methoxycarbonyl, formyl, acetyl, propionyl, pivaloyl, 2-chloroacetyl, 2-bromoacetyl, 2,2,2-trifluoroacetyl, 2,2,2-trichloroacetyl, benzoyl, 4-chlorobenzoyl, 4-bromobenzoyl, 4-nitrobenzoyl, phthalimido or isovaleroyl.

The compounds of the general formula (I) according to the invention have several asymmetric carbon atoms. They can be in the D- or L-form, independently of one another. The invention includes the optical antipodes as well as the isomer mixtures or racemates.

Preferably, the groups B, D, E, G, J, L and M are independently of one another in the optically pure form, preferably the L-form.

The grouping of the formula

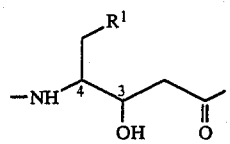

has 2 asymmetric carbon atoms which, independently of one another, can be in the R- or S-configuration. This grouping is preferably in the 3S,4S-configuration, 3R,4S-configuration or 3S,4R- or 3R,4R-configuration, particularly preferably in the 3S,4S- or 3R,4S-configuration. The grouping is also used as an isomer mixture of the 3RS-4S configuration.

The compounds of the general formula (I) according to the invention can exist in the form of their salts. These can be salts of the compounds according to the invention with inorganic or organic acids or bases. The acid addition products include, preferably, salts with hydrochloric acid, hydrobromic acid, hydroiodic acid, sulphuric acid or phosphoric acid, or with carboxylic acids, such as acetic acid, propionic acid, oxalic acid, glycolic acid, succinic acid, maleic acid, hydroxymaleic acid, methylmaleic acid, fumaric acid, adipic acid, malic acid, tartaric acid, citric acid, benzoic acid, cinnamic acid, lactic acid, ascorbic acid, salicylic acid, 2-acetoxybenzoic acid, nicotinic acid or isonicotinic acid, or sulphonic acids, such as methanesulphonic acid, ethanesulphonic acid, benzenesulphonic acid, toluenesulphonic acid, naphthalene-2-sulphonic acid or naphthalenedisulphonic acid.

Preferred compounds of the general formula (I) are those in which

A represents hydrogen, $C_1$-$C_4$-alkyl, benzyl, phenylsulphonyl, tolylsulphonyl or $C_1$-$C_4$-alkylsulphonyl, or represents an amino-protective group, B represents a direct bond or a radical of the formula

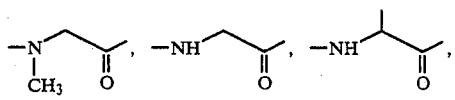

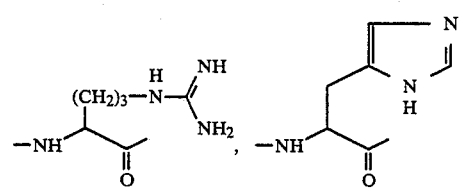

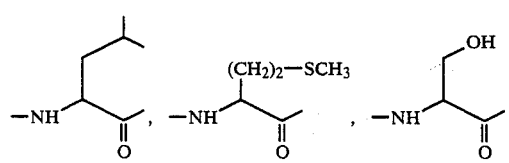

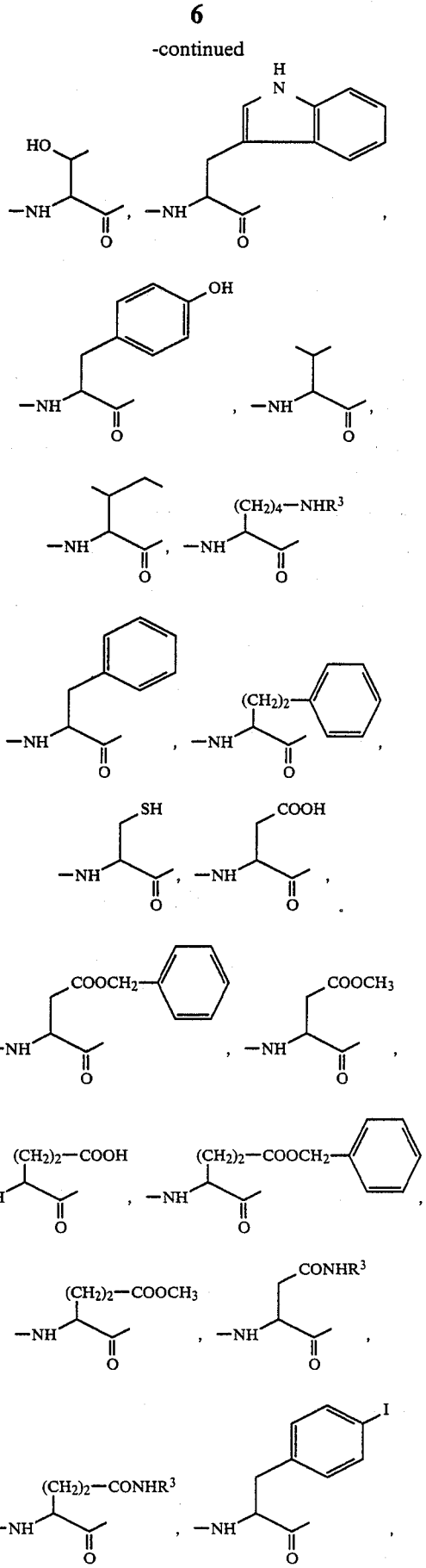

-continued

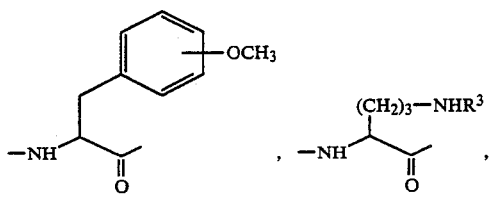
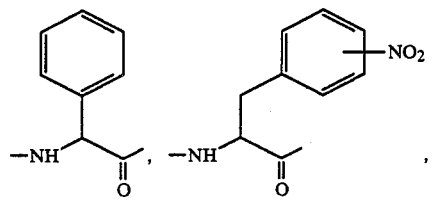
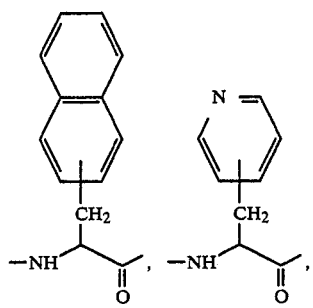
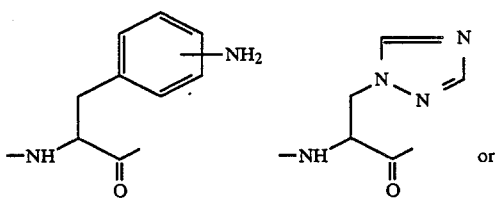
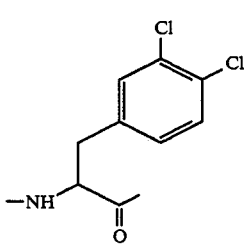

in its D-form, L-form or as a D,L-isomer mixture, preferably in the L-form, wherein $R^3$ represents hydrogen, $C_1$-$C_4$-alkyl, benzyl, phenylsulphonyl, tolylsulphonyl or $C_1$-$C_4$-alkylsulphonyl, or represents an amino-protective group, D represents a direct bond, or represents the group of the formula

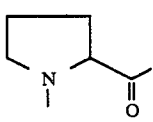

in its L-form, D-form or as a D,L-isomer mixture,

E and G in each case are identical or different and have the same meaning as B and are identical to or different from this radical, $R^1$ represents a group of the formula

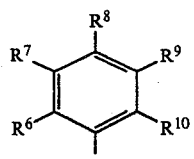

wherein $R^6$, $R^7$, $R^8$, $R^9$ and $R^{10}$ are identical or different and represent hydrogen, methyl, methoxy, fluorine, chlorine, bromine, iodine, hydroxyl, cyano, trifluoromethyl or nitro, or represent a group of the formula

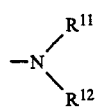

wherein $R^{11}$ and $R^{12}$ are identical or different and represent hydrogen, $C_1$-$C_4$-alkyl, phenyl, benzyl, phenylsulphonyl, tosyl, $C_1$-$C_4$-alkylsulphonyl or acetyl, or represent an amino-protective group, with the proviso that at least one of the substituents $R^6$, $R^7$, $R^8$, $R^9$ or $R^{10}$ must represent nitro or represent the group $-NR^{11}R^{12}$, J, L and M are in each case identical or different and have the same meaning as B and can be identical to or different from this radical, and Q represents a radical of the formula $-OR^{13}$, $-N-H-NHR^3$, $-NHR^{14}$ or

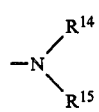

wherein $R^{13}$ represents hydrogen or $C_1$-$C_{18}$-alkyl, which can be substituted by chlorine, bromine, hydroxyl or phenyl, $R^{14}$ represents hydrogen or $C_1$-$C_4$-alkyl, which can be substituted by phenyl which is optionally substituted by nitro, methyl or methoxy, or by fluorine, chlorine, bromine, pyridyl, adamantyl, quinuclidine, piperidine, N-methyl-, N-phenyl- or N-benzylpiperazine or benzylcyclohexyl, or represents phenyl, which is optionally substituted by nitro, fluorine, chlorine or methoxy or by $C_1$-$C_4$-alkyl which is optionally substituted by hydroxyl, amino, carboxyl and/or $C_1$-$C_4$-alkoxycarbonyl, or represents adamantyl or quinuclidine and $R^{15}$ represents $C_1$-$C_4$-alkyl, or $R^{14}$ and $R^{15}$ together form a ring from the series comprising pyrrolidine, piperidine, benzylpiperidine, morpholine, piperazine, N-methyl-, N-phenyl, N-benzyl- and —N-dimethylaminoethylpiperazine and $R^3$ has the meaning given, and physiologically acceptable salts thereof.

Particularly preferred compounds of the general formula (I) are those in which

A represents hydrogen, methyl, ethyl or tosyl, or represents an amino-protective group, preferably from the series comprising benzyloxycarbonyl, 4-methoxybenzyloxycarbonyl, 4-nitrobenzyloxycarbonyl, 3,4,5-trimethoxybenzyloxycarbonyl, methoxycarbonyl, ethoxycarbonyl, propoxycarbonyl, butoxycarbonyl, tert.-butoxycarbonyl, 2-bromoethoxycarbonyl, 2-chloroethoxycarbonyl, 2,2,2-trichloroethoxycarbonyl, allyloxycarbonyl, phenoxycarbonyl, 4-nitrophenoxycarbonyl, fluorenyl-9-methoxycarbonyl, acetyl, pivaloyl, isovaleroyl, phthaloyl, 2,2,2-trichloroacetyl, 2,2,2-trifluoroacetyl, benzyl, tosyl, benzoyl, 4-nitrobenzoyl or phthalimido, B represents a direct bond, or sarcosyl (Sar), glycyl (Gly), alanyl (Ala), arginyl (Arg), histidyl (His), leucyl (Leu), isoleucyl (Ile), seryl (Ser), threonyl (Thr), tryptophyl (Trp), tyrosyl (Tyr), valyl (Val), lysyl (Lys), ornityl (Orn), phenylalanyl (Phe), cystyl (Cys), asparagyl (Asp), glutamyl (Glu), asparaginyl (Asn), glutaminyl (Gln), phenylglycyl (Phg), 4-nitrophenylalanyl [Phe(4NO₂)], 3-nitrophenylalanyl [Phe(3NO₂)], 2-nitrophenylalanyl [Phe(2NO₂)], 2-, 3- or 4-aminophenylalanyl [Phe(2NH₂), Phe(3NH₂), Phe(4NH₂)], 3,4-dichlorophenylalanyl [Phe(3,4-Cl₂)], 4-iodophenylalanyl [Phe(4I)], 4-methoxyphenylalanyl [Phe(4OCH₃)], 1-triazolylalanyl [Trz(1)], 2-pyridylalanyl [Pyr(2)], 3-pyridylalanyl [Pyr(3)], 4-pyridylalanyl [Pyr(4)], 1-naphthylalanyl [Nal(1)] or 2-naphthylalanyl [Nal(2)], optionally with protective groups, in their L-form or D-form, but preferably in their L-form, D represents a direct bond, or represents D- or L-prolyl (Pro), E and G are in each case identical or different and have the same meaning as B and are identical to or different from this radical, $R^1$ represents a phenyl radical which carries, in the 2-, 3- or 4-position, a nitro group or an amino group of the formula

wherein $R^{11}$ and $R^{12}$ are identical or different and denote hydrogen, methyl, ethyl or acetyl, or $R^{11}$ represents hydrogen and $R^{12}$ represents an amino-protective group, or represents 2-methyl-3-nitrophenyl, 4-methyl-3-nitrophenyl, 6-methyl-2-nitrophenyl, 3-methyl-4-nitrophenyl or 3,5-dinitrophenyl, J, L and M are in each case identical or different and have the same meaning as B and are identical to or different from this radical and Q represents a radical of the formula $-OR^{13}$, $-NH-NHR^3$, $-NHR^{14}$ or

wherein $R^3$ represents hydrogen, tert-butoxycarbonyl or benzyloxycarbonyl, $R^{13}$ represents hydrogen, benzyl or $C_1-C_6$-alkyl, $R^{14}$ represents hydrogen, $C_1-C_4$-alkyl, benzyl, 1-phenylethyl, 2-phenylethyl, adamantyl, quinuclidyl, pyridylmethyl or 4-benzylcyclohexylmethyl and $R^{15}$ represents $C_1-C_4$-alkyl, or $R^{14}$ and $R^{15}$ together form a ring, such as 4-benzylpiperidino, N-benzyl- or N-phenethylpiperazine or N-dimethylaminoethylpiperazine, and physiologically acceptable salts thereof.

Especially preferred compounds of the general formula (I)

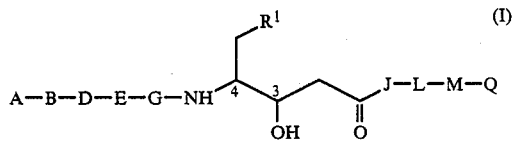

are those in which

A represents hydrogen, tert-butoxycarbonyl, benzyloxycarbonyl, ethoxycarbonyl, acetyl, chloroacetyl, isovaleroyl, benzoyl, tosyl, phenoxycarbonyl, phthaloyl or phthalimido, B represents a direct bond or phenylalanyl (Phe), D represents a direct bond or proline (Pro), E represents a direct bond, or represents tyrosyl (Tyr), phenylalanyl (Phe), 1-naphthylalanyl [Nal(1)], 4-nitrophenylalanyl [Phe(4NO₂)], 3,4-dichlorophenylalanyl [Phe(3,4-Cl₂)], 4-aminophenylalanyl [Phe(4NH₂)], 4-iodophenylalanyl [Phe(4I)], 4-methoxyphenylalanyl [Phe(4OCH₃)] or phenylglycyl (Phg), G represents a direct bond, or represents phenylalanyl (Phe), histidyl (His), 3-pyridylalanyl [Pyr(3)] or 4-aminophenylalanyl [Phe(4NH₂)], the amino group optionally being protected by benzyloxycarbonyl (Z), tert-butoxycarbonyl (Boc) or fluorenyl-9-methoxycarbonyl (Fmoc), or represents 1-triazolylanyl [Trz(1)], preferably in each case in the L-form or as a D,L-mixture, $R^1$ represents 2-, 3- or 4-nitrophenyl or 2-, 3- or 4-aminophenyl, the group

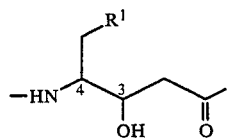

being in the 3S,4S-configuration, 3R,4S-configuration or as a 3RS-4S isomer mixture, J represents a direct bond, or represents leucyl (Leu) or isoleucyl (Ile), preferably in each case in the L-form, L represents a direct bond, or represents phenylalanyl (Phe), histidyl (His) or 4-nitrophenylalanyl [Phe(4NO₂)], preferably in each case in the L-form, M represents a direct bond and Q represents hydroxyl, methoxy, ethoxy, n-propoxy, isopropoxy, tert.-butoxy or benzyloxy, or represents amino, benzylamino, 1-phenylethylamino, 2-phenylethylamino, α-pyridylmethylamino, β-pyridylmethylamino, μ-pyridylmethylamino, 4-benzylcyclohexylmethylamino, 4-benzylpiperidino, 4-benzylpiperazino, N-dimethylaminoethylpiperazino, 1-adamantylamino, 2-adamantylamino or 3-quinuclidineamino, and physiologically acceptable salts thereof.

The following compounds according to the invention, as optical antipodes or isomer mixtures, are to be mentioned in particular:

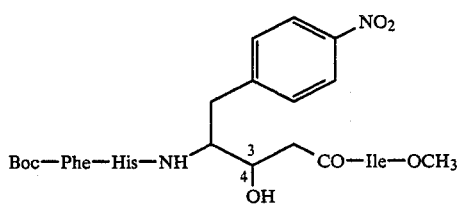
(1)

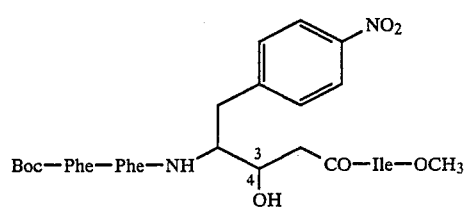
(2)

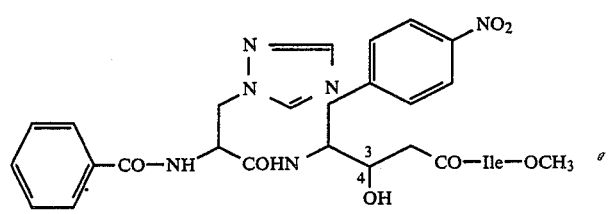
(3)

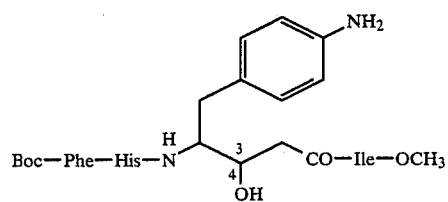
(4)

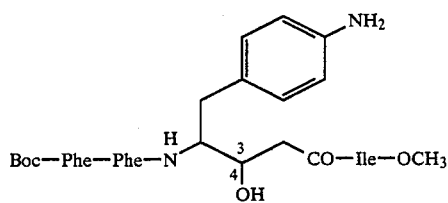
(5)

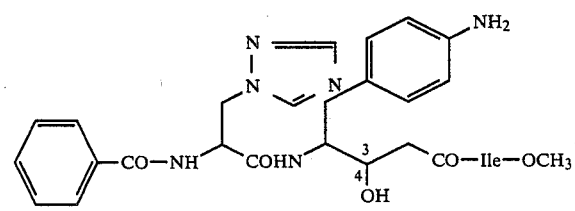
(6)

-continued
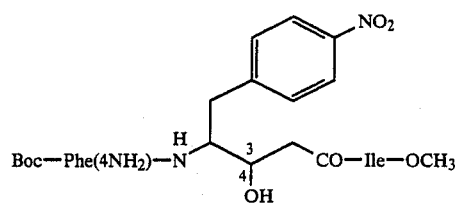
(7)
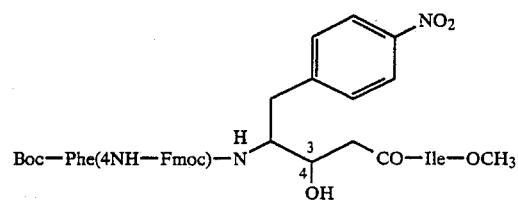
(8)
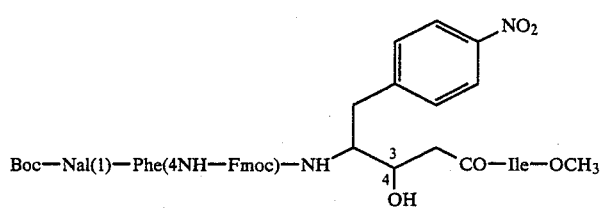
(9)
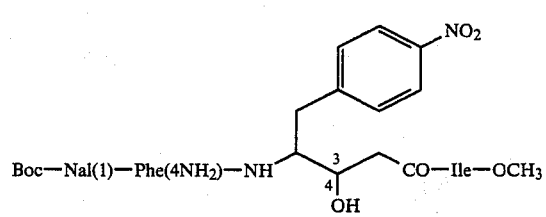
(10)
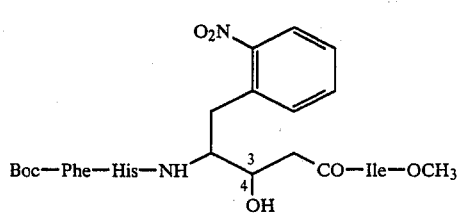
(11)
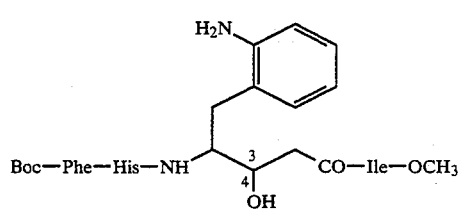
(12)
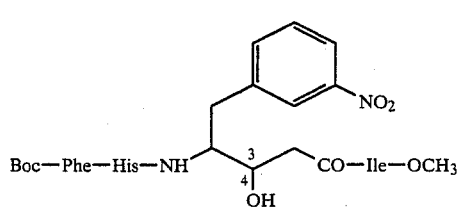
(13)

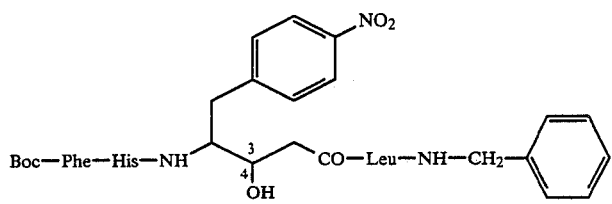
(14)
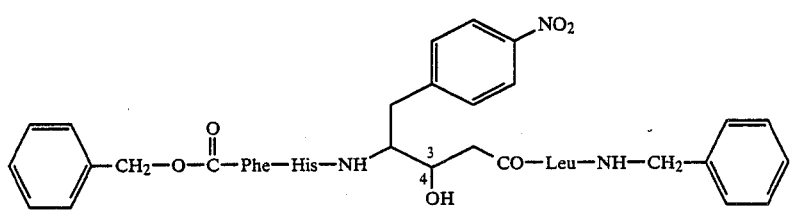
(15)
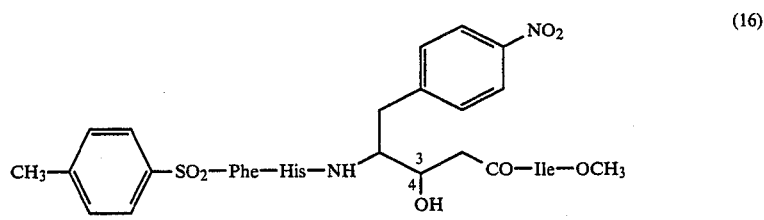
(16)
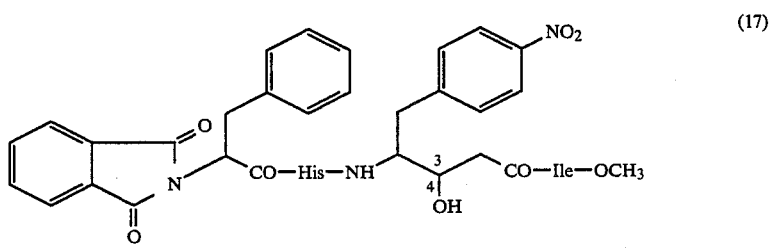
(17)
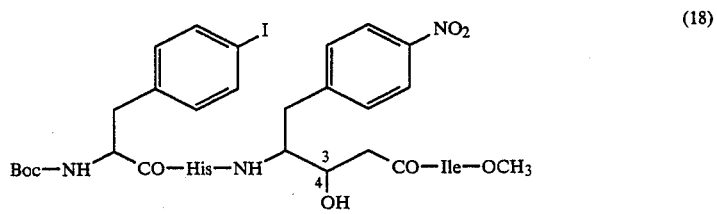
(18)
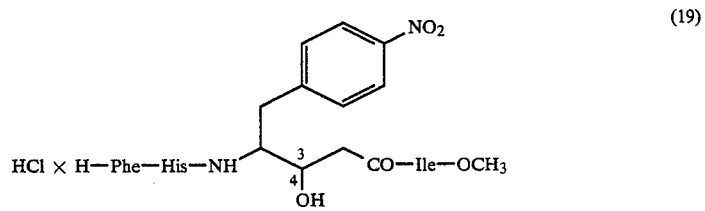
(19)
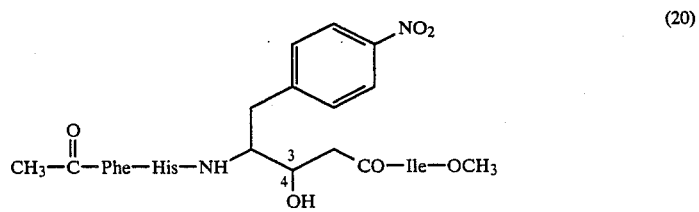
(20)

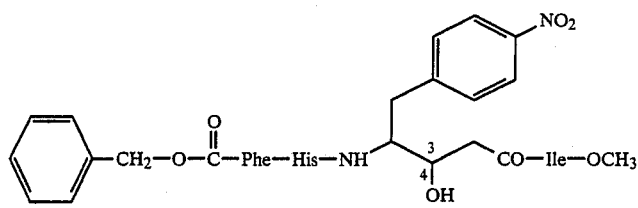
(21)
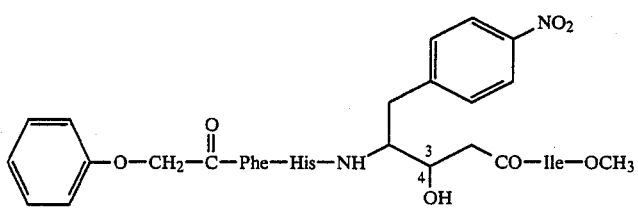
(22)
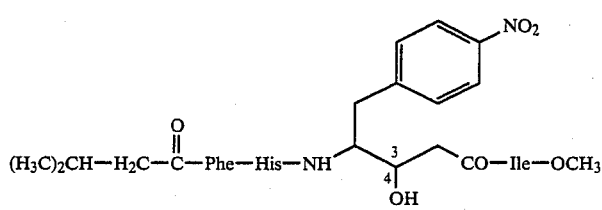
(23)
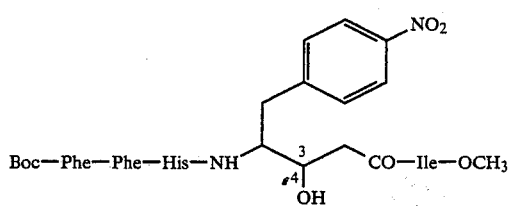
(24)
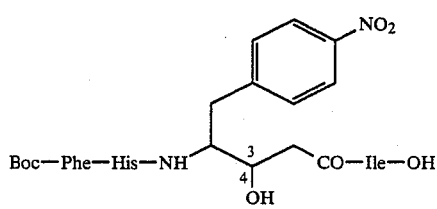
(25)
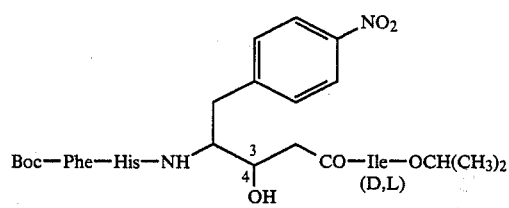
(26)
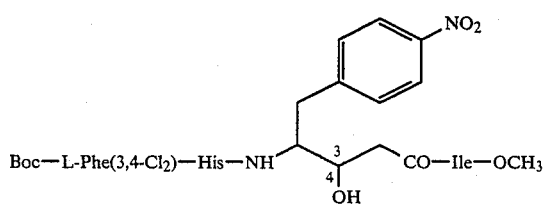
(27)

-continued
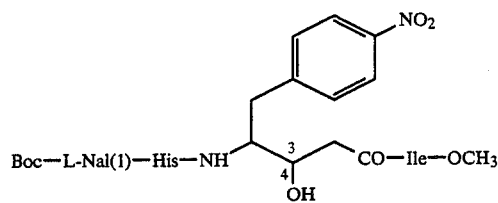 (28)
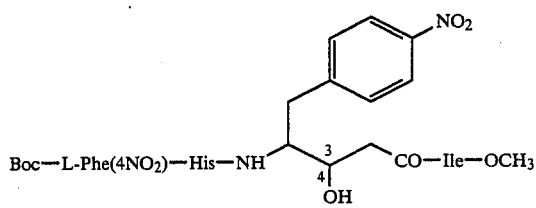 (29)
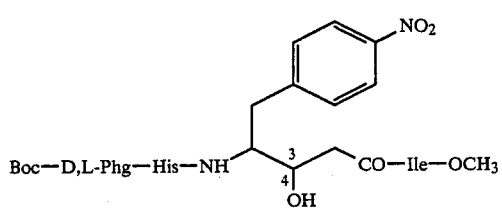 (30)
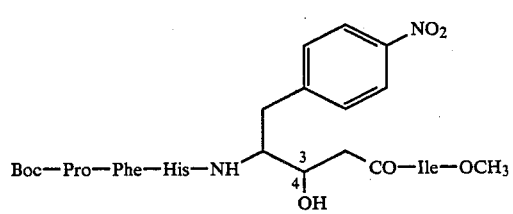 (31)
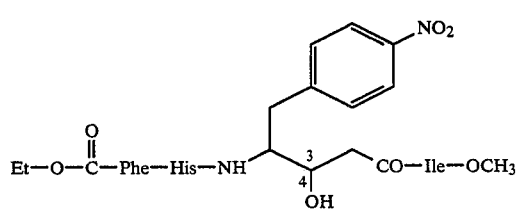 (32)
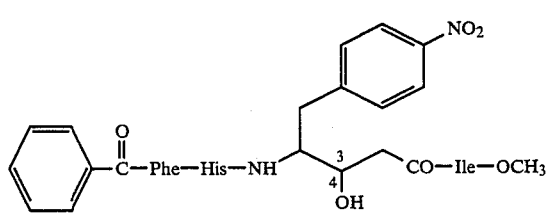 (33)
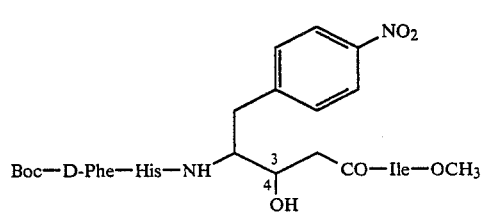 (34)

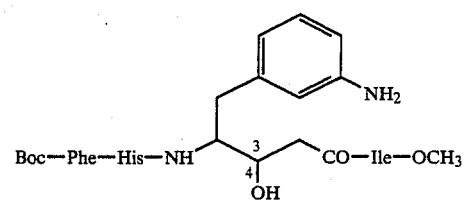
(35)
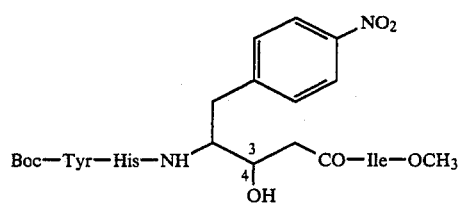
(36)
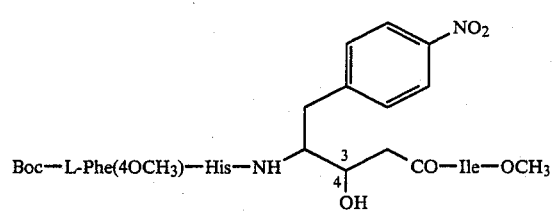
(37)
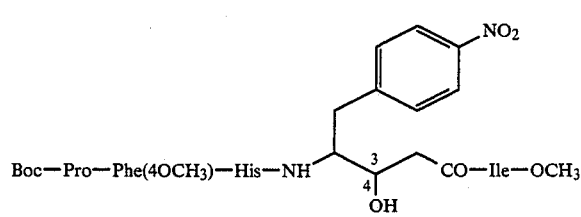
(38)
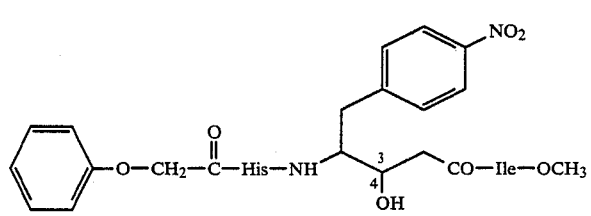
(39)
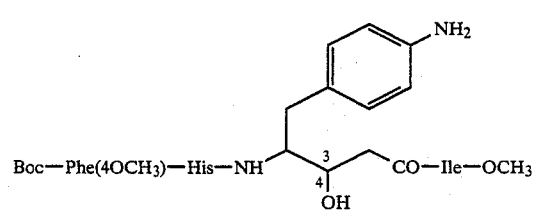
(40)
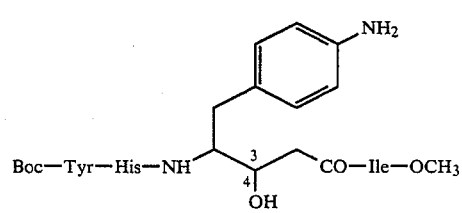
(41)

-continued
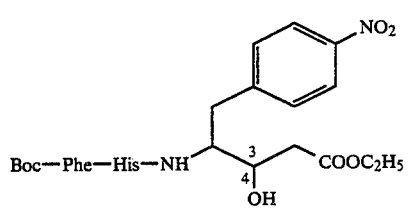 (42)
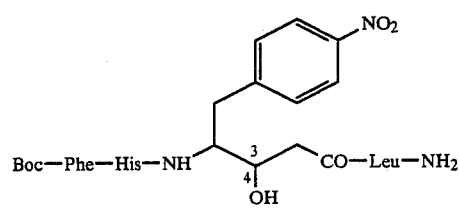 (43)
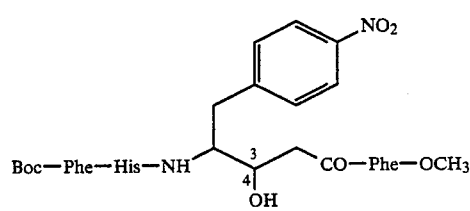 (44)
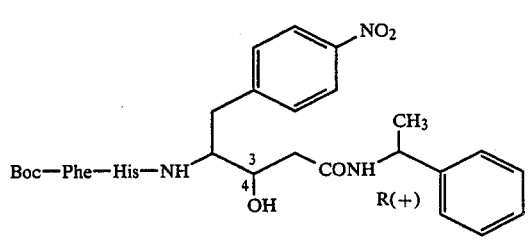 (45)
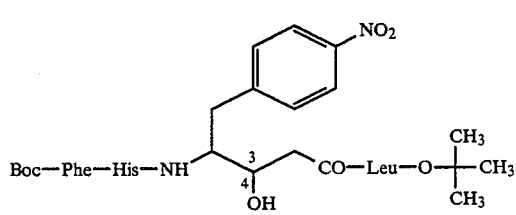 (46)
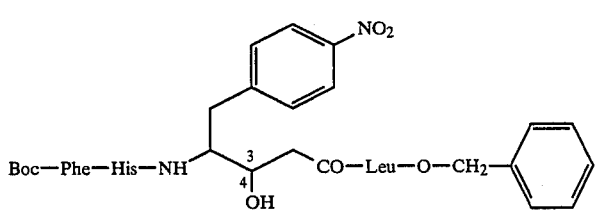 (47)
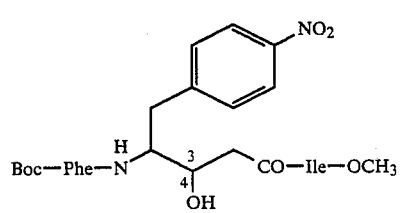 (48)

-continued
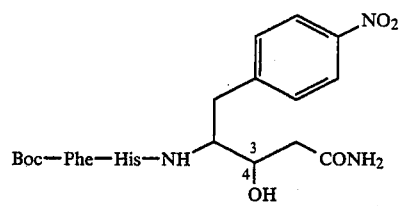
(49)
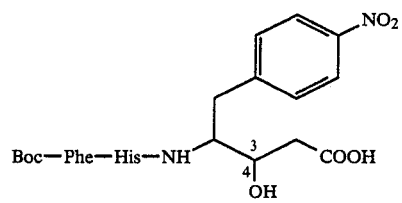
(50)
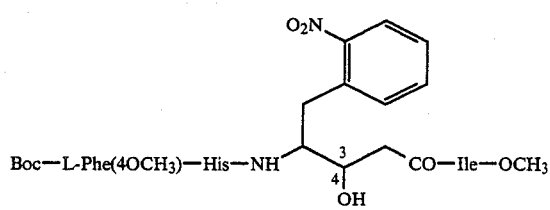
(51)
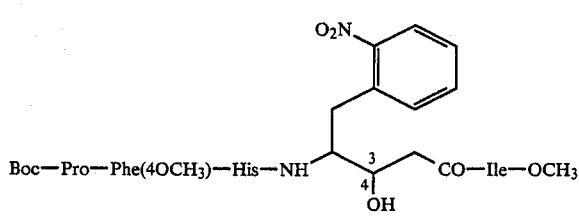
(52)
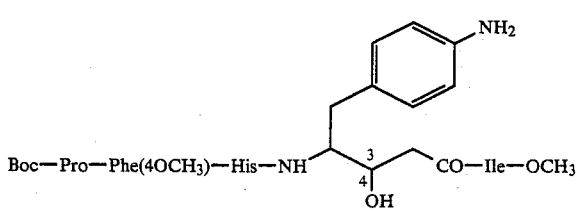
(53)
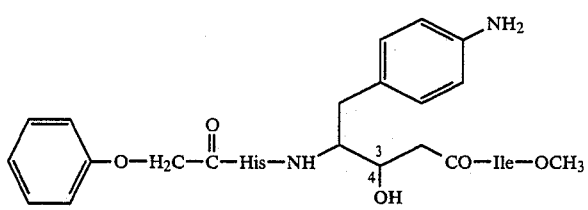
(54)
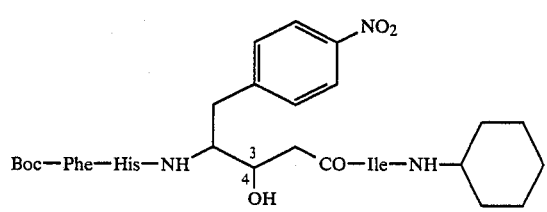
(55)

-continued

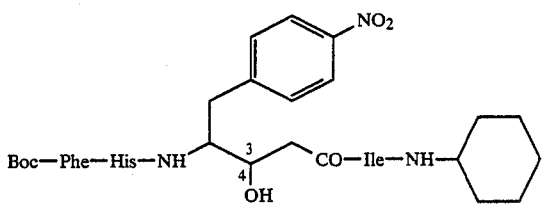

(56)

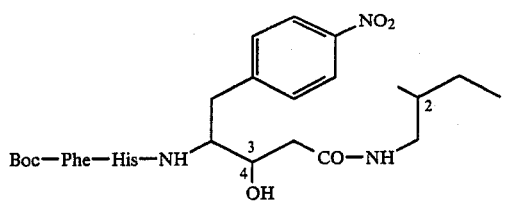

(57)

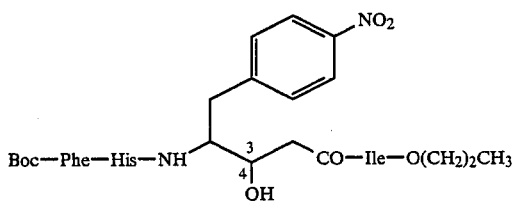

(58)

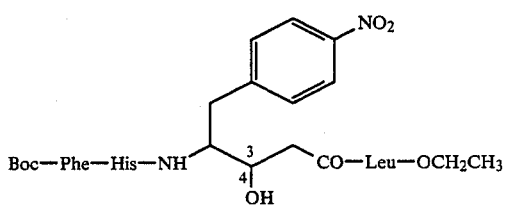

(59)

The invention also relates to a process for the preparation of the peptides of the general formula (I) according to the invention, consisting of one to eight amino acids, characterized in that the peptide bonds of the compounds of the formula (I) are produced by reaction of a corresponding fragment, consisting of one or more amino acid groupings and with a free carboxyl group, optionally present in the activated form, with a complementing fragment, consisting of one or more amino acid groupings and with an amino group, optionally in activated form, and if appropriate repeating this operation with corresponding fragments until the desired peptides of the formula (I) have been prepared, and, if appropriate, subsequently splitting off protective groups or replacing them by other protective groups.

Additional reactive groups, such as, for example, amino or hydroxyl groups, can be protected here in the side chains of the fragments by customary protective groups, if appropriate.

By the process according to the invention, it is possible (a) to build up the peptides according to the invention stepwise and systematically from individual amino acids from the C-terminus (onto which the group Q is linked) to the N-terminus (onto which the group A is linked), or vice versa, or (b) to synthesize corresponding di-, tri- or oligopeptide units separately by the process described and to combine them in one step with units of different size to give the desired compounds of the formula (I).

Activated carboxyl groups here are preferably: carboxylic acid azides (obtainable, for example, by reaction of protected or unprotected carboxylic acid hydrazides with nitrous acids, salts thereof or alkyl nitrites (for example isoamyl nitrite), or unsaturated esters, in particular vinyl esters (obtainable, for example, by reaction of a corresponding ester with vinyl acetate), carbamoyl vinyl esters (obtainable, for example, by reaction of a corresponding acid with an isoxazolium reagent), alkoxyvinyl esters (obtainable, for example, by reaction of the corresponding acids with alkoxyacetylenes, preferably ethoxyacetylene), or amidino esters, for example N,N'- or N,N-disubstituted amidino esters (obtainable, for example, by reaction of the corresponding acid with an N,N'-disubstituted carbodiimide (preferably dicyclohexylcarbodiimide, diisopropylcarbodiimide or N-(3-dimethylaminopropyl)-N'-ethylcarbodiimide hydrochloride) or with an N,N-disubstituted cyanamide), or aryl esters, in particular phenyl esters substituted by electron-withdrawing substituents, for example 4-nitrophenyl, 4-methylsulphonylphenyl, 2,4,5-trichlorophenyl, 2,3,4,5,6-pentachlorophenyl and 4-phenyldiazophenyl esters (obtainable, for example, by reaction of the corresponding acid with a correspondingly substituted phenol, if appropriate in the presence of a condensing agent, such as, for example, N,N'-dicyclohexylcarbodiimide, diisopropylcarbodiimide, N-(3-dimethylaminopropyl)-N'-ethylcarbodiimide hydrochloride, isobutylchloroformate or propanephosphonic acid anhydride, or benzotriazolyloxytris(dimethylamino)phosphonium hexafluorophosphate), or cyanomethyl esters (obtainable, for example, by reaction of the corresponding acid with chloroacetonitrile in the presence of a base), or thioesters, in particular nitrophenyl thioesters (obtainable, for example, by reaction of the corresponding acid with nitrothiophenols, if appropriate in the presence of condensing agents, such as N,N'-dicyclohexylcarbodiimide, diisopropylcarbodiimide, N-(3-dimethylaminopropyl)-N'-ethylcarbodiimide hydrochloride, isobutylchloroformate, propanephosphonic acid anhydride or benzotriazolyloxytris(dimethylamino)phosphonium hexafluorophosphate), or amino or amido esters (obtainable, for example, by reaction of the corresponding acid with an N-hydroxyamino or N-hydroxyamido compound, in particular N-hydroxy-succinimide, N-hydroxypiperidine, N-hydroxy-phthalimide, N-hydroxy-5-norbornene-2,3-dicarboxylic acid imide or 1-hydroxybenzotriazole, if appropriate in the presence of condensing agents, such as N,N'-dicyclohexylcarbodiimide, diisopropylcarbodiimide or N-(3-dimethylaminopropyl)-N'-ethylcarbodiimide hydrochloride, isobutylchloroformate or propanephosphonic acid anhydride), or anhydrides of acids, preferably symmetric or unsymmetric anhydrides of the corresponding acids, in particular anhydrides with inorganic acids (obtainable, for example, by reaction of the corresponding acid with thionyl chloride, phosphorus pentoxide or oxalyl chloride), or anhydrides with carbonic acid half-derivatives, for example carbonic acid lower alkyl half-esters (obtainable, for example, by reaction of the corresponding acid with halogenoformic acid lower alkyl esters, for example methyl, ethyl, propyl, isopropyl, butyl or isobutyl chloroformate, or with 1-lower alkoxycarbonyl-2-lower alkoxy-1,2-dihydro-quinoline, for example 1-methoxycarbonyl-2-ethoxy-1,2-dihydroquinoline), or anhydrides with dihalogenophosphoric acids (obtainable, for example, by reaction of the corresponding acid with phosphorus oxychloride), or anhydrides with phosphoric acid derivatives or phosphorous acid derivatives (for example propanephosphonic acid anhydride, H. Wissmann and H. J. Kleiner, Angew. Chem. Int. Ed. 19, 133 (1980), or anhydrides with organic carboxylic acids (obtainable, for example, by reaction of the corresponding acids with an optionally substituted lower alkane- or phenylalkanecarboxylic acid halide, in particular phenylacetic acid or pivaloyl or trifluoroacetyl chloride), or anhydrides with organic sulphonic acids (obtainable, for example, by reaction of an alkali metal salt of a corresponding acid with a sulphonic acid halide, in particular methane-, ethane-, benzene- or toluenesulphonyl chloride), or symmetric anhydrides (obtainable, for example, by condensation of corresponding acids, if appropriate in the presence of condensing agents, such as N,N'-dicyclohexylcarbodiimide, diisopropylcarbodiimide, N-(3-dimethylaminopropyl)-N'-ethylcarbodiimide hydrochloride, isobutyl chloroformate, propanephosphonic acid anhydride or benzotriazolyloxy-tris(dimethylamino)phosphonium hexafluorophosphate.

Reactive cyclic amides are, in particular, amides with five-membered heterocyclic radicals with 2 nitrogen atoms and optionally aromatic character, preferably amides with imidazoles or pyrazoles (obtainable, for example, by reaction of the corresponding acids with N,N'-carbonyldiimidazole or—if appropriate in the presence of condensing agents, such as, for example, N,N'-dicyclohexylcarbodiimide, N,N'-diisopropylcarbodiimide, N-(3-dimethylaminopropyl)-N'-ethylcarbodiimide hydrochloride, isobutyl chloroformate, propanephosphonic acid anhydride or benzotriazolyloxy-tris(dimethylamino)phosphonium hexafluorophosphate—with, for example, 3,5-dimethylpyrazole, 1,2,4-triazole or tetrazole.

A complementing fragment with a free amino group is ammonia, a primary or secondary amine or an amino acid or a peptide radical which has been prepared by the methods A and B described.

The amino group participating in the reaction in a complementing fragment of a compound according to the invention is preferably in the free form, especially if the carboxyl group reacted with it is employed in activated form. However, it can likewise be activated itself. Such a reactive form is, for example, an isocyanate or a carbamic acid halide.

If the complementing fragment with a free amino group is ammonia or a mono- or disubstituted amine (preferably with linking of the group Q), a corresponding urea can also be a reactive form of this amine.

The process according to the invention is carried out in a manner which is known per se, the reaction conditions being chosen according to the nature of the activation of the carbonyl group. The process is usually carried out in the presence of suitable solvents or diluents, if appropriate in the presence of an auxiliary, in a temperature range from $-80°$ C. to $300°$ C., preferably from $-30°$ C. to $200°$ C., under normal pessure. It is also possible to carry out the process under increased or reduced pressure.

Condensing agents, which can also be bases, are preferably used as auxiliaries, especially if the carboxyl group is present in activated form as an anhydride. The customary condensing agents are preferably employed here, such as carbodiimides, for example N,N'-diethyl-, N,N'-dipropyl-, N,N'-diisopropyl- or N,N'-dicyclohexylcarbodiimide or N-(3-dimethylaminoisopropyl)-N'-ethylcarbodiimide hydrochloride, or carbonyl compounds, such as carbonyldiimidazole, or 1,2-oxazolium compounds, such as 2-ethyl-5-phenyl-1,2-oxazolium 3-sulphonate or 2-tert-butyl-5-methyl-isoxazolium perchlorate, or acylamino compounds, such as 2-ethoxy-1-ethoxycarbonyl-1,2-dihydroquinoline, or propanephosphonic acid anhydride, or isobutyl chloroformate, or benzotriazolyloxy-tris(dimethylamino)phosphonium hexafluorophosphate, or, as bases, alkali metal carbonates, for example sodium or potassium carbonate or bicarbonate, or organic bases, such as trialkylamines, for example triethylamine, N-ethylmorpholine or N-methylpiperidine.

Suitable solvents are the customary inert solvents which do not change under the particular chosen reaction conditions, above all the particular chosen method of activation. These include, preferably, water or organic solvents, such as methanol, ethanol, propanol, isopropanol or ethers, such as diethyl ether, glycol monomethyl or dimethyl ether, dioxane or tetrahydrofuran, or hydrocarbons, such as benzene, toluene, xylene, cyclohexane or petroleum fractions, or halogenohydrocarbons, such as methylene chloride, chloroform or carbon tetrachloride, or acetone, dimehtylsulphoxide, dimethylformamide, hexamethylphosphoric acid triamide, ethyl acetate, pyridine, triethylamine or picoline. It is also possible to use mixtures of the solvents mentioned.

Salts of the compounds according to the invention with salt-forming groups can be prepared in a manner which is known per se, for example by reaction of the compounds according to the invention containing acid groups with corresponding bases or by reaction of the compounds according to the invention containing basic groups with corresponding acids, in each case preferably with the abovementioned bases or acids.

Stereoisomer mixtures, in particular diastereomer mixtures, can be resolved into the individual isomers in a manner which is known per se, for example by fractional crystallization or chromatography.

Racemates can be split into diastereomers in a manner which is known per se, for example by conversion of the optical antipodes.

The preparation of the compounds according to the invention has also been carried out by other customary variants of the process described (compare, for example, Houben-Weyls "Methoden der organischen Chemie" ("Methods of Organic Chemistry") XV/1 and 2; M. Bodanszky, A. Bodanszky in "The Practice of Peptide Synthesis", Springer Verlag, Berlin, 1984; George R. Pettit in "Synthetic Peptides", Volume 4, Elsevier Scientific Publishing Company, Amsterdam-Oxford-New York, 1976; E. Gross and J. Meienhofer (Editors) in "The Peptides", Volume 1–3, Academic Press, New York-London-Toronto-Sydney-San Francisco, 1981; M. Bodanszky in "Principles of Peptide Synthesis", Springer Verlag, Berlin-Heidelberg-New York-Tokyo, 1984; and R. Uhmann and K. Radscheit, Offenlegungsschrift (Published Specification) DE No. 3,411,244 A1), or by the "solid phase method", such as is described, for example, by M. Bodanszky and A. Bodanszky in "The Practice of Peptide Synthesis", Springer-Verlag, Berlin, 1984 or G. Barany and R. B. Merrifield in "Solid-Phase Peptide Synthesis" from "The Peptides", Volume 2, pages 3–254, edited by E. Gross, J. Meienhofer, Academic Press, New York-London-Toronto-Sydney-San Francisco (1980).

The amino acids, employed as starting substances, in the definition of B, D, G, J, L and M are known or can be obtained by known methods, or are naturally occurring amino acids [Houben-Weyls "Methoden der organische Chemie" ("Methods of Organic Chemistry") Volume XV/1 and 2). The amino acids Dl-, D- and L-(1-triazolyl)alanine in protected and unprotected form are new. They are prepared from N-acetyl-dehydroalanine ethyl ester [H. Hellmann, H. Teichmann and F. Ringens, Chem. Ber. 91, 2427–2431 (1958)], triazole and sodium, as described by Wieland in Chem. Ber. 90, 194 (1957).

The amino acids, employed as starting substances both in their amino-protected form and as esters, of the formula (II)

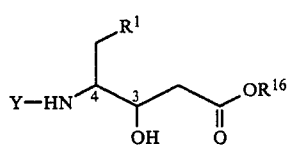  (II)

in which
R¹ represents a group of the formula

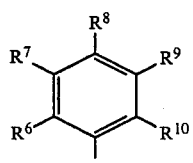

wherein $R^6$, $R^7$, $R^8$, $R^9$ and $R^{10}$ are identical or different and represents hydrogen, $C_1$-$C_6$-alkyl, $C_1$-$C_6$-alkoxy, halogen, hydroxyl, cyano, trifluoromethyl, trifluoromethoxy, trifluoromethylthio or nitro, or represent a group of the formula

wherein
$R^{11}$ and $R^{12}$ are identical or different and represent hydrogen, $C_1$-$C_6$-alkyl, aryl, aralkyl, phenylsulphonyl, tolylsulphonyl, $C_1$-$C_6$-alkylsulphonyl, acetyl or benzoyl, or represent an amino-protective group, with the proviso that at least one of the substituents $R^6$, $R^7$, $R^8$, $R^9$ or $R^{10}$ must represent nitro or the group $NR^{11}R^{12}$, $R^{16}$ represents hydrogen, or represents straight-chain or branched $C_1$-$C_{12}$-alkyl which is optionally interrupted in the chain by an oxygen atom, and Y represents hydrogen, $C_7$-$C_{14}$-aralkyl, $C_1$-$C_8$-alkyl, phenylsulphonyl, tolylsulphonyl, $C_1$-$C_8$-alkylsulphonyl, or represents an amino-protective group, are new and can be prepared by a process in which aldehydes of the general formula (III)

  (III)

in which
$R^1$ has the meaning given and
Y' has the meaning of Y but does not represent hydrogen, are reacted with acetic acid esters of the general formula (IV)

$$H_3C-COOR^{16'} \quad\quad (IV)$$

in which
$R^{16'}$ represents straight-chain or branched alkyl which has up to 12 carbon atoms, preferably up to 6 carbon atoms, and is optionally interrupted in the chain by an oxygen atom, in inert organic solvents, if appropriate in the presence of a base, and, if appropriate, the stereoisomer mixture obtained is resolved by customary methods and, if appropriate, protective groups are then split off.

Solvents which can be used are the customary organic solvents which do not change under the reaction conditions. These include, preferably, alcohols, such as methanol, ethanol, propanol or isopropanol, or ethers, such as diethyl ether, dioxane, tetrahydrofuran or glycol mono- or -diethyl ether, or hydrocarbons, such as benzene, toluene, xylene or petroleum fracions, or dimetylformamide or hexamethylphosphoric acid triamide. It is also possible to employ mixtures of the solvents mentioned.

Suitable bases are the customary inorganic or organic bases. These include, preferably, alkali metals, such as, for example, sodium, or alkali metal hydrides, such as, for example, sodium hydride or potassium hydride, or alkali metal alcoholates, such as, for example, sodium methanolate or ethanolate, or potassium methanolate or ethanolate, or potassium tert.-butylate, or alkali metal amides, such as, for example, sodium amide or lithium diisopropylamide, lithium hexamethyldisilazide, or organometallic compounds, such as, for example, n-, sec- or tert-butyllithium, or phenyllithium, or alkali metal hydroxides, such as sodium hydroxide or potassium hydroxide.

The reaction can be carried out under normal pressure or under increased or reduced pressure. It is in general carried out under normal pressure.

The reaction is carried out in a temperature range from $-100°$ C. to $50°$ C., preferably from $-80°$ C. to $20°$ C.

The isomer mixture obtained is resolved by a customary method, such as is described, for example, by E. L. Eliel in "Stereochemistry of Carbon Compounds", McGraw Hill (1962), and resolution is preferably by a chromatographic route, such as is described, for example, by W. C. Still et al. in J. Org. Chem. 43, 2923 (1978).

If appropriate, the protective groups are split off by known methods, depending on the nature of the protective groups present, such as is described, for example, in Houben-Weyls "Methoden der organischen Chemie" ("Methods of Organic Chemistry") Volume XV/1 and 2.

The acetic ester is in general employed in the reaction in an amount of 0.5 to 5, preferably 1 to 2 mols per mol of the aldehyde, and 1 to 5, perferably 1 to 1.6 mols of the base per mol of the acetic ester is employed.

The preparation of the amino acids of the formula (II) can be illustrated by the following equation:

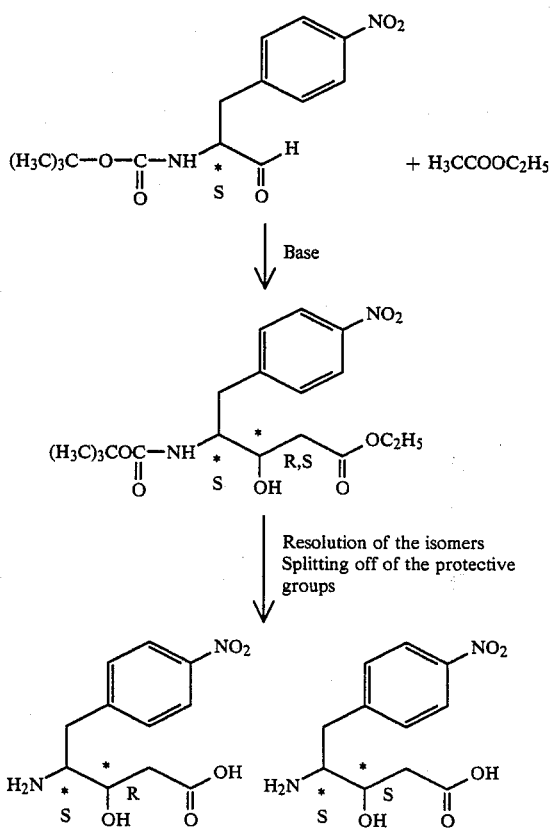

The stereochemically pure 2S- or 2R-forms, particularly preferably the 2S-forms, of the aldehydes (III) are preferably employed as starting substances in the preparation of the amino acids of the formula (II) according to the invention.

The aldehydes of the general formula (III) employed as starting substances are new.

They are prepared by a process in which [A] Alcohols of the general formula (IV)

in which

Y' and $R^1$ have the meaning given, are oxidized, if appropriate in the presence of a base and/or an auxiliary in inert organic solvents, or in which [B] Amino acid derivatives of the general formula (V)

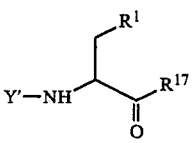

in which $R^1$ and Y' have the meaning given and $R^{17}$ represents hydroxyl, or represents $C_1$-$C_6$-alkoxy, or represents di-$C_1$-$C_4$-alkylamino or 1-imidazolyl, or represents N-methoxy-N-methylamino, are reduced, if appropriate in the presence of an auxiliary.

The processes according to the invention can be illustrated, for example, by the following equation:

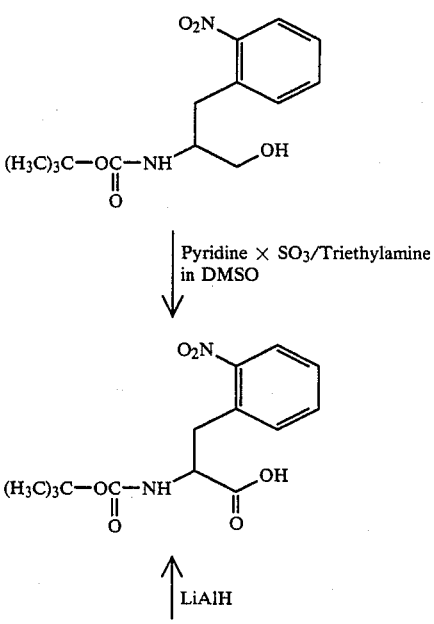

-continued

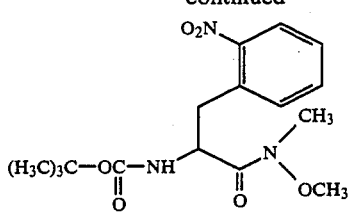

The oxidation in process A can be carried out by customary methods described in the literature. These include: oxidation with chromium-(VI) compounds, preferably with pyridinium chlorochromate, pyridinium dichromate or pyridine/$CrO_3$ in halogen substituted hydrocarbons, such as methylene, chloride or chloroform, or hydrocarbons, such as benzene, toluene or hexane, or ethers, such as diethyl ether, dioxane or tetrahydrofuran, at temperatures from $-80°$ C. to $100°$ C., preferably $-30°$ C. to $50°$ C., as described by C. F. Stanfield, J. E. Parker and P. Kanellis in J. Org. Chem. 46, 4797 (1981) or by E. J. Corey and G. Schmidt in Tetrahedron Letters 1979, 399 or in U.S. Pat. No. 4,397,786 or in Houben-Weyls "Methoden der organischen Chemie" ("Methods of Organic Chemistry") Supplementary Volume 3, page 287 et seq., and furthermore oxidation with pyridine/$SO_3$ or preferably pyridine/$SO_3$/triethylamine in halogenohydrocarbons, such as methylene chloride or chloroform, or hydrocarbons, such as benzene, toluene or xylene, or ethers, such as diethyl ether, dioxane or tetrahydrofuran, or hexamethylphosphoric acid triamide or, preferably, dimethylsulphoxide, as described by J. R. Parika and W. E. von Doering in J. Am. Chem. Soc. 89, 5505 (1967) or Y. Hamada and T. Shioiri in Chem. Pharm. Bull 30, 1921 (1982), or oxidation with dimethylsulphoxide in halogenohydrocarbons, such as methylene chloride or chloroform, or ethers, such as diethyl ether, dioxane or tetrahydrofuran, or dimethylsulphoxide in excess, if appropriate in the presence of dicyclohexylcarbodiimide, N-(3-dimethylaminopropyl)-N'-ethylcarbodiimide hydrochloride, trifluoroacetic anhydride, oxalyl chloride or acetic anhydride, if appropriate in the presence of bases, such as triethylamine, at temperatures from $-80°$ C. to $100°$ C., preferably from $-30°$ C. to $50°$ C., as described in Houben-Weyls "Methoden der organischen Chemie" ("Methods of Organic Chemistry") Supplementary Volume 3, page 275 et seq.

The reduction of the carboxylic acid derivatives by process B can be carried out by customary processes described in the literature. These include, preferably, reduction with hydrides, such as lithium aluminum, hydride, diisobutylaluminum hydride, $BH_3$, diborane, sodium borohydride, sodium cyanoborohydride, tributyl-tin hydride, triethylsilane or dimethylphenylsilane in inert solvents, such as ethers, for example diethyl ether, dioxane or tetrahydrofuran, or halogenohydrocarbons, such as methylene chloride or chloroform, or hydrocarbons, such as benzene, toluene or xylene, if appropriate in the presence of acids, such as acetic acid, dichloroacetic acid, trifluoroacetic acid or methane-, benzene- or toluenesulphonic acid, in a temperature range from $-80°$ C. to $100°$ C., preferably from $-30°$ C. to $50°$ C., or reduction with hydrogen, if appropriate with catalysts, such as Raney nickel, palladium, palladium/animal charcoal or platinum, if appropriate in the presence of acids, such as hydrochloric acid or acetic acid, chloroacetic acid, dichloroacetic acid, trifluoroacetic acid or methane-, benzene- or toluenesulphonic acid, in inert solvents, such as alcohols, for example methanol, ethanol, propanol or isopropanol, or ethers, such as diethyl ether, dioxane or tetrahydrofuran, or hydrocarbons, such as benzene, toluene or xylene, or acetic acid or trifluoroacetic acid, under an increased or reduced pressure of hydrogen (from 0.5 to 100 bar) at temperatures from $-80°$ C. to $100°$ C., preferably from $-30°$ C. to $50°$ C., such as is described, for example, by E. Adams in J. Biol. Chem. 217, 317 (1955) or by K. Balemovic et al., in J. Org. Chem. 18, 297 (1953) or 21, 115 (1956) or by W. Ried and P. Paender in Justus Liebigs Ann. Chem. 640, 111 (1961) or by H. Umezawa et al., in J. Antibiotics (Tokyo) 25, 515 (1972) or by H. Seki, K. Koga and S. Yomada in Chem. Pharm. Bull. 23, 3081 (1975), by D. H. Rich, E. T. Sun and H. S. Bopacci in J. Org. Chem. 43, 3624 (1978) or by R. Streulmann and K. Klostermeyer in Liebigs Ann. Chem. 1975, 2245, by K. E. Rittle, C. F. Hommiek, G. S. Penticello and B. E. Evans in J. Org. Chem. 47, 3016 (1982) or in U.S. Pat. No. 4,397,786.

The alcohols (IV) and amino acid derivatives (V) employed as starting substances are known in some cases or can be prepared by known methods [C. Freeman et al., J. org. Chem. 1981, 46, 4797–4798; (a) Fehrentz, J. A. et al. (1983) Synthesis, 676–678, and (b) Ito, A et al., Chem. Pharm. Bull, 23, 3081-3087 (1975)].

In vitro test

The inhibitory strength of the peptides according to the invention against endogenous resin from human plasma is determined in vitro. Pooled human plasma is obtained, with the addition of ethylenediaminetetraacetic acid (EDTA) as an anticoagulant and is stored at $-20°$ C. The plasma renin activity (PRA) is determined as the rate of formation of angiotensin I from endogenous angiotensinogen and renin after incubation at $37°$ C. The reaction solution contains 150 $\mu$l of plasma, 3 $\mu$l of 6.6% strength 8-hydroxyquinoline sulphate solution, 3 $\mu$l of 10% strength dimercaprol solution and 144 $\mu$l of sodium phosphate buffer (0.2M; 0.1% of EDTA; pH 5.6) with or without the substances according to the invention in various concentrations. The angiotensin I formed per unit time is determined by radioimmunoassay (Sorin Biomedica, Italy). The percentage inhibition of the plasma renin activity is calculated by comparison of the amount of angiotensin I formed here with or without the substances according to the invention.

The concentration range in which the substances according to the invention show a 50% inhibition of the plasma renin activity is between $10^{-4}$ and $10^{-9}$M.

In vivo test

From the current state of the art, it was not to be expected that the compounds according to the invention have a hypotensive action when administered orally. In the context of the present invention here, it is surprising that the peptides according to the invention, such as, for example, the compound of Example 12 according to the invention, both inhibit the renin activity in vitro and have a hypotensive action when administered orally. The unexpected antihypertensive action is observed, for example, on conscious, spontaneously hypertensive rats following oral administration of a dose of 100 mg/kg of Example 12. [See Table 1].

The blood pressure of the conscious animals is thereby measured by the customary indirect measurement method on the tail, using an inflatable occlusion cuff and an infra-tone pulse recorder [compare H.

Breuninger: Methoden zur unblutigen Messung des Blutdrucks an Kleintieren (Methods of bloodless measurement of the blood pressure on small animals), Arzneimittleforschung 6, 222–225 (1956)]. The substance is administered as a suspension in 1% strength Tylose by means of a stomach tube. The systolic blood pressure is measured before and 1, 2, 4 and 6 hours after administration.

The compound also reduces the mean arterial pressure, following intragastral administration, in sodium-deficient spontaneously hypertensive rats (250 mg/l of furosemide in the drinking water for 14 days) anaesthetized with Inactin ®.

TABLE 1

Antihypertensive action of Example 12 on spontaneously hypertensive rats
Influence of an oral dose of 100 mg/kg on the systolic blood pressure (mm Hg).

| Time after administration (hours) | | | | | |
|---|---|---|---|---|---|
| 0 | 1 | 2 | 4 | 6 | n |
| Substance | | | | | |
| 165.0 ± 5.4 | 163.1 ± 5.1 | 161.8 ± 3.5 | 151.8 ± 3.7 | 148.5 ± 3.0 | 6 |
| Control | | | | | |
| 179.0 ± 19.7 | 180.6 ± 18.8 | 178.0 ± 18.4 | 177.0 ± 19.4 | 179.6 ± 18.7 | 3 |

The new active compounds cna be converted in a known manner into the customary formulations, such as tablets, dragees, pills, granules, aerosols, syrups, emulsions, suspensions and solutions, using inert, non-toxic, pharmaceutically suitable excipients or solvents. The therapeutically active compound should in each case be present in a concentration of about 0.5 to 90% by weight of the total mixture, that is to say in amounts which are sufficient to achieve the dosage range stated.

The formulations are prepared, for example, by extending the active compounds with solvents and/or excipients, if appropriate using emulsifying agents and-/or dispersing agents, and, for example, in the case of the use of water as the diluent, organic solvents can be used as auxiliary solvents, if appropriate.

Examples of auxiliaries which may be mentioned are: water, non-toxic organic solvents, such as paraffins (for example petroleum fractions), vegetable oils (for example groundnut/sesame oil) and alcohols (for example: ethyl alcohol and glycerol), carriers, such as, for example, natural rock powders (for example kaolins, aluminas, talc and chalk), synthetic rock powders (for example highly disperse silicic acid and silicates) and sugars (for example sucrose, lactose and glucose), emulsifying agents (for example polyoxyethylene fatty acid esters), polyoxyethylene fatty alcohol ethers (for example ligninsulphite waste liquors, methylcellulose, starch and polyvinylpyrrolidone) and lubricants (for example magnesium stearate, talc, stearic acid and sodium sulphate).

Administration is effected in the customary manner, preferably orally or parenterally, in particular perlingually or intravenously. In the case of oral use, tablets can of course also contain, in addition to the excipients mentioned, additives, such as sodium citrate, calcium carbonate and dicalcium phosphate, together with various additional substances, such as starch, preferably potato starch, gelatine and the like. Lubricants, such as magnesium stearate, sodium lauryl-sulphate and talc, can furthermore be co-used for tablet-making. In the case of aqueous suspensions, various flavor-improving agents or dyestuffs, in addition to the abovementioned auxiliaries, can be added to the active compounds.

In the case of parenteral use, solutions of the active compounds can be employed, using suitable liquid excipients.

In general, it has proved advantageous to administer amounts of about 0.01 to 10 mg/kg, preferably about 0.1 to 5 mg/kg of body weight, in the case of intravenous administration, to achieve effective results, and in the case of oral administration the dosage is about 0.1 to 200 mg/kg, preferably 1 to 100 mg/kg of body weight. Nevertheless, it may at times be necessary to deviate from the amounts mentioned, and in particular to do so as a function of the body weight of the experimental animal and of the nature of the administration, but also because of the species of the animal and its individual behavior towards the medicament or the nature of its formulation and the time or interval at which administration takes place. Thus, it may in some cases be sufficient to manage with less than the abovementioned minimum amount, while in other cases the upper limit mentioned must be exceeded. Where relatively large amounts are administered, it may be advisable to divide these into several individual doses over the course of the day. The same dosage range is envisaged for administration in human medicine. The above statements also apply here in the general sense.

Explanations on the experimental section:
TLC systems:

Stationary phase

Merck TLC pre-coated plates silica gel 60 F-254, 5×10 cm, layer thickness 0.25 mm, Cat. No. 5719.

Mobile phases (in the test as the "TLC system")

| | |
|---|---|
| I: $CH_2Cl_2$/MeOH | 9:1 |
| II: $CH_2Cl_2$/MeOH | 95:5 |
| III: $NH_3$/$CH_2Cl_2$/MeOH | 2:14:10 |
| IV: HOAC/$CH_2Cl_2$/MeOH | 1:14:10 |
| V: glacial acetic acid/n-butanol/$H_2O$ | 1:3:1 |
| VI: toluene/EtOAc | 4:1 |
| VII: Ethyl acetate (EtOAc) | |
| VIII: EtOAc/n-hexane | 5:1 |
| IX: $CH_2Cl_2$/MeOH | 98:2 |
| X: $CH_2Cl_2$/MeOH | 7:3 |
| XI: $NH_3$/$CH_2Cl_2$/MeOH | 0.2:9:1 |
| XII: $CH_2Cl_2$/MeOH | 10:1 |

HPLC systems:
  HPLC system 1: Column: Merck LiChrosorb ® RP-8, 250-4, 10 μm, Cat. No. 50318
  HPLC system II: Column: Merck LiChrosorb ® RP-18, 250-4, 10 μm, Cat. No. 50334
Eluant for system I and II
  A: pH 7.00 phosphate buffer, Merck, Cat. No. 9439/$H_2O$ 1:50
  B: acetonitrile
  A/B as 1/1, flow rate: 2 ml/minute, isocratic, Detection: 254 nm
List of the abbreviations used
1. General analytical methods
  TLC Thin layer chromatography
  PTLC Preparative thick layer chromatography
  GC Gas chromatography
  HPLC High pressure liquid chromatography
  CC Column chromatography
  NMR Nuclear magnetic resonance spectroscopy (protons)
  MS Mass spectrometry (electron impact ionization)

(+)FAB-MS Fast atomic bombardment mass spectrometry, positive ions, matrix substance: m-nitrobenzyl alcohol MS-DCI Mass spectrometry, chemical ionization 2. Amino acids The configuration is in general designated by placing an L or D before the amino acid abbreviation, and by D,L- in the case of the racemate, and for simplification, the configuration designation can be omitted for L-amino acids and then explicit designation being given only in the case of the D-form or the D,L-mixture.

(a) Naturally occurring amino acids

Ala L-alanine
Arg L-arginine
Asn L-asparagine
Asp L-aspartic acid
Cys L-cysteine
Gln L-glutamine
Glu L-glutamic acid
Gly L-glycine
His L-histidine
Ile L-isoleucine
Leu L-leucine
Lys L-lysine
Met L-methionine
Orn L-ornithine
Phe L-phenylalanine
Ser L-serine
Sar L-sarcosine (N-methylglycine)
Thr L-threonine
Trp L-tryptophan
Tyr L-tyrosine
Val L-valine (b) Non-naturally occurring amino acids

| D- or L-Nal(1) | β-(1-naphthyl)-D- or -L-alanine |
| D- or L-Nal(2) | β-(2-naphthyl)-D- or -L-alanine |
| D- or L-Phe(2NO$_2$) | β-(2-nitrophenyl)-D- or -L-alanine |
| D- or L-Phe(3NO$_2$) | β-(3-nitrophenyl)-D- or -L-alanine |
| D- or L-Phe(4NO$_2$) | β-(4-nitrophenyl)-D- or -L-alanine |
| D- or L-Phe(2NH$_2$) | β-(2-aminophenyl)-D- or -L-alanine |
| D- or L-Phe(3NH$_2$) | β-(3-aminophenyl)-D- or -L-alanine |
| D- or L-Phe(4NH$_2$) | β-(4-aminophenyl)-D- or -L-alanine |
| D- or L-Phe(3,4-Cl$_2$) | β-(3,4-dichlorophenyl)-D- or -L-alanine |
| D- or L-Phg | D- or L-phenylglycine |
| D- or L-Pyr(2) | β-(2-pyridyl)-D- or -L-alanine |
| D- or L-Pyr(3) | β-(3-pyridyl)-D- or -L-alanine |
| D- or L-Pyr(4) | β-(4-pyridyl)-D- or -L-alanine |
| D- or L-Trz(1) | β-(1-triazolyl)-D- or -L-alanine |
| D- or L-Phe(4I) | β-(4-iodophenyl)-D- or -L-alanine |
| D- or L-Phe(4OCH$_3$) | β-(4-methoxyphenyl)-D- or -L-alanine |

3. Activation groups
   HOBT 1-hydroxybenzotriazole
   HOSU N-hydroxysuccinimide
4. Coupling reagents
   DCC dicyclohexylcarbodiimide
   DPPA diphenylphosphoryl azide
   PPA n-propanephosphonic acid anhydride
   BOP benzotriazolyloxy-tris(dimethylamino)phosphoniumhexafluorophosphate
5. Reagents
   NEM N-ethylmorpholine
   NMM N-methylmorpholine
   TEA triethylamine
   TFA trifluoroacetic acid
6. Solvents
   HOAc acetic acid
   DMF dimethylformamide
   EtOAc ethyl acetate
   MeOH methanol
   EtOH ethanol
   THF tetrahydrofuran
   DMSO dimethylsulphoxide
   HMPT hexamethylphosphoric acid triamide
7. Protective groups
   Boc tert.-butoxycarbonyl
   Z benzyloxycarbonyl
   DNP dinitrophenyl
   Fmoc 9-fluorenylmethoxycarbonyl
   OEt ethyl ester
   OMe methyl ester
8. Others
   DCU N,N'-dicyclohexylurea

PREPARATION EXAMPLES

EXAMPLE 1

L-(4-Nitrophenyl)alanine

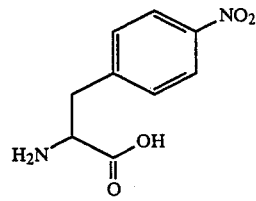

250 g (1.5 mols) of L-phenylalanine are dissolved in 750 ml of concentrated sulphuric acid, while cooling with ice. 146.8 ml of 65% strength nitric acid are added dropwise, while cooling with dry ice/acetone, so that the temperature does not exceed 5° C. The mixture is subsequently stirred for a further 15 minutes and poured onto 1 kg of water-ice, and 500 g of solid sodium hydroxide are added carefully to the reaction mixture in small portions. The mixture is brought to pH 7 with about 1 l of concentrated ammonia solution (25% strength). After cooling, the crude product which has precipitated is filtered off with suction and recrystallized from 7.5 l of water.

Yield: 188.8 g (73.4% of theory)
Melting point: 245° C.
$^1$H-NMR (NaOD, 200 MHz): δ=8.2 (d, 2H); 7.6 (d, 2H); 3.6 (m, 1H); 3.1 (m, 2H).
TLC system III: R$_f$=0.71; IV: R$_f$=0.42.

EXAMPLE 2

L-(4-Nitrophenyl)alanine methyl ester hydrochloride

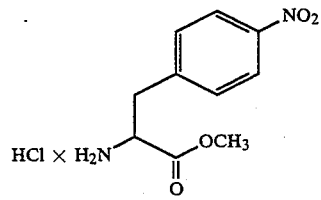

21 ml of thionyl chloride are added dropwise to 160 ml of analytical grade methanol at −5° C. 105.1 g (0.5 mol) of L-(4-nitrophenyl)alanine are then introduced in portions at a temperature of 5° C. and the mixture is stirred under reflux overnight. A further 100 ml of analytical grade methanol are added, the mixture is cooled to −5° C. and a further 23 ml of thionyl chloride are added dropwise. The mixture is stirred under reflux for a further 4 hours and concentrated to dryness on a toary evaporator. The crude product is recrystallized from 600 ml of methanol, filtered off with suction and rinsed with diethyl ether.

Yield: 93 g (71.7% of theory)
Melting point: 232° C., decomposition
$^1$H-NMR (D$_2$O, 200 MHz): δ=8.3 (d, 2H); 7.6 (d, 2H); 4.6 (m, 1H); 3.9 (s, 3H); 3.5 (m, 2H).
TLC system II: R$_f$=0.54; IV: R$_f$=0.93.

EXAMPLE 3

N-tert.-Butoxycarbonyl-L-(4-nitrophenyl)alanine methyl ester

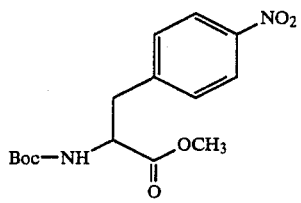

81.4 g (0.31 mol) of L-(4-nitrophenyl)alanine methyl ester hydrochloride are dissolved in 630 ml of anhydrous dioxane, and first 43.7 ml of triethylamine and then 76.0 g of di-tert.-butyl pyrocarbonate are added dropwise, while cooling with ice. The mixture is stirred at room temperature for 2 hours, the pH is adjusted to 8.5 with triethylamine and the mixture is allowed to further react overnight at room temperature. The reaction mixture is carefully brought to pH 3 with dilute hydrochloric acid, while cooling, and the crude product is precipitated by addition of water. After drying over P$_2$O$_5$, the product is recrystallized from tetrahydrofuran/n-hexane.

Yield: 75.9 g (74.6% of theory)
Melting point: 94°–96° C.
$^1$H-NMR (CDCl$_3$, 200 MHZ): δ=8.15 (d, 2H); 7.23 (d, 2H); 5.1 (d, 1H); 4.65 (m, 1H); 3.75 (s, 3H); 3.2 (m, 2H); 1.4 (s, 9H).

EXAMPLE 4

N-tert.-Butoxycarbonyl-L-(4-nitrophenyl)alaninol

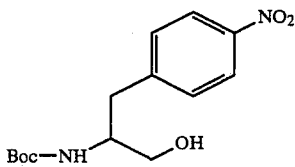

40 g (0.12 mol) of N-tert.-butoxycarbonyl-L-(4-nitrophenyl)alanine methyl ester are dissolved in 400 ml of analytical grade THF, 9.4 g (200 mol %) of NaBH$_4$ are added and the mixture is stirred under gentle reflux (50°–55° C.) for 15 minutes. 99 ml of analytical grade methanol are then carefully added dropwise at this temperature in the course of 1 hour. The mixture is stirred overnight at room temperature, 247 ml of water are added and the solvents are stripped off on a rotary evaporator. 400 ml of a saturated sodium chloride solution are added to the residue and the crude product is extracted three times with 600 ml of ether each time. The combined organic phases are washed with saturated sodium chloride solution, dried with MgSO$_4$ and concentrated to dryness in vacuo.

Yield: 35.5 g (97.4% of theory)
Melting point: 132° C.
$^1$H-NMR (CDCl$_3$, 300 MHZ): δ=8.15 (d, 2H); 7.40 (d, 2H); 4.85 (d, 1H); 3.9 (s, broad, 1H); 3.62 (m, 2H); 2.97 (m, 2H); 2.29 (m, 1H); 1.30 (s, 9H).
TLC system II: R$_f$=0.51

EXAMPLE 5

N-tert.-Butoxycarbonyl-L-(4-nitrophenyl)alaninal

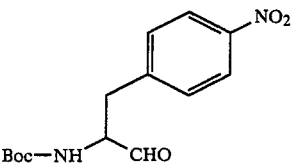

Variant A:

A solution of 32.3 ml of pyridinium sulphate in 210 ml of dimethylsulphoxide is added dropwise to a solution of 20 g (67.5 mmol) of N-tert.-butoxycarbonyl-L-(p-nitrophenyl)alaninol and 28.4 ml of triethylamine in 210 ml of dimethylsulphoxide at room temperature. The mixture is subsequently stirred for 15 minutes, poured onto 800 ml of ice-water and extracted 3 times with 500 ml of diethyl ether each time. The combined organic phases are washed in succession with 2 portions of 10% strength citric acid, 2 portions of water and 2 portions of saturated sodium bicarbonate solution and then dried with magnesium sulphate and concentrated on a rotary evaporator at a maximum bath temperature of 30° C., and the residue is dried under a high vacuum (oil, colors yellow with 2,4-dinitrophenylhydrazine).

Yield: 18.8 g (94.7% of theory
$^1$H-NMR (CDCl$_3$, 200 MHz): δ=9.66 (s, 1H); 8.18 (m, 2H); 7.37 (d, 2H); 5.13 (d, 1H); 4.45 (m, 1H); 3.25 (m, 2H); 1.40 (s, 9H).
TLC system II: R$_f$=0.46
MS (DCI): m/z 295 (M+1), m/z 312 (M+NH$_4$+)

Variant B:

2.55 g (125 mol %) of powdered lithium aluminum hydride are added to a solution, cooled to 0° C., of 19 g (54 mmol) of N-tert.-butoxycarbonyl-L-(4-nitrophenyl-)analyl-(N'-methoxy)methylamide (Example 62) in 250 ml of tetrahydrofuran. After stirring for 30 minutes, the reaction is complete, according to a check by TLC. A solution of 13 g of sodium bisulphate hydrate in 200 ml of water is carefully added to the batch (evolution of hydrogen gas!), and the mixture is subsequently stirred for a short time and then extracted with 2 portions of 300 ml of diethyl ether. The combined phases are washed with 1N hydrochloric acid, saturated sodium bicarbonate solution and sodium chloride solution, dried with sodium sulphate and concentrated in vacuo.

Yield: 15.9 g (100% of theory)
Analytical data as already given under variant A.

EXAMPLE 6

Ethyl N-tert.-butoxycarbonyl-4S-amino-3R,S-hydroxy-5-(4-nitrophenyl)pentanoate

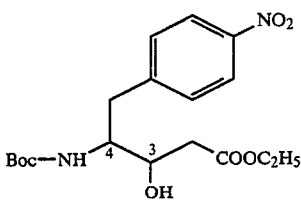

72.3 ml (160 mol %) of n-butyllithium are added dropwise to 15 ml (160 mol %) of diisopropylamine in 50 ml of analytical grade tetrahydrofuran at −20° C. under nitrogen and the mixture is subsequently stirred at this temperature for 15 minutes. It is cooled to −80° C. (cooling bath: acetone, dry ice and liquid nitrogen) and 10.5 ml (160 mol %) of ethyl acetate are added at a temperature of less than −75° C. After 10 minutes, a precooled solution of 18.6 g (64 mmol) of N-tert.-butoxycarbonyl-L-(4-nitrophenyl)alaninal (example 5) in 70 ml of tetrahydrofuran is added dropwise so that the temperature of the reaction mixture remains below −75° C. The mixture is subsequently stirred for 15 minutes and 50 ml of 2N HCl are then added. The mixture is warmed to 10° C. and brought to pH 2.5 with 2N HCl. At room temperature, the mixture is extracted 3 times with 600 ml of diethyl ether each time and the combined organic phases are washed twice with 100 ml of saturated sodium chloride solution each time, dried with magnesium sulphate and concentrated to dryness on a rotary evaporator.

Crude yield: 21.2 g (83.3% of theory).

EXAMPLE 7 AND EXAMPLE 8

Ethyl N-tert.-butoxycarbonyl-4S-amino-3S- and 3R-hydroxy-5-(4-nitrophenyl)pentanoate

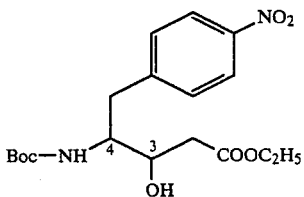

The two diastereomeric products are resolved by column chromatography of the mixture from Example 6 on Merck silica gel 60, Cat. No. 7734, particle size 0.063–0.2 mm, with the mobile phase system toluene-/ethyl acetate 8:2 (ratio of stationary phase/mixture to be resolved: 75:1).

The 3S,4S-isomer (Example 7) is eluted first, followed by the 3R,4S-isomer (Example 8).

EXAMPLE NO. 7

$^1$H-NMR (CDCl$_3$, 300 MHz) δ=8.15 (d, 2H); 7.42 (d, 2); 4.99 (d, 1H); 4.14 (q, 2H); 3.95 (d, 1H); 3.79 (m, 1H); 3.63 (s (broad) 1H); 3.04 (m, 2H); 2.60 (m, 1H); 2.39 (m, 1H); 1.39 (s, 9H); 1.26 (t, 3H).

TLC system VI: R$_f$=0.21
HPLC, system II: R$_t$=5.31 minutes
Melting point: 114°–116° C.

EXAMPLE NO. 8 $^1$H-NMR (CDCl$_3$, 200 MHz) δ=8.15 (d, 2H); 7.42 (d, 2H); 4.62 (d, 1H); 4.20 (q, 2H); 3.90 (m, 2H); 3.60 (s, (broad) 1H); ;b 3.19 (m, 1H); 2.90 (m, 1H); 2.65 (m, 2H); 1.40–1.25 (m, 12H).

TLC system VI: R$_f$=0.13
HPLC, system II. R$_t$=4.66 minutes
Melting point: 171°–174° C.

EXAMPLE 9

N-tert.-Butoxycarbonyl-4S-amino-3S-hydroxy-5-(4-nitrophenyl)pentanoic acid

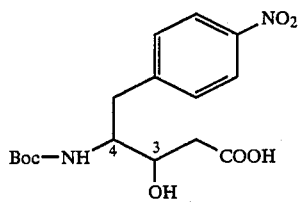

3.6 g (9.4 mmol) of ethyl N-tert.-butoxycarbonyl-4S-amino-3S-hydroxy-5-(4-nitrophenyl)pentanoate are suspended in 50 ml of dioxane/water 1:1. Dioxane is added, with stirring, until solution is complete, the solution is brought to pH 12–13 with 1N sodium hydroxide and this pH value is maintained by addition of 1N sodium hydroxide, with pH meter control. According to TLC, reaction was still not complete after 4 hours. 10 ml of ethanol are added, the pH value is brought to 13.5 and the batch is then stirred overnight. The reaction mixture is brought to pH 6.5 with 1N hydrochloric acid, the dioxane is stripped off on a rotary evaporator and the residue is rendered alkaline again (pH 11) with sodium bicarbonate solution. The aqueous phase is washed once with diethyl ether, brought to pH 3 with 1N hydrochloric acid and extracted with ethyl acetate. The organic phase is dried with sodium sulphate and concentrated to dryness on a rotary evaporator.

Yield: 2.2 g (66% of theory)
Melting point: 168° C. (decomposition)
$^1$H-NMR (CDCl$_3$+DMSO, 300 MHz): δ=8.11 (d, 2H); 7.44 (d, 2H); 5.55 (d, 1H); 3.96 (m, 1H); 3.81 (m, 1H); 2.99 (m, 2H); 2.33–2.48 (m, 2H); 1.37 (s, 9H).
(+)FAB-MS: m/z 355 (M+H); m/z 299; m/z 255.
TLC system I: R$_f$=0.24; V: R$_f$=0.75.

EXAMPLE 10

N-tert.-Butoxycarbonyl-4S-amino-3S-hydroxy-5-(4-nitrophenyl)pentanoyl-L-isoleucine methyl ester

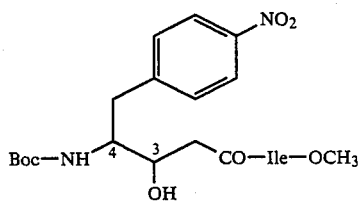

0.49 ml of N-methylmorpholine (120 mol %) is added to a suspension of 0.73 g (110 mol %) of isoleucine methyl ester hydrochloride in 30 ml of methylene chloride. The solution is cooled to 0° C., while stirring, and 1.3 g (3.7 mmol) of N-tert.-butoxycarbonyl-4S-amino-3S-hydroxy-5-(4-nitrophenyl)pentanoic acid, 0.6 g (120 mol %) of N-hydroxysuccinimide and 0.83 g (110 mol %) of DCC (dissolved in 15 ml of methylene chloride) are added.

The mixture is stirred at 5° C. overnight and filtered off with suction again from the DCU, and the filtrate is cooled on dry ice and filtered off with suction again from the DCU. The filtrate is washed in each case twice with saturated sodium bicarbonate solution, cold 0.1N hydrochloric acid and saturated sodium chloride solution. The organic phase is dried with magnesium sulphate and concentrated to dryness on a rotary evaporator.

Yield: 1.8 g (100% of theory)

Melting point: 73°–77° C. $^1$H-NMR (CDCl$_3$, 200 MHz): δ=8.15 (d, 2H); 7.45 (d, 2H); 6.63 (d, 1H); 5.10 (d, 1H); 4.55 (m, 1H); 3.90 (m, 1H); 3.73 (s, 3H); 3.05 (m, 2H); 2.55 (m, 1H); 2.30 (m, 1H); 1.90 (m, 1H); 1.40 (s, 9H); 1.37 (m, 2H); 0.92 (m, 6H).

(+)FAB-MS: m/x 482 (M+H), m/z (M+Na)

TLC system I: R$_f$=0.57

EXAMPLE 11

4S-Amino-3S-hydroxy-5-(4-nitrophenyl)pentanoyl-L-isoleucine methyl ester hydrochloride

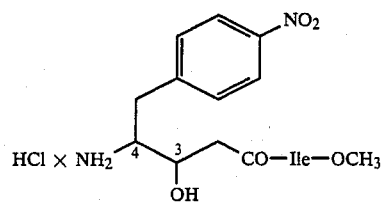

1.15 ml of 4N HCl in dioxane are added to 1.1 g (2.3 mmol) of N-tert.-butoxycarbonyl-4S-amino-3S-hydroxy-5-(4-nitrophenyl)-pentanoyl-L-isoleucine methyl ester and the mixture is stirred at room temperature. After ½ hour, it is concentrated to dryness on a rotary evaporator and the residue is dried under a high vacuum overnight.

Yield: 1.1 g (114% of theory) (hygroscopic)

(+)FAB-MS: m/z 382 (M+H)

TLC system I: R$_f$=0.29

TLC system IV: R$_f$=0.87

TLC system V: R$_f$=0.79

TLC system XI: R$_f$=0.51

HPLC value, system II: R$_t$=5.38 minutes

EXAMPLE 12

N-tert.-Butoxycarbonyl-phenylalanyl-L-histidyl-4S-amino-3S-hydroxy-5-(4-nitrophenyl)pentanoyl-L-isoleucine methyl ester

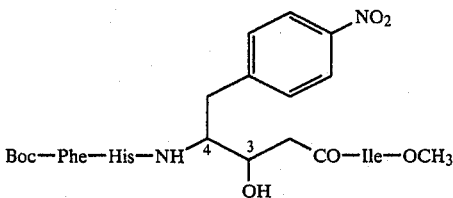

0.6 g (1.4 mmol) of 4S-amino-3S-hydroxy-5-(4-nitrophenyl)-pentanoyl-L-isoleucine methyl ester hydrochloride and 0.174 ml (110 mol %) of N-methylmorpholine are suspended in 15 ml of CH$_2$Cl$_2$, the suspension is cooled to 0° C., while stirring, and 0.29 g (150 mol%) of HOBT, 0.39 g (130 mol %) of DCC and 0.69 g of N-tert.-butoxycarbonyl-L-phenylalaninyl-L-histidine are then added. The reaction mixture is allowed to warm to room temperature overnight, the DCU which has precipitated is filtered off and the filtrate is cooled on dry ice and filtered off with suction from the DCU subsequently precipitated. The filtrate is washed in each case twice with saturated sodium chloride solution. The organic phase is dried with sodium sulphate and the solvent is stripped off on a rotary evaporator. The resulting crude product (0.9 g) is chromatographed over 75 g of silica gel, Merck silica gel 60, particle size 0.063–0.200 mm, Cat. No. 7734 with the mobile phase system methylene chloride/methanol 95/5. The clean fractions containing the product are combined and concentrated to dryness.

Yield: 319 mg (29% of theory)

TLC system I: R$_f$=0.55

HPLC value system I: R$_t$=6.29 minutes (+)FAB-MS: m/z 766 (M+H).

EXAMPLE 13

N-tert.-Butoxycarbonyl-L-phenylalanyl-L-phenylalanyl-4-S-amino-3S-hydroxy-5-(4-nitrophenyl)pentanoyl-L-isoleucine methyl ester

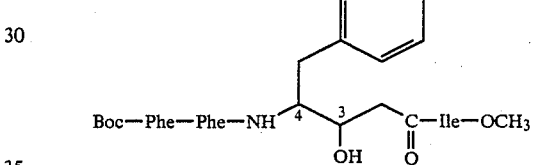

The title compound is prepared analogously to Example 12. Starting from 0.3 g (9.72 mmol) of the hydrochloride (Example 11.), 190 mg are obtained after chromatography.

Yield: 190 mg (33% of theory)

TLC system I: R$_f$=0.68

HPLC values: system I: R$_t$=12.62 minutes; system II: R$_t$=21.90 minutes.

(+)FAB-MS: m/z 776 (M+H)

EXAMPLE 14

N-tert.-Butoxycarbonyl-4S-amino-3R-hydroxy-5-(4-nitrophenyl)pentanoic acid

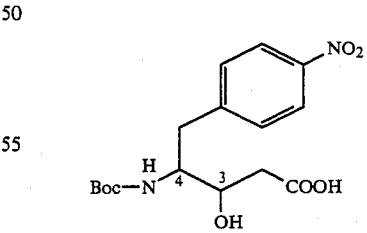

The title compound is prepared analogously to Example 9 from 3 g (7.8 mmol) of ethyl N-tert.-butoxycarbonyl-4S-amino-3R-hydroxy-5-(4-nitrophenyl)pentanoate.

Yield: 1.7 g (61% of theory)

Melting point: 198°–204° C. decomposition

TLC system II: R$_f$=0.24

$^1$H-NMR (CDCl$_3$+DMSO, 300 MHz): δ=8.10 (d, 2H); 7.4 (d, 2H); 5.50 (d, 1H); 4.01 (m, 1H); 3.74 (m, 1H);

3.15 (m, 1H); 2.85 (m, 1H); 2.40–2.60 (m, 2H); 1.27 (s, 9H).

(+)FAB-MS: m/z 355 (M+H); m/z 299; m/z 255

EXAMPLE 15

N-tert.-Butoxycarbonyl-4S-amino-3R-hydroxy-5-(4-nitrophenyl)pentanoyl-L-isoleucine methyl ester

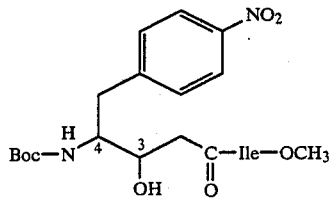

The title compound is prepared analogously to Example 10 from 1.3 g (3.4 mmol) of Example 14 and isoleucine methyl ester hydrochloride.

Yield: 1.4 g (85.5% of theory)
TLC system I: $R_f$=0.61
(+)FAB-MS: m/z 482 (M+H)

EXAMPLE 16

4S-Amino-3R-hydroxy-5-(4-nitrophenyl)pentanoyl-L-isoleucine methyl ester hydrochloride

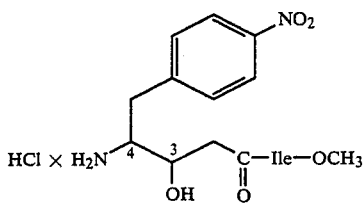

The title compound is prepared analogously to Example 11 from 1.18 g (2.4 mmol) of Example 15.
Yield: 1.23 g (120% of theory) hygroscopic
Melting point: —(+)FAB-MS: m/z 382 (M+H)

EXAMPLE 17

N-tert.-Butoxycarbonyl-L-phenylalanyl-L-histidyl-4S-amino-3R-hydroxy-5-(4-nitrophenyl)pentanoyl-L-isoleucine methyl ester

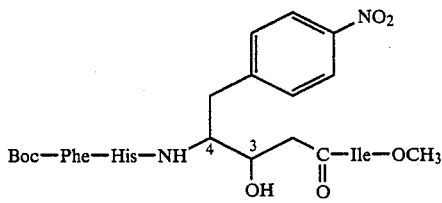

The title compound is prepared analogously to Example 12 from 0.61 g (1.2 mmol) of Example 16.
Yield: 684 mg (74% of theory)
Melting point: —(amorphous)
TLC system I: $R_f$=0.56
HPLC value; system II: $R_t$=5.94 minutes
(+)FAB-MS: m/z 766 (M+H)

EXAMPLE 18

N-tert.-Butoxycarbonyl-L-(4-aminophenyl)alanine

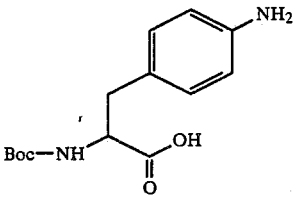

36 g (110 mmol) of N-tert.-butoxycarbonyl-L-(4-nitrophenyl)alanine (A. V. Schally et al., J. Med. Chem. 16, 828 (1973) are dissolved in 500 ml of methanol, 5 g of palladium-on charcoal (10% strength) are added and hydrogenation is carried out under normal pressure for 3 days. The catalyst is filtered off and the solvent is stripped off in vacuo. Recrystallization from diethyl ether gives the title compound in an extremely pure form.

Yield: 12.8 g (40% of theory)
Melting point: 145° C.
$^1$H-NMR (DMSO, 200 MHz); δ=6.90 (m, 2H); 6.40 (m, 2H); 4.03 (m, 1H); 3.37 (broad, 2H); 2.75 (dd, 1H); 2.65 (dd, 1H); 1.30 (S, 9H).

EXAMPLE 19

N-tert.-Butoxycarbonyl-L-[4-(N-9-fluorenylmethoxycarbonyl)-aminophenyl]alanine

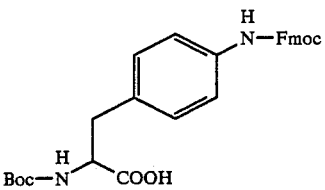

8.4 g (30 mmol) of N-tert.-butoxycarbonyl-L-(4-aminophenyl)alanine are dissolved in 35 ml of water, with the addition of 3.5 g of soidum carbonate. A suspension of 9-fluorenylmethoxycarbonyl-O-hydroxysuccinimide ester (Fmoc-OSU) is added and the reaction mixture is stirred at room temperature for 3 days. The voluminous precipitate formed is filtered off with suction and suspended in 1 l of water. The aqueous phase is brought to pH 4 with hydrochloric acid and extracted twice with 300 ml of methylene chloride each time. The combined organic phases are dried over sodium sulphate, filtered and concentrated on a rotary evaporator. The amorphous crude product (14.9 g) is recrystallized from 800 ml of water/isopropanol 7:3.

Yield: 10.5 g (77% of theory)
Melting point: 115° C.
TLC value system X: $R_f$=0.80
$^1$H-NMR (DMSO, 300 MHz): δ=12.55 (b, 1H); 9.66 (S, 1H); 7.90 (m, 2H); 7.23 (m, 2H); 6.80–7.50 (m, 10H); 4.44 (m, 2H); 4.29 (m, 1H); 4.06 (m, 1H); 2.96 (dd, 1H); 2.78 (dd, 1H); 1.29 (s, 9H).

(+) FAB-MS: m/z 503 (M+H); m/z 447; m/z 403.

EXAMPLE 20

N-tert.-Butoxycarbonyl-L-{4-(N9-fluorenylmethoxycarbonyl)-aminophenyl]alaninyl-4S-amino-3S-hydroxy-5-(4-nitrophenylpentanoyl-L-isoleucine methyl ester

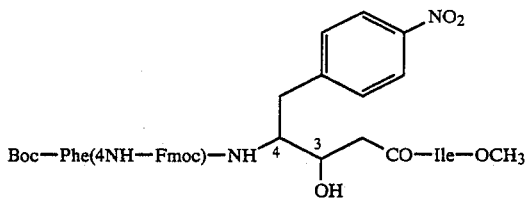

The title compound is prepared by the DCC/HOBT method (as Example 12) from 0.48 g (1 mmol) of Example 11.) and 0.60 g (1.2 mmol) of Example 19.).

Chromatography on silica gel with CH$_2$Cl$_2$/MeOH 9:1 gives the product in a pure form.

Yield: 620 mg (70% of theory)
Melting point: amorphous
TLC system I: R$_f$=0.7
(+)FAB-MS: m/z 866 (M+H); m/z 888 (M+Na); m/z 787, m/z 766.

EXAMPLE 21

N-tert.-Butoxycarbonyl-L-(4-aminophenyl)alanyl-4S-amino-3S-hydroxy-5-(4-nitrophenyl)pentanoyl-L-isoleucine methyl ester

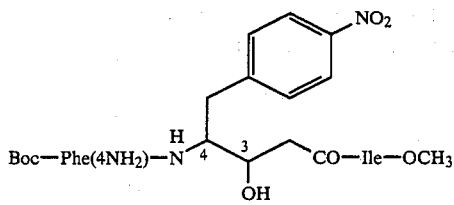

The title compound is obtained analogously to Example 24 by splitting off the Fmoc protective group from 55 mg (0.063 mmol) of Example 20.

Yield: 20.6 mg (50% of theory)
TLC system I: R$_f$=0.52
TLC system II: R$_f$=0.11
HPLC value; system I: R$_t$=4.94 minutes
(+)FAB-MS: m/z 777 ((M+C$_7$H$_5$NO$_3$)—H$_2$O))

EXAMPLE 22

L-4-{N(-9-Fluorenylmethoxycarbonyl)aminophenyl]alanyl-4S-amino-3S-hydroxy-5-(4-nitrophenyl)pentanoyl-L-isoleucine methyl ester hydrochloride

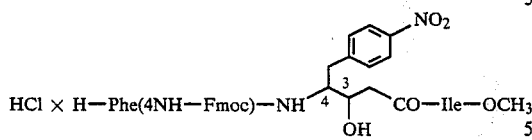

The title compound is obtained from 544 mg (0.62 mmol) of Example 20 by splitting off of the α-aminoprotective group, as described in Example 11, under acid conditions.

Yield: 440 mg (87% of theory)
Melting point: —(amorphous, hygroscopic)
TLC system I: R$_f$=0.68
(+)FAB-MS: m/z 766 (M+H)

EXAMPLE 23

N-tert.-Butoxycarbonyl-L-phenylalanyl-L-4-{N-(9-fluorenylmethoxycarbonyl)aminophenyl}alanyl-4S-amino-3S-hydroxy-5-(4-nitrophenyl)pentanoyl-L-isoleucine methyl ester

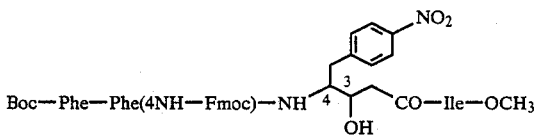

The title compound is prepared from 257 mg (0.32 mmol) of Example 22 and N-tert.-butoxycarbonyl-L-phenylalanine by the DCC/HOBT method (analogously to Example 12). The substance is obtained in an analytically pure form from the crude product by chromatography on silica gel with the mobile phase mixture CH$_2$Cl$_2$/MeOH 98:2.

Yield: 75 mg (23% of theory)
Melting point: —(amorphous)
TLC system IX: R$_f$=0.27
(+)FAB-MS: m/z 1035 (M+Na); m/z 913; m/z 938

EXAMPLE 24

N-tert.-Butoxycarbonyl-L-phenylalanyl-L-(4-aminophenyl)alanyl-4S-amino-3S-hydroxy-5-(4-nitrophenyl)-pentanoyl-L-isoleucine methyl ester

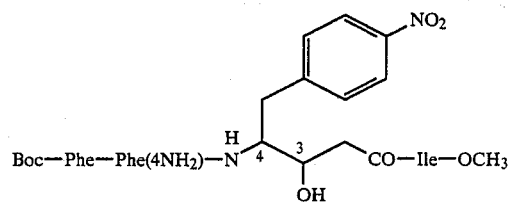

55 mg (0.68 mmol) of the Fmoc-protected compound of Example 23 is stirred in a mixture of 1.5 ml of piperidine and 6 ml of THF at room temperature for 4 hours. The solvents are stripped off in vacuo and the crude product is purified by chromatography on silica gel with CH$_2$Cl$_2$/CH$_3$OH 9:1.

Yield: 30.9 mg (57% of theory)
Melting point: —(amorphous)
TLC system I: R$_f$=0.65
TLC system II: R$_f$=0.38
(+)FAB-MS: m/z 924 ((M+C$_7$H$_5$NO$_3$)—H$_2$O)

EXAMPLE 25

N-tert.-Butoxycarbonyl-L-(1-naphthyl)alanyl-L-{4-N(9-fluorenylmethoxycarbonyl)aminophenyl}alanyl-4S-amino-3S-hydroxy-5-(4-nitrophenyl)pentanoyl-L-isoleucine methyl ester

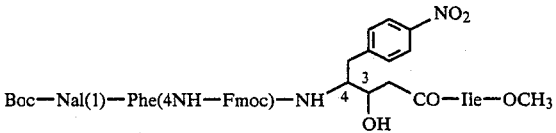

The title compound is prepared by the propane-phosphonic acid anhydride method analogously to Example 37 and 47 from 139 mg (0.137 mmol) of Example 22 and tert.-butoxycarbonyl-L-(1-naphthyl)alanine. The crude product (90 mg) is crystallized from ether/hexane.

Yield: 75 mg (40% of theory)
Melting point: —(amorphous)

TLC system I: R$_f$=0.5
HPLC value; system I: R$_t$=11.51 minutes.
(+)FAB-MS: m/z 1063 (M+H); m/z 963

EXAMPLE 26

N-tert.-Butoxycarbonyl-L-(1-naphthyl)alanyl-L-(4-aminophenyl)alanyl-4S-amino-3S-hydroxy-5-(4-nitrophenyl)pentanoyl-L-isoleucine methyl ester

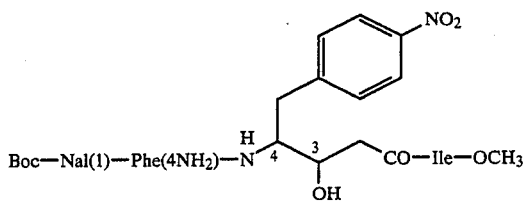

The title compound is prepared from 52 mg (0.05 mmol) of Example 25 analogously to Example 24, by splitting off the Fmoc protective group. The crude product is crystallized from ether/hexane.

Yield: 23 mg (56% of theory)
Melting point: —(amorphous)
TLC system I: R$_f$=0.60
(+)FAB-MS: m/z 841 (M+H): m/z 741

EXAMPLE 27

N-tert.-Butoxycarbonyl-L-phenylalanyl-L-histidyl-4S-amino-3S-hydroxy-5-(4-aminophenyl)pentanoyl-L-isoleucine methyl ester

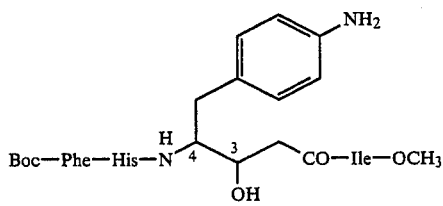

66 mg (0.086 mmol) of the corresponding nitro compound (Example 12) are dissolved in 7.5 ml of ethyl acetate/methanol 1:2. 62 mg of 10% strength palladium-on-charcoal are added and the stirred suspension is hydrogenated under normal pressure for 1 hour. The catalyst is filtered off and concentrated to dryness in vacuo.

Yield: 57 mg (90% of theory)
Melting point: —(amorphous)
TLC system I: R$_f$=0.47
HPLC value; system I: R$_t$=3.98 minutes
(+)FAB-MS: m/z 736 (M+H); m/z 869 ((M+C$_7$H$_5$NO$_3$)—H$_2$O).

EXAMPLE 28

N-tert.-Butoxycarbonyl-L-phenylalanyl-L-phenylalanyl-4-S-amino-3S-hydroxy-5-(4-aminophenyl)pentanoyl-L-isoleucine methyl ester

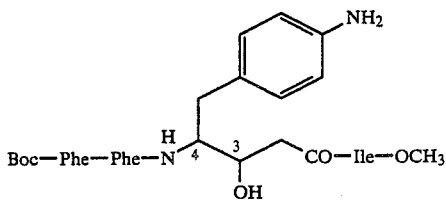

The title compound is prepared from 52 mg (0.067 mmol) of Example 13 by catalytic hydrogenation (as described in Example 27).

Yield: 43 mg (86% of theory)
Melting point: —(amorphous)
TLC system I: R$_f$=0.53
HPLC value; system I: R$_t$=7.32 minutes
(+)FAB-MS: m/z 869 ((M+C$_7$H$_5$NO$_3$)—H$_2$O), m/z 769

EXAMPLE 29

N-tert.-Butoxycarbonyl-L-phenylalanyl-L-histidyl-4S-amino-3R-hydroxy-5-(4-aminophenyl)pentanoyl-L-isoleucine methyl ester

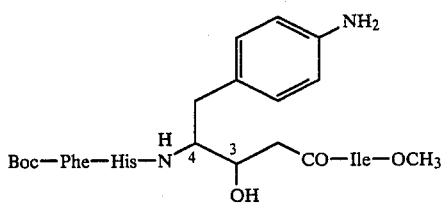

The title compound is prepared from 177 mg (0.23 mmol) of Example 17 by catalytic hydrogenation (as described in Example 27).

Yield: 151.6 mg (90% of theory)
Melting point: —(amorphous)
TLC system I: R$_f$=0.48
HPLC value; system I: R$_t$=3.94 minutes

EXAMPLE 30

N-tert.-Butoxycarbonyl-L-phenylalanyl-4S-amino-3S-hydroxy-5-(4-nitrophenyl)pentanoyl-L-isoleucine methyl ester

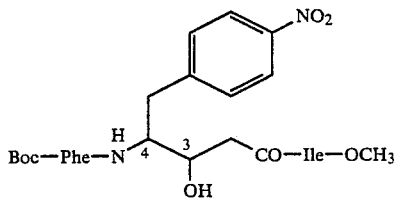

The title compound is prepared by the propanephosphonic acid anhydride method (as described in Example 37 and 47) from 0.6 g (1.4 mmol) of Example 11 and 420 mg (1.6 mmol) of N-tert.-butoxycarbonyl-L-phenylalanine.

Yield: 690 mg (78% of theory)
Melting point: —(amorphous)
TLC system I: R$_f$=0.86
HPLC value; system II: R$_t$=10.55 minutes
(+)FAB-MS: m/z 629 (M+H); m/z 573; m/z 529

EXAMPLE 31

L-(2-Nitrophenyl)alanine methyl ester hydrochloride

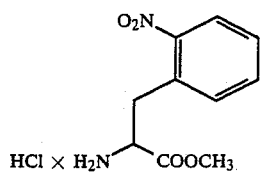

The title compound is prepared analogously to Example 2 from 30.3 g (0.12 mol) of L-(2-nitrophenyl)alanine hydrochloride (Alvie L. Davies et al., J. Med. Chem. 15, 325–327 (1972).

Yield: 15.6 g (50% of theory)
TLC system I: $R_f=0.60$
TLC system VII: $R_f=0.76$
$^1$H-NMR (DMSO, 250 MHz); $\delta=8.95$ (b, 3H); 8.04 (m, 1H); 7.50–7.75 (m, 3H); 4.20 (m, 1H); 3.60 (s, 3H); 3.48 (m, 2H).

EXAMPLE 32

N-tert.-Butoxycarbonyl-L-(2-nitrophenyl)alanine methyl ester

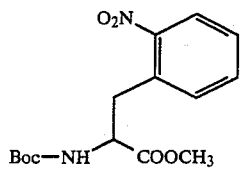

The title compound is prepared analogously to Example 3 from 10.5 g (0.04 mol) of Example 31.

Yield: 11.2 g (87.6% of theory)
TLC system I: $R_f=0.72$
TLC system II: $R_f=0.75$
$^1$H-NMR (CDCl$_3$, 250 MHz): $\delta=7.90$ (m, 1H); 7.30–7.75 (m, 3H); 5.20 (d, 1H); 4.65 (m, 1H); 3.72 (s, 3H); 3.52 (m, 1H); 3.26 (m, 1H); 1.45 (s, 9H).

EXAMPLE 33

N-tert.-Butoxycarbonyl-L-(2-nitrophenyl)alaninol

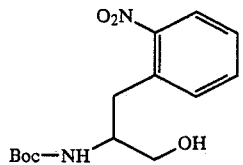

The title compound is prepared analogously to Example 4 from 17.9 g (55 mmol) of Example 32.

Yield: 14.3 g (87.7% of theory)
TLC system II: $R_f=0.32$
$^1$H-NMR (200 MHz, CDCl$_3$) $\delta=7.90$ (m, 1H), 7.35–7.62 (m, 3H); 5.12 (d, 1H); 4.04 (m, 1H); 3.60 (m, 2H); 2.95–3.30 (m, 2H); 2.67 (broad, 1H); 1.33 (s, 9H).
(+)FAB-MS: m/z 297 (M+H)

EXAMPLE 34

N-tert.-Butoxycarbonyl-L-(2-nitrophenyl)alaninal

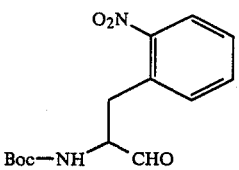

The title compound is prepared analogously to Example 5 from 13.5 g (0.045 mol) of Example 33.

Yield: 11.3 g (85% of theory)
$^1$H-NMR (200 MHz, CDCl$_3$): $\delta=9.69$ (s, 1H); 8.04 (m, 1H); 7.35–7.62 (m, 3H); 5.40 (d, 1H); 4.59 (m, 1H); 3.63 (dd, 1H); 3.12 (dd, 1H); 1.35 (s, 9H).

EXAMPLE 35

Ethyl N-tert.-butoxycarbonyl-4S-amino-3RS-hydroxy-5-(2-nitrophenyl)-pentanoate

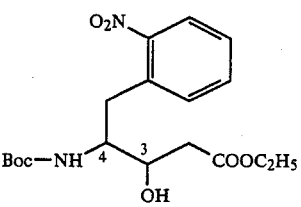

The title compound is prepared analogously to Example 6 from 11.3 g (38.4 mmol) of N-tert.-butoxycarbonyl-L(2-nitrophenyl)-alaninal (Example 34) and lithium salt of acetic acid ethyl ester. Crude yield: 12.3 g (83.3% of theory) The stereoisomers formed, that is to say ethyl N-tert.-butoxycarbonyl-4S-amino-3R and 3S-hydroxy-5-(O-2-nitrophenyl)pentanoate are not resolved completely by column chromatography analogously to Example 7 and 8, so that the subsequent hydrolysis is carried out analogously to Example 9 with the diastereomer mixture.

TLC system VI: $R_f=0.12–0.18$
HPLC value; system I: diastereomer A, $R_t=4.22$ minutes; diastereomer B, $R_t=4.44$ minutes.
$^1$H-NMR (200 MHz, CDCl$_3$): =7.95 (m, 1H); 7.15–7.60 (m, 3H); 5.13 (d+d, 1H); 4.20 (m, 3H); 3.98 (m, 1H); 4.80 (broad, 1H); 2.50–3.40 (m, 4H); 1.20–1.35 (m, 12H).
(+)FAB-MS: m/z 383 (M+H); m/z 327; m/z 283

EXAMPLE 36

N-tert.-Butoxycarbonyl-4S-amino-3RS-hydroxy-5-(2-nitrophenyl)-pentanoic acid

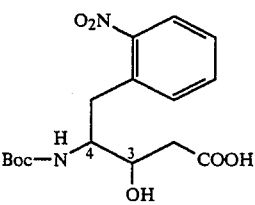

The title compound is prepared analogously to Example 9 from 2.25 g (5.9 mmol) of ethyl N-tert.-butoxycarbonyl-4S-amino-3RS-hydroxy-5-(2-nitrophenyl)-pentanoate (Example 35).

Yield: 0.88 g (42% of theory)

Melting point: —(amorphous)
(+)FAB-MS: m/z 355 (M+H); m/z 299; m/z 255

EXAMPLE 37

N-tert.-Butoxycarbonyl-4S-amino-3RS-hydroxy-5-(2-nitrophenyl)pentanoyl-L-isoleucine methyl ester

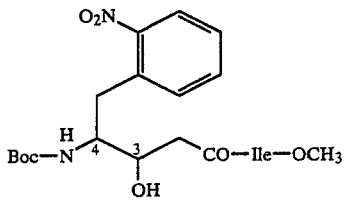

1.1 g (=1.53 ml) of triethylamine are added to a suspension of 0.53 g (3 mmol) of isoleucine methyl ester hydrochloride and 0.7 g (2 mmol) of N-tert.-butoxycarbonyl-4S-amino-3RS-hydroxy-5-(2-nitrophenyl)pentanoic acid (Example 36) in 10 ml of methylene chloride. The mixture is stirred for 10 minutes and cooled to −20° C. (dry ice/acetone), and 1.43 ml (=2.2 mmol) of a 50% strength solution of propanephosphonic acid anhydride in methylene chloride are added dropwise at this temperature. The batch is stirred at −20° C. for 1 hour and at room temperature overnight. The reaction mixture is extracted by shaking in succession 3 times with 10 ml of 5% strength sodium bicarbonate solution each time, 3 times with 10 ml of 1N hydrochloric acid each time, once with 10 ml of 5% strength sodium bicarbonate solution and finally once with 10 ml of saturated sodium chloride solution. The organic phase is dried over magnesium sulphate and concentrated in vacuo. The product is obtained as an amorphous foam by drying under a high vacuum.

Yield: 0.75 g (78% of theory)

$^1$H-NMR (300 MHz, DMSO): δ=8.13 (d, 1H); 7.89 (m, 1H); 7.37–7.68 (m, 3H); 6.54 (d) and 6.44 (d): together 1H; 5.04 (d) and 4.88 (d): together 1H; 4.23 (m, 1H); 3.85 (m, 2H); 3.61 (s) and 3.62 (s): together 3H; 3.28 (m, 2H); 2.10–2.85 (m, 2H); 1.73 (m, 1H); 1.08–1.46 (m, 2H); 1.18 (s) and 1.22 (s): together 9H; 0.83 (m, 6H).

(+)FAB-MS: m/z 482 (M+H); m/z 504 (M+Na); m/z 426; m/z 382.

HPLC values; system I: Diastereomer A (3R,4S in respect of the (2-nitrophenyl)pentanoyl portion) R$_t$=5.70 diastereomer B (3S,4S in respect of the (2-nitrophenyl)pentanoyl portion) R$_t$=6.32

EXAMPLE 38 AND EXAMPLE 39

N-tert.-Butoxycarbonyl-4S-amino-3R-hydroxy-5-(2-nitrophenyl)pentanoyl-L-isoleucine methyl ester (Example 38) and N-tert.-butoxycarbonyl-(4S-amino-3S-hydroxy-5-(2-nitrophenyl)pentanoyl-L-isoleucine methyl ester (Example 39)

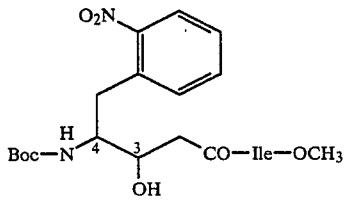

The two compounds Example 38 and 39 can be obtained as pure isomers by isocratic preparative medium pressure chromatography of the diastereomer mixture from Example 37 over a Merck Lobar prepacked column RP8, size C (440-37), Lichroprep ®RP-8 40-63 mm, catalogue number: 10629 with the mobile phase mixture water/acetonitrile 1:1.

HPLC values; system I: Example 38: R$_t$=5.70; Example 39: R$_t$=6.32.

EXAMPLE 40 AND EXAMPLE 41

N-tert.-Butoxycarbonyl-L-phenylalanyl-L-histidyl-4S-amino-3RS-hydroxy-5-(2-nitrophenyl)pentanoyl-L-isoleucine methyl ester (Example 40) and N-tert.-butoxycarbonyl-L-phenylalanyl-L-histidyl-4S-amino-3S-hydroxy-5-(2-nitrophenyl)pentanoyl-L-isoleucine methyl ester (Example 41)

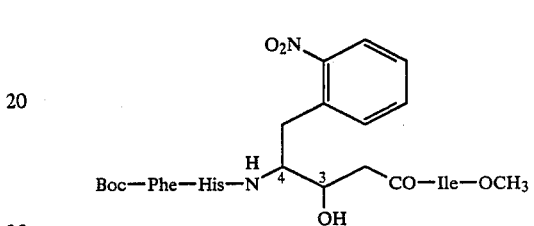

300 mg (0.63 mmol) of N-tert.-butoxycarbonyl-4S-amino-3RS-hydroxy-5-(2-nitrophenyl)pentanoyl-L-isoleucine methyl ester (Example 37) are stirred with 10 ml of 4N HCl in dioxane, in order to split off the tert.-butoxycarbonyl protective group, and the mixture is concentrated and the residue is dired under a high vacuum for 1 hour. The resulting dihydrochloride is then coupled with Boc-Phe-His-OH (Example 48) by the DCC/HOBT method as described under Example 12 to give the title compound.

Yield: 480 mg

Medium pressure chromatography of the crude product on a Merck Lobar prepacked column size B(310-25) SiO$_2$-LiChroprep ®Si 60 (40–63 μm), Cat. No. 10401, with the mobile phase mixture CH$_2$Cl$_2$/CH$_3$OH 9:1 gives the two title compounds in a pure form.

Example 41, elutes first in the above chromatography, yield: 91 mg
(+)FAB-MS: m/z 766 (M+H)
HPLC value; system I: R$_t$=5.47
Example 40.) Yield: 160 mg
(+)FAB-MS: m/z 766 (M+H)
HPLC value; system I: R$_t$=5.47 and ~5.20

EXAMPLE 42

N-tert.-Butoxycarbonyl-L-phenylalanyl-L-histidyl-4S-amino-3RS-hydroxy-5-(2-aminophenyl)pentanoyl-L-isoleucine methyl ester

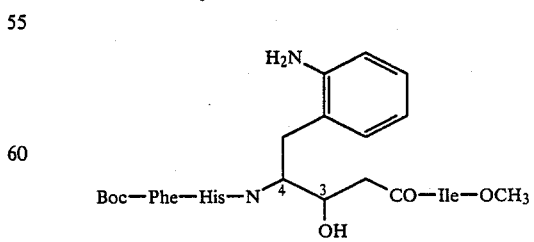

74 mg (0.1 mmol) of the corresponding 2-nitro compound (Example 40) are dissolved in 10 ml of methanol, 55 mg of 10% strength palladium-on-charcoal are added and hydrogenation is carried out under normal pressure for one hour. After TLC control, the catalyst is filtered off and the solvent is concentrated.

Yield: 47 mg (64% of theory)

Melting point: —(amorphous, diastereomer mixture)

HPLC values; system I: 4.09 minutes and 4.43 minutes

EXAMPLE 43

N-Benzoyl-D,L-(1-triazolyl)alanyl-4S-amino-3S-hydroxy-5-(4-nitrophenyl)pentanoyl-L-isoleucine methyl ester

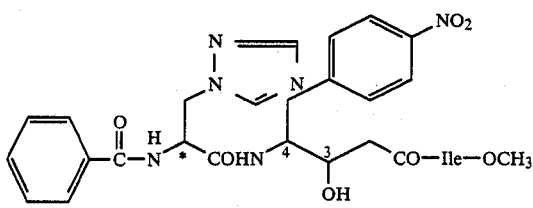

The title compound is prepared from 111 mg (0.26 mmol) of Example 12 and 80.6 mg (0.31 mmol) of N-benzoyl-DL-(1-triazolyl)-alanine by the DCC/HOBT method (as described in Example 12).

Crude yield: 240 mg

TLC system I: $R_f=0.57$

HPLC value; system I: $R_t=2.88$ minutes and 3.00 minutes (+)FAB-MS: m/z 624 (M+H)

The entire crude yield from Example 43 is further processed to Example 44 and Example 45 Example 44 being the diastereomer of Example 45, but the exact configurations on the asymmetric center of the (1-triazolyl)alanine not being determined.

EXAMPLE 44 AND EXAMPLE 45

N-Benzoyl-D-(1-triazolyl)alaninyl-4S-amino-3S-hydroxy-5-(4-nitrophenyl)pentanoyl-L-isoleucine methyl ester (Example 44) and
N-benzoyl-L-(1-triazolyl)alaninyl-4S-amino-3S-hydroxy-5-(4-nitrophenyl)pentanoyl-L-isoleucine methyl ester (Example 45)

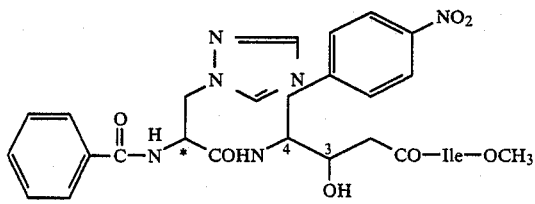

The crude yield from Example 43 is purified by medium pressure chromatography over a Merck Lobar prepacked column Lichroprep ®RP-8 (40–63 μm), size B, 310–297 Cat. No. 11804, with the mobile phase mixture acetonitrile/water 50:50. The flow rate is 15 ml/minute and the fraction size is 15 ml. The individual fractions are combined according to the HPLC control. After lyophilization, the title compounds are obtained in an extremely pure form.

Yield: Fraction 13,14: 18.5 mg=Example 44.); Fraction 15: 34.2 mg=D,L mixture; (=Example 43.).

Fraction 16,17: 31.7 mg=Example 45.)

Example 44.):

Yield: 18.5 mg

HPLC value; system I: $R_t=2.87$ minutes (+)FAB-MS: m/z 624 (M+H)

Example 45.):

Yield: 31.7 mg

HPLC value; system I: $R_t=2.99$ minutes (+)FAB-MS: m/z 624 (M+H)

EXAMPLE 46

N-Benzoyl-D,L-(1-triazolyl)alanyl-4S-amino-3S-hydroxy-5-(4-aminophenyl)pentanoyl-L-isoleucine methyl ester

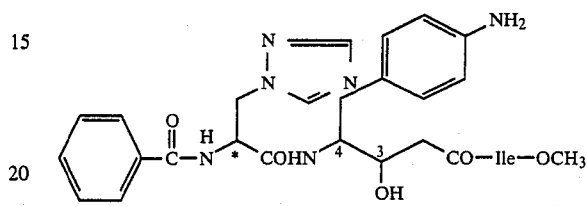

The title compound is obtained by catalytic hydrogenation (as described in Example 27) of the corresponding nitro compound (D,L-mixture from Example 44 and 45 fraction 15, 31.2 mg, 50 mmol). The crude product is recrystallized from ethyl acetate.

Yield: 27.1 mg (91%. of theory)

Melting point: —(amorphous)

TLC system I: $R_f=0.47$ and $R_f=0.50$

HPLC value; system I: $R_t=2.01$ minutes, cannot be differentiated.

(+)FAB-MS: m/z 594 (M+H)

EXAMPLE 47

N-tert.-Butoxycarbonyl-L-phenylalanyl-L-histidine methyl ester

Boc-Phe-His-OCH₃

43.73 g (164 mmol) of N-tert.-butoxycarbonyl-L-phenylalanine and 34.5 g (142 mmol) of L-histidine methyl ester dihydrochloride are taken in 400 ml of methylene chloride. 100 g (1 mol) of triethylamine are added at −20° C. (acetone/dry ice bath), while stirring. 111 ml (0.171 mol) of propanephosphonic acid anhydride solution (50% strength in methylene chloride) are now added dropwise to the cooled mixture. The mixture is allowed to warm to room temperature overnight. The solvent is stripped off and the crude product is taken up in 500 ml of ethyl acetate. The organic phase is washed 4 times with 200 ml of saturated sodium bicarbonate solution each time, 3 times with 0.1N hydrochloric acid and once with saturated sodium chloride solution, dried over magnesium sulphate and concentrated in vacuo.

Yield: 29.2 g (49% of theory)

Melting point: —(amorphous)

TLC system I: $R_f=0.50$

HPLC value; system I: $R_t=10.68$ minutes; system II: $R_t=16.73$ minutes.

EXAMPLE 48

N-tert.-Butoxycarbonyl-L-phenylalanyl-L-histidine

Boc-Phe-His-OH

The title compound is prepared from Example 47 by alkaline hydrolysis. For this, 4.16 g (10 mmol) of the methyl ester are dissolved in 200 ml of dioxane and 20 ml of 1N NaOH. The solution is stirred at room temperature for 2.5 days, the dioxane is stripped off on a rotary evaporator, the batch is neutralized with 20 ml of 1N HCl and the solid which has precipitated is filtered off with suction. The product is rinsed with water and dried over phosphorus pentoxide.

Yield: 2.7 g (67% of theory)
Melting point: —(amorphous)
TLC system I: $R_f=0.10$

EXAMPLE 49

D,L-(1-Triazolyl)alanine

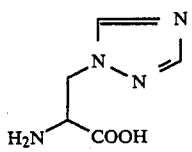

0.6 g (0.0026 mol) of sodium is dissolved in 150 ml of methanol. 8.5 g (0.123 mol) of triazole are added. 8.5 g (0.123 mol) of N-acetyl-dehydroalanine ethyl ester (H. Hellmann et al., Chem. Ber. 91, 2427-2431 (1958), dissolved in 150 ml of ethanol, are added dropwise to the stirred mixture. The mixture is stirred under reflux for a further hour and the solvents are then evaporated.

To split off the protective groups, the residue of N-acetyl-D,L-(1-triazolyl)alanine ethyl ester is boiled in half-concentrated hydrochloric acid for 8 hours. The hydrochloric acid is evaporated off. The crude product is evaporated on a rotary evaporator, first 3 times with water and then twice more with toluene, to remove the excess hydrochloric acid. The crude D,L-(1-triazolyl)alanine containing hydrochloric acid is dissolved in hot water. The pH value of the solution is brought to pH 7 with diethylamine. After cooling, the title compound which has precipitated in the form of white crystals is filtered off with suction, rinsed with methanol and dried.

Yield: 7.5 g (48% of theory)
Melting point: 250° C. (decomposition)

| Analysis: | C | H | N | O |
|---|---|---|---|---|
| calculated: | 38.4 | 5.2 | 35.9 | — |
| found: | 38.4 | 5.0 | 35.8 | — |

EXAMPLE 50

N-Benzoyl-D,L-(1-triazolyl)alanine

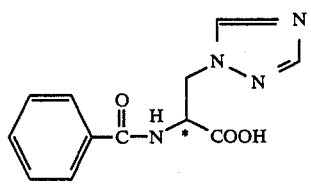

7.8 g (0.05 mol) of D,L-(1-triazolyl)alanine are dissolved in a mixture of 2 g of sodium hydroxide and 23 ml of water. 7 g (0.05 mol) of benzoyl chloride are added dropwise to the stirred mixture at a temperature of less than 30° C. (cooling with ice), and the mixture is subsequently stirred at this temperature for a further 4 hours and left to stand overnight at room temperature. The crude product which has precipitated is filtered off with suction and rinsed with cold water. The residue is extracted by boiling with acetone and the product is filtered off hot with suction, rinsed with acetone and dried.

Yield: 3.3 g (25.4% of theory)
Melting point: 216°-220° C.
MS: m/z 260; m/z 215; m/z 191; m/z 147; m/z 105 (base peak); m/z 83; m/z 77; m/z 51.

EXAMPLE 51

L-(3-Nitrophenyl)alanine methyl ester hydrochloride

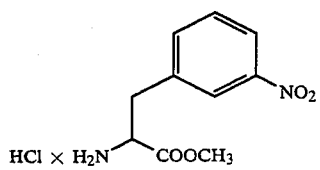

The title compound is prepared analogously to Example 2 from 134 g (0.57 mol) of L-(3-nitrophenyl)alanine hydrochloride.

Yield: 133.6 g (90% of theory)
TLC system I: $R_f=0.58$
$^1$H-NMR (DMSO, 250 MHz): $\delta=8.88$ (b, 3H); 8.16 (m, 2H); 7.07-7.82 (m, 2H); 4.40 (m, 1H); 3.70 (s, 3H); 3.34 (m, 2H).

EXAMPLE 52

N-tert.-Butoxycarbonyl-L-(3-nitrophenyl)alanine methyl

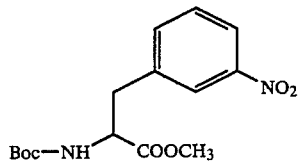

The title compound is prepared analogously to Example 3 from 93.5 g (0.36 mol) of L-(3-nitrophenyl)-methyl ester hydrochloride (Example 51).

Yield: 93.6 g (82.4% of theory)
TLC system I: $R_f=0.32$

EXAMPLE 53

N-tert.-Butoxycarbonyl-L-(3-nitrophenyl)alaninol

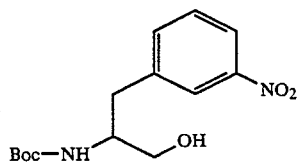

The title compound is prepared analogously to Example 4 from 90 g (0.27 mol) of N-tert.-butoxycarbonyl-L-(3-nitrophenyl)alanine methyl ester (Example 52).

Yield: 60 g (73% of theory)
TLC system I: $R_f=0.68$
TLC system II: $R_f=0.78$

TLC system IV: R$_f$=0.18

$^1$H-NMR (CDCl$_3$, 250 MHz): δ=8.05 (m, 2H); 7.55 (m, 1H); 7.41 (m, 1H); 4.98 (b, 1H); 3.84 (b, 1H); 3.59 (m, 2H); 2.92 (m, 2H); 1.33 (s, 9H).

EXAMPLE 54

N-tert.-Butoxycarbonyl-L-(3-nitrophenyl)alaninal

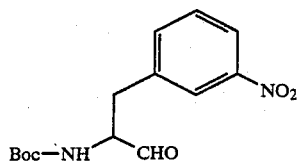

The title compound is prepared analogously to Example 5 from 30 g (0.1 mol) of N-tert.-butoxycarbonyl-L-(3-nitrophenyl)alaninol (Example 53).
Yield: 26.1 g (87.6% of theory)
TLC system II: R$_f$=0.72
TLC system VI: R$_f$=0.29

EXAMPLE 55

N-tert.-Butoxycarbonyl-4S-amino-3RS-hydroxy-5-(3-nitrophenyl)pentanoic acid ethyl ester

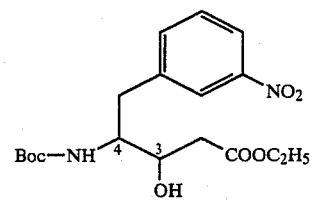

The title compound is prepared analogously to Example 6 from 26.1 g (88.7 mmol) of N-tert-butoxycarbonyl-yl-L-(3-nitrophenyl)-alaninal (Example 54) and lithium salt of acetic acid ethyl ester.
Yield: 27.3 g (80% of theory)
(+)FAB-MS: m/z 383 (M+H); m/z 327; m/z 283

EXAMPLE 56 AND EXAMPLE 57

N-tert.-Butoxycarbonyl-4S-amino-3S-hydroxy-5-(3-nitrophenyl)pentanoic acid ethyl ester and N-tert.-butoxycarbonyl-4S-amino-3R-hydroxy-5-(3-nitrophenyl)pentanoic acid ethyl ester

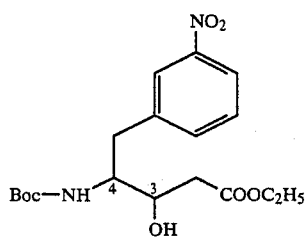

The two diastereomeric product are resolved by column chromatography of the mixture of ethyl N-tert.-butoxycarbonyl-4S-amino-3RS-hydroxy-5-(3-nitrophenyl)pentanoic acid ethyl ester (Example 55) under the conditions described in Example 7 and 8.

The 3S,4S-isomer (Example 56) elutes first, followed by the 3R,4S-isomer (Example 57)

EXAMPLE No. 56

$^1$H-NMR (CDCl$_3$, 250 MHz): δ=8.09 (m, 2H); 7.6 (m, 1H); 7.46 (m, 1H); 4.98 (d, 1H); 4.16 (q, 2H); 3.98 (m, 1H); 3.77 (m, 1H); 3.61 (b, 1H); 3.02 (m, 2H); 2.61 (m, 1H); 2.40 (m, 1H); 1.36 (S, 9H); 1.24 (t, 3H).
TLC system VI: R$_f$=0.25
HPLC value, system II: R$_f$=5.31 minutes

EXAMPLE 57

$^1$H-NMR (CDCl$_3$, 250 MHz): δ=8.09 (m, 2H); 7.59 (m, 1H); 7.46 (m, 1H); 4.66 (d, 1h); 4.18 (q, 2H); 4.01 (m, 1H); 3.84 (m, 1H); 3.59 (s, broad) 1H); 3.13 (m, 1h); 2.88 (m, 1H); 2.46–2.78 (m, 2H); 1.29 (s, 9H); 1.27 (t, 3H).
TLC system VI: R$_f$=0.22
HPLC value; system II: R$_f$=4.73 minutes

EXAMPLE 58

N-tert.-Butoxycarbonyl-4S-amino-3RS-hydroxy-5-(3-nitrophenyl)pentanoic acid

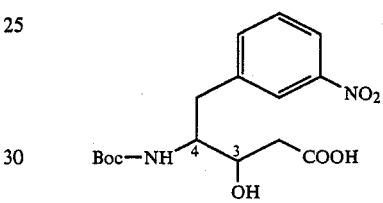

The title compound is prepared analogously to Example 9 from 20.2 g (53 mmol) of the crude mixture of ethyl N-tert.-butoxycarbonyl-4S-amino-3RS-hydroxy-5-(3-nitrophenyl)-pentanoate (Example 55).
Yield: 8.75 g (45% of theory)
TLC system I: R$_f$=0.42
TLC system II: R$_f$=0.20

EXAMPLE 59

N-tert.-Butoxycarbonyl-4S-amino-3RS-hydroxy-5-(3-nitrophenyl)pentanoyl-L-isoleucine methyl ester

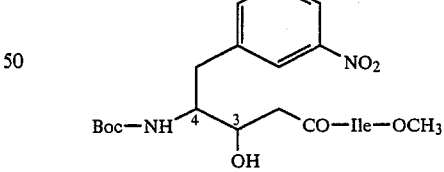

The title compound is prepared analogously to Example 37 from 7.1 g (20 mmol) of N-tert.-butoxycarbonyl-4S-amino-3RS-hydroxy-5-(3-nitrophenyl)pentanoic acid (Example 58) and isoleucine methyl ester hydrochloride.
Yield: 9 g (96% of theory)
TLC system II: R$_f$=0.61 (isomer A); R$_f$=0.50 (isomer B).

EXAMPLE 60

4S-Amino-3RS-hydroxy-5-(3-nitrophenyl)pentanoyl-L-isoleucine methyl ester hydrochloride

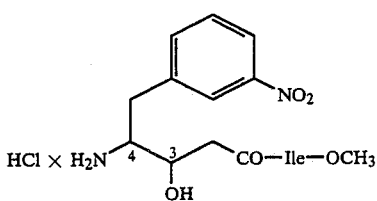

The title compound is prepared analogously to Example 11 from 8.9 g (18.5 mmol) of N-tert.-butoxycarbonyl-4S-amino-3RS-hydroxy-5-(3-nitrophenyl)pentanoyl-L-isoleucine methyl ester (Example 59).
Yield: 7.7 g (100% of theory)

EXAMPLE 61

N-tert.-Butoxycarbonyl-L-phenylalanyl-L-histidyl-4S-amino-3RS-hydroxy-5-(3-nitrophenyl)pentanoyl-L-isoleucine methyl ester

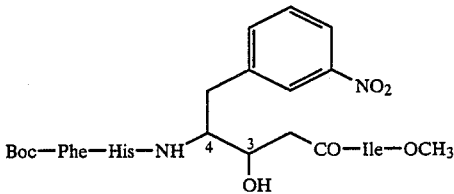

The title compound is prepared from 4S-amino-3RS-hydroxy-5-(3-nitrophenyl)pentanoyl-L-isoleucine methyl ester hydrochloride (Example 60) and Boc-Phe-His-OH (Example 48) analogously to Example 12.
(+)FAB-MS: m/z 766(M+H)
TLC system I: $R_f=0.37$
HPLC value, system II: $R_t=7.00$ minutes (isomer A); $R_t=7.10$ minutes (isomer B).

EXAMPLE 62

N-tert.-Butoxycarbonyl-L-(4-nitrophenyl)-alanyl-N'-methoxy)methylamide

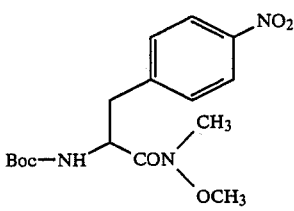

The title compound is prepared by the PPA coupling method described under Example 47 from 80 g (0.26 mol) of N-tert.-butoxycarbonyl-L-(4-nitrophenyl)alanine (A. V. Schally et al., J. Med. Chem. 16, 828 (1973)) and 22.6 g (0.24 mol) of N,O-dimethylhydroxylamine hydrochloride (Ega).
Yield: 78.2 g (95% of theory)
$^1$H-NMR (CDCl$_3$, 200 MHz): $\delta=8.14$ (d, 2H); 7.34 (d, 2H); 5.22 (d, 1H); 4.95 (m, 1H); 3.72 (s, 3H); 3.19 (s, 3H); 3.15 (m, 1H); 2.95 (m, 1H); 1.36 (s, 9H).
TLC system I: $R_f=0.76$
TLC system II: $R_f=0.87$

EXAMPLE 63

(2-Ethoxy)ethyl N-tert-butoxycarbonyl-4S-amino-3RS-hydroxy-5-(4-nitrophenyl)-pentanoate

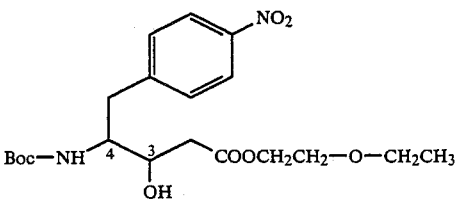

The title compound is prepared analogously to Example 6 from 9 g (31 mmol) of N-tert.-butoxycarbonyl-L-(4-nitrophenyl)alaninal (Example 5) and the lithium salt of acetic acid (2-ethoxy)ethyl ester.
Crude yield: 12.2 (93% of theory)
TLC system II: $R_f=0.50$ (isomers cannot be differentiated)
HPLC value, system II: $R_f=3.93$ (isomer A); $R_f=4.35$ (isomer B); in the ratio 1.1:1

EXAMPLE 64

N-tert.-Butoxycarbonyl-4S-amino-3RS-hydroxy-5-(4-nitrophenyl)-pentanoic acid

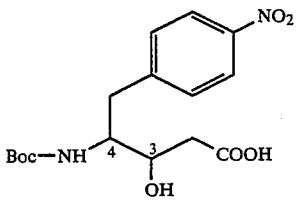

The title compound is prepared analogously to Example 9 from 6.7 g (16 mmol) of ethoxyethyl N-tert.-butoxycarbonyl-4S-amino-3RS-hydroxy-5-(4-nitrophenyl)pentanoate (Example 63).
Yield: 4 g (71.5% of theory)

EXAMPLE 65

N-tert.-Butoxycarbonyl-L-leucyl-benzylamide

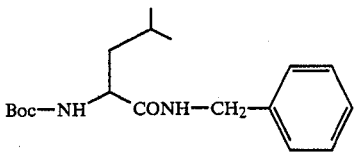

The title compound is prepared by the PPA coupling method described in Example 37 and 47 from 46 g (0.2 mol) of N-tert.-butoxycarbonyl-L-leucine and 24 ml (0.22 mol) of benzylamine.
Yield: 32.1 g (53% of theory)
$^1$H-NMR (DMSO, 250 MHz): $\delta=8.32$ (m, 1H); 7.22 (m, 5H); 6.88 (d, 1H); 4.29 (d, 2H); 4.02 (m, 1h); 1.30-1.70 (m, 3H); 1.38 (s, 9H); 0.86 (m, 6H).
TLC system I: $R_f=0.73$

EXAMPLE 66

L-leucyl-benzylamide hydrochloride

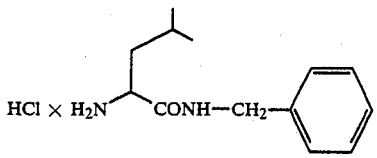

The title compound is prepared from 32 g (0.1 mol) of N-tert.-butoxycarbonyl-L-leucyl-benzylamide (Example 65) by splitting off the tert.-butoxycarbonyl protective group (analogously to Example 11).

Yield: 23.6 g (92% of theory)
TLC system XI: $R_f=0.75$

EXAMPLE 67

N-tert.-Butoxycarbonyl-4S-amino-3RS-hydroxy-5-(4-nitrophenyl)pentanoyl-L-leucyl-benzylamide

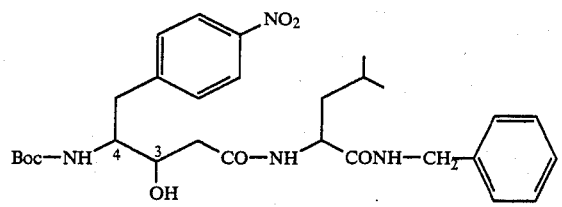

The title compound is prepared by the PPA method (analogously to Example 47) from 6.1 g (17.3 mmol) of N-tert.-butoxycarbonyl-4S-amino-3RS-hydroxy-5-(4-nitrophenyl)-pentanoic (Example 64) and 5.3 g (20.8 mmol) of L-leucyl-benzylamide hydrochloride (Example 66).

Yield: 4.2 g (44% of theory)
(+)FAB-MS: m/z 557 (M+H); m/z 579 (M+Na)
TLC system XI: $R_f=0.67$
HPLC value, system II: $R_t=6.7$ minutes (isomer A); $R_t=7.7$ minutes (isomer B).

EXAMPLE 68

4S-Amino-3RS-hydroxy-5-(4-nitrophenyl)pentanoyl-L-leucylbenzylamide hydrochloride

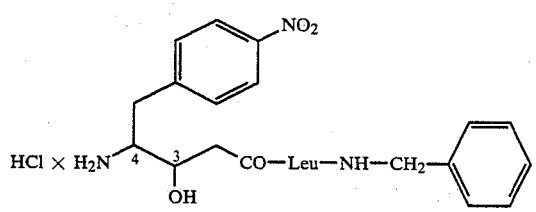

The title compound is obtained from 4.2 g (7.6 mmol) of N-tert.-butoxycarbonyl-4S-amino-3RS-hydroxy-5-(4-nitrophenyl)pentanoyl-L-leucyl-benzylamide (Example 67) by splitting off the butoxycarbonyl protective group analogously to Example 11.

Yield: 4 g (107% of theory, hygroscopic)
TLC system XI: $R_f=0.5$
HPLC value, system II: $R_t=7.61$ minutes (isomers cannot be differentiated)

EXAMPLE 69

N-tert.-Butoxycarbonyl-L-phenylalanyl-L-histidyl-4S-amino-3RS-hydroxy-5-(4-nitrophenyl)pentanoyl-L-leucyl-benzylamide

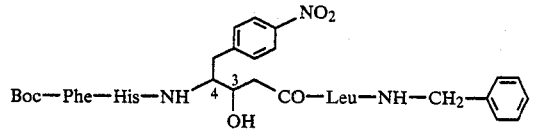

The title compound is prepared analogously to Example 12 from N-tert.-butoxycarbonyl-L-phenylalanyl-L-histidine (Example 48) and 4S-amino-3RS-hydroxy-5-(4-nitrophenyl)pentanoyl-L-leucyl-benzylamide hydrochloride (Example 68).

(+)FAB-MS: m/z 841 (M+H)
TLC system XI: $R_f=0.39$
HPLC value, system II: $R_t=8.5$ minutes, both isomers (broad peak).

EXAMPLE 70

N-Benzyloxycarbonyl-L-phenylalanyl-L-histidyl-4S-amino-3RS-hydroxy-5-(4-nitrophenyl)pentanoyl-L-leucyl-benzylamide

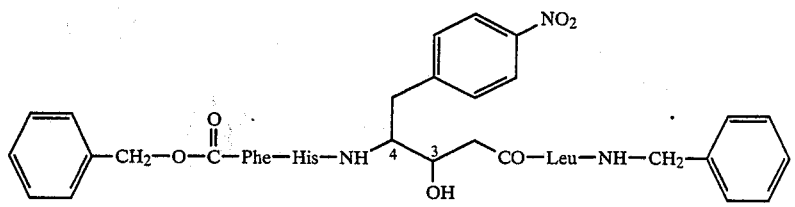

The title compound is prepared analogously to Example 12 from N-benzyloxycarbonyl-L-phenylalanyl-L-histidine (obtainable by coupling Z-L-Phe and His-OCH$_3$—analogously to Example 47—and subsequent hydrolysis of the product (analogously to Example 48)) and 4S-amino-3RS-hydroxy-5-(4-nitrophenyl)-pentanoyl-L-leucyl-benzylamide hydrochloride (Example 68).

(+)FAB-MS: m/z 875 (M+H), m/z 897 (M+Na)
TLC system XI: $R_f=0.45$
HPLC value, system II: $R_t=10.3$ minutes, both isomers (broad peak).

EXAMPLE 71

N$\alpha$,N$\tau$-di-tert.-Butoxycarbonyl-L-histidyl-4S-amino-3S-hydroxy-5-(4-nitrophenyl)pentanoyl-L-isoleucine-methyl ester

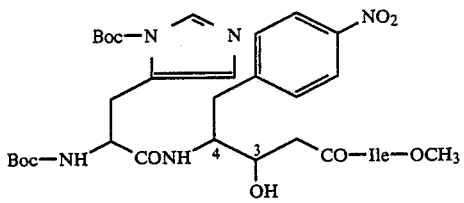

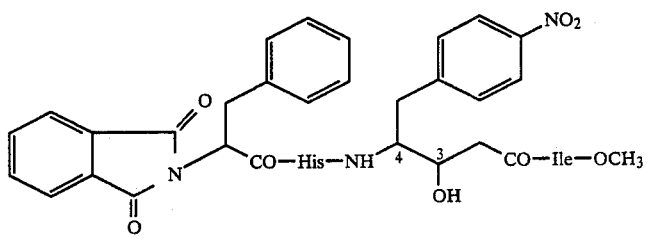

The title compound is prepared analogously to Example 12 from 4S-amino-3S-hydroxy-5-(4-nitrophenyl)-pentanoyl-L-isoleucine-methyl ester hydrochloride (Example 11) and di-tert.-butoxycarbonyl-L-histidine.
(+)FAB-MS: m/z 719 (M+H); m/z 619
TLC system I: $R_f=0.64$
HPLC value, system II: $R_t=13.47$ minutes

EXAMPLE 72

L-Histidyl-4S-amino-3S-hydroxy-5-(4-nitrophenyl)pentanoyl-L-isoluecine-methyl ester dihydrochloride

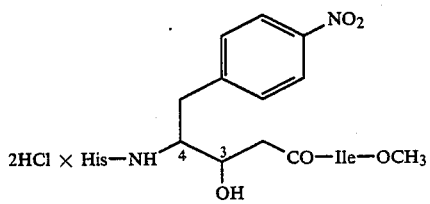

The title compound is obtained analogously to Example 11 by splitting off the protective groups from Nα,Nτ-di-tert.-butoxycarbonyl-L-histidyl-4S-amino-3S-hydroxy-5-(4-nitrophenyl)pentanoyl-L-isoleucine-methyl ester (Example 71) under acid conditions.
(+)FAB-MS: m/z 519 (M+H)
TLC system I: $R_f=0$; IV: $R_f=0.36$; XI: $R_f=0.21$.

EXAMPLE 73

N-p-Tolylsulphonyl-L-phenylalanyl-L-histidyl-4S-amino-3S-hydroxy-5-(4-nitrophenyl)pentanoyl-L-isoleucine-methyl ester

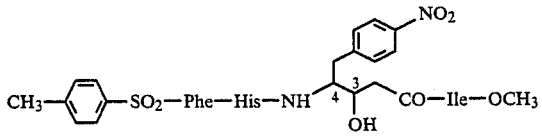

The title compound is obtained starting from L-histidyl-4S-amino-3S-hydroxy-5-(4-nitrophenyl)pentanoyl-L-isoleucine-methyl ester dihydrochloride (Example 72) and N-tosyl-L-phenylalanine by the PPA coupling method (analogously to Example 37 and 47).

(+)FAB-MS: m/z 820 (M+H); m/z 842 (M+Na)
TLC system I: $R_f=0.53$, IV: $R_f=0.98$, XI: $R_f=0.49$.
HPLC value, system II: $R_t=6.80$ minutes

EXAMPLE 74

N-Phthalyl-L-phenylalanyl-L-histidyl-4S-amino-3S-hydroxy-5-(4-nitrophenyl)pentanoyl-L-isoleucine-methyl ester

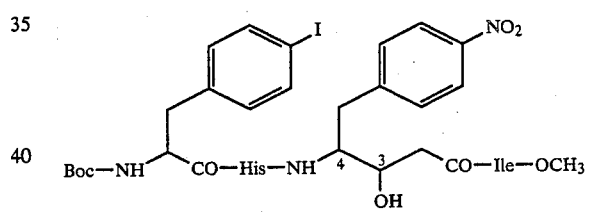

The title compound is obtained starting from L-histidyl-4S-amino-3S-hydroxy-5-(4-nitrophenyl)pentanoyl-L-isoleucine methyl ester dihydrochloride (Example 72) and N-phthalyl-L-phenylalanine by the PPA coupling method (analogously to Example 37 and 47).
(+)FAB-MS: m/z 796 (M+H)
TLC system I: $R_f=0.51$, IV: $R_f=0.98$, XI: $R_f=0.46$.
HPLC value, system II: $R_f=6.51$ minutes

EXAMPLE 75

N-tert.-Butoxycarbonyl-L-(4-iodophenyl)alanyl-L-histidyl-4S-amino-3S-hydroxy-5-(4-nitrophenyl)pentanoyl-L-isoleucine-methyl ester

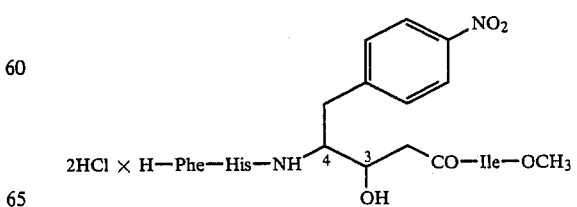

The title compound is obtained starting from L-histidyl-4S-amino-3S-hydroxy-5-(4-nitrophenyl)pentanoyl-L-isoleucine-methyl ester dihydrochloride and N-tert.-butoxycarbonyl-L-(4-iodophenyl)alanine by the PPA coupling method (analogously to Example 37 and 47).
(+)FAB-MS: m/z 892 (M+H); m/z 914 (M+Na)
TLC system XI: $R_f=0.48$
HPLC value, system II: $R_t=13.64$ minutes

EXAMPLE 76

L-Phenylalanyl-L-histidyl-4S-amino-3S-hydroxy-5-(4-nitrophenyl)pentanoyl-L-isoleucine-methyl ester dihydrochloride

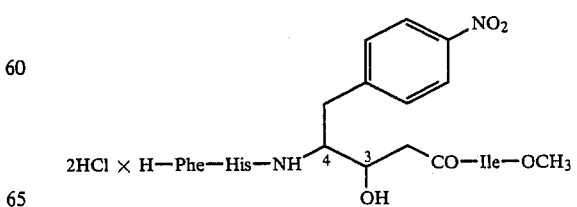

The title compound is obtained by splitting off the butoxycarbonyl protective group—analogously to Example 11—from N-tert.-butoxycarbonyl-L-phenylalanyl-L-histidyl-4S-amino-3S-hydroxy-5-(4-nitrophenyl)-pentanoyl-L-isoleucine-methyl ester (Example 12).
(+)FAB-MS: m/z 666 (M+H)
TLC system I: $R_f=0.52$
TLC system XI: $R_f=0.42$
HPLC value, system II: $R_t=4.39$ minutes

EXAMPLE 77

N-Acetyl-L-phenylalanyl-L-histidyl-4S-amino-3S-hydroxy-5-(4-nitrophenyl)pentanoyl-L-isoleucine methyl ester

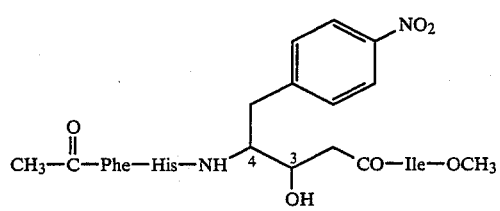

480 mg (0.65 mmol) of L-phenylalanyl-L-histidyl-4S-amino-3S-hydroxy-5-(4-nitrophenyl)pentanoyl-L-isoleucine-methyl ester dihydrochloride (Example 76) are dissolved in 10 ml of CH$_2$CL$_2$, 115 μl (1.43 mmol) of pyridine, 200 μl (1.43 mmol) of triethylamine and, finally, 68 μl (0.715 mmol) of acetic anhydride are added and the mixture is stirred at room temperature overnight. After addition of 10 ml of CH$_2$Cl$_2$, the batch is washed with 0.1N HCl to pH 6.5, with sodium bicarbonate solution and water. The organic phase is dried with sodium sulphate and concentrated. The crude product obtained after crystallization from ether (296.3 mg=64% of theory) is resolved by preparative thick layer chromatography (PTLC) on Merck 20×20 cm PTLC pre-coated plates, silica gel 60 F$_{254}$, layer height 2 mm, Cat. No. 5717 with the mobile phase system XI (CH$_2$Cl$_2$/MeOH/NH$_3$=9/1/0.2). The zone containing the substances is separated out and extracted with CH$_2$Cl$_2$/MeOH 9/1. Concentration of the filtrate gives 92.9 mg of the title compound.
Yield: 92.9 mg (20% of theory)
(+)FAB-MS: m/z 708 (M+H)
TLC system I: $R_f=0.34$
TLC system XI: $R_f=0.53$
HPLC value, system II: $R_t=2.60$ minutes

EXAMPLE 78

N-Benzyloxycarbonyl-L-phenylalanyl-L-histidyl-4S-amino-3S-hydroxy-5-(4-nitrophenyl)pentanoyl-L-isoleucine methyl ester

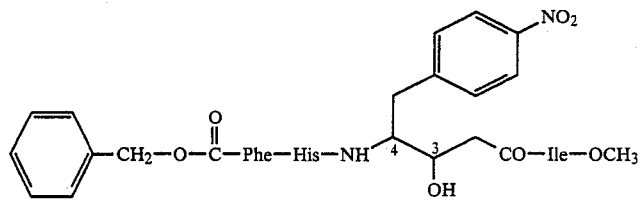

480 mg (0.65 mmol) of L-phenylalanyl-L-histidyl-4S-amino-3S-hydroxy-5-(4-nitrophenyl)pentanoyl-L-isoleucine-methyl ester dihydrochloride (Example 76) are dissolved in 10 ml of THF by addition of 200 μl (1.43 mmol) of triethylamine. After addition of 243 mg (0.975 mol) of N-(benzyloxycarbonyloxy)succinimide, the mixture is stirred overnight at room temperature. After addition of 49 mg (0.65 mmol) of glycine, the batch is stirred for a further hour and then diluted with 10 ml of CH$_2$Cl$_2$ and worked up analogously to Example 77. PTLC of the crude product (289.9 mg=56% of theory) gives 81 mg of the title compound.
Yield: 81.1 mg (15% of theory)
(+)FAB-MS: m/z 800 (M+H); m/z 822 (M+Na)
TLC system I: $R_f=0.62$
TLC system XI: $R_f=0.53$
HPLC value, system II: $R_t=7.38$ minutes

EXAMPLE 79

N-Phenoxyacetyl-L-phenylalanyl-L-histidyl-4S-amino-3S-hydroxy-5-(4-nitrophenyl)pentanoyl-L-isoleucine-methyl ester

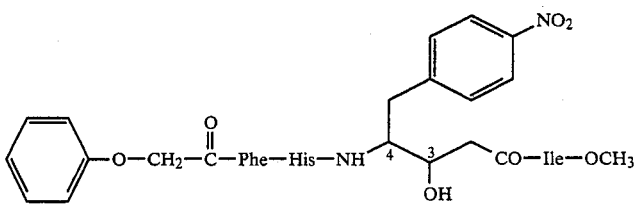

The title compound is obtained from L-phenyl-alanyl-L-histidyl-4-S-amino-3S-hydroxy-5-(4-nitrophenyl)-pentanoyl-L-isoleucine-methyl ester dihydrochloride (Example 76) by DCC/HOBT coupling (as described in Example 12) with phenoxyacetic acid. After PTLC—analogously to Example 77—the compound is obtained in an analytically pure form.
(+)FAB-MS: m/z 800 (M+H)
TLC system I: $R_f=0.32$
TLC system XI: $R_f=0.51$
HPLC value, system II: $R_t=6.59$ minutes

EXAMPLE 80

N-Isovaleroyl-L-phenylalanyl-L-histidyl-4S-amino-3S-hydroxy-5-(4-nitrophenyl)pentanoyl-L-isoleucine-methyl ester

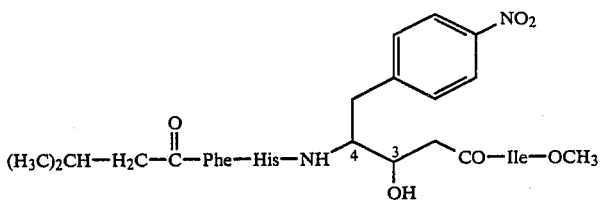

The title compound is obtained from L-phenylalanyl-L-histidyl-4S-amino-3S-hydroxy-5-(4-nitrophenyl)pentanoyl-L-isoleucine-methyl ester dihydrochloride (Example 76) and isovaleric acid by coupling with propanephosphonic acid anhydride (PPA, analogously to Example 37 and 47).

(+)FAB-MS: m/z 750 (M+H)
TLC system I: $R_f$=0.40
TLC system XI: $R_f$=0.51
HPLC value, system II: $R_t$=5.01 minutes

EXAMPLE 81

N-tert.-Butoxycarbonyl-L-phenylalanyl-L-phenylalanyl-L-histidyl-4S-amino-3S-hydroxy-5-(4-nitrophenyl)-pentanoyl-L-isoleucine-methyl ester

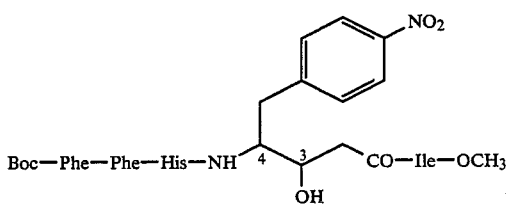

The title compound is obtained from L-phenylalanyl-L-histidyl-4S-amino-3S-hydroxy-5-(4-nitrophenyl)pentanoyl-L-isoleucine-methyl ester dihydrochloride (Example 76) and N-tert,-butoxycarbonyl-L-phenylalanine by the PPA coupling method described in Example 47.

(+)FAB-MS: m/z 913 (M+H); m/z 935 (M+Na)
TLC system I: $R_f$=0.35
TLC system XI: $R_f$=0.54
HPLC value, system II: $R_t$=12.70 minutes

EXAMPLE 82

N-tert.-Butoxycarbonyl-L-phenylalanyl-L-histidyl-4S-amino-3S-hydroxy-5-(4-nitrophenyl)pentanoyl-L-isoleucine

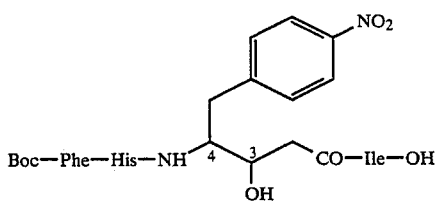

The title compound is prepared from N-tert.-butoxycarbonyl-L-phenylalanyl-L-histidyl-4S-amino-3S-hydroxy-5-(4-nitrophenyl)pentanoyl-L-isoleucine-methyl ester (Example 12) by alkaline hydrolysis (as described in Example 48).

(+)FAB-MS: m/z 752 (M+H); m/z 774 (M+Na)
TLC system I: $R_f$=0.25
TLC system II: $F_f$=0.05

EXAMPLE 83

N-tert.-Butoxycarbonyl-L-phenylalanyl-L-histidyl-4S-amino-3S-hydroxy-5-(4-nitrophenyl)pentanoyl-D,L-isoleucine isopropyl ester

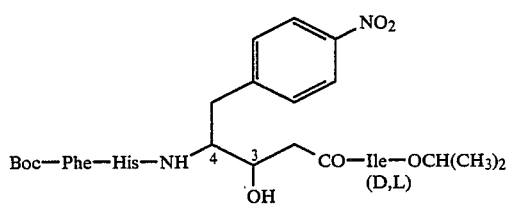

350 mg (0.5 mmol) of N-tert.-butoxycarbonyl-L-phenylalanyl-L-histidyl-4S-amino-3S-hydroxy-5-(4-nitrophenyl)pentanoyl-L-isoleucine (Example 82) are dissolved in 10 ml of methylene chloride. 105 mg of DCC (110 mol %), 33 µl of isopropanol (110 mil %) and, finally, 60 mg (100 mol %) of dimethylaminopyridine are added and the batch is stirred at room temperature for 2 days. The mixture is diluted with 10 ml of methylene chloride and washed in succession with sodium bicarbonate solution, sodium chloride solution and sodium bisulphate solution. The crude product obtained after concentration of the organic phase is resolved by isocratic high pressure liquid chromatography on a Merck LiChrosorb RP-8 column 7 µm, Cat-No. 51 441 with the mobile phase mixture acetonitrile/10 mmol of ammonium acetate (brought to pH 8.2 with NH₃) 50/50. The fractions containing the two isomers are combined and lyophilized.

(+)FAB-MS: m/z 794 (M+H)
TLC system I: $R_f$=0.54
TLC system II: $R_f$=0.47
HPLC value, system II: $R_t$=12.58 (isomer A); $R_t$=13.86 (isomer B).

EXAMPLE 84

N-tert.-Butoxycarbonyl-L-(3,4-dichlorophenyl)alanyl-L-histidyl-4S-amino-3S-hydroxy-5-(4-nitrophenyl)pentanoyl-L-isoleucine-methyl ester

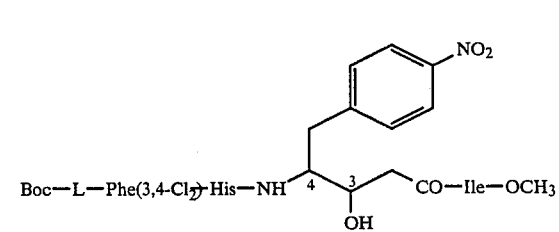

The title compound is prepared analogously to Example 12 from 4S-amino-3S-hydroxy-5-(4-nitrophenyl)-pentanoyl-L-isoleucine-methyl ester hydrochloride (Example 11) and N-tert.-butoxycarbonyl-L-(3,4- dichlorophenyl)alanyl-L-histidine [obtainable by PPA coupling of N-tert.-butoxycarbonyl-L-(3,4-dichlorophenyl)alanine and histidine methyl ester (analogously to Example 47) and subsequent hydrolysis (analogously to Example 48) of the product].

(+)FAB-MS: m/z 834 (M+H)
TLC system XI: R$_f$=0.58
HPLC value, system II: R$_t$=14.55 minutes

EXAMPLE 85

N-tert.-Butoxycarbonyl-L-(1-naphthyl)alanyl-L-histidyl-4S-amino-3S-hydroxy-5-(4-nitrophenyl)pentanoyl-L-isoleucine-methyl ester

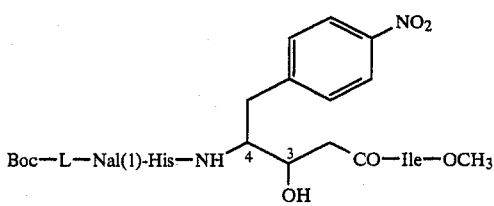

The title compound is prepared analogously to Example 12 from 4S-amino-3S-hydroxy-5-(4-nitrophenyl)-pentanoyl-L-isoleucine-methyl ester hydrochloride (Example 11) and N-tert.-butoxycarbonyl-L-(1-naphthyl)alanyl-L-histidine [obtainable by PPA coupling of N-tert.-butoxycarbonyl-L-(1-naphthyl)alanine and histidinemethyl ester (analogously to Example 47) and subsequent hydrolysis (analogously to Example 48) of the product].

(+)FAB-MS: m/z 916 (M+H)
TLC system XI: R$_f$=0.56
HPLC value, system II: R$_t$=11.92 minutes

EXAMPLE 86

N-tert.-Butoxycarbonyl-L-(4-nitrophenyl)alanyl-L-histidyl-4S-amino-3S-hydroxy-5-(4-nitrophenyl)pentanoyl-L-isoleucine-methyl ester

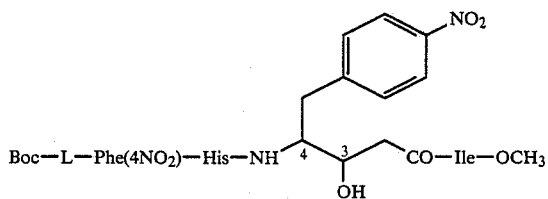

The title compound is prepared analogously to Example 12 from 4S-amino-3S-hydroxy-5-(4-nitrophenyl)-pentanoyl-L-isoleucine-methyl ester hydrochloride (Example 11) and N-tert.-butyoxycarbonyl-L-(4-nitrophenyl)alanyl-L-histidine [obtainable by PPA coupling of N-tert.-butoxycarbonyl-L-(4-nitrophenyl)alanine and histidine methyl ester (analogously to Example 47) and subsequent hydrolysis (analogously to Example 48) of the product].

(+)FAB-MS: m/z 811 (M+H)
TLC system XI: R$_f$=0.48
HPLC value, system II: R$_t$=6.71 minutes

EXAMPLE 87

N-tert.-Butoxycarbonyl-D,L-phenylglycyl-L-histidyl-4S-amino-3S-hydroxy-5-(4-nitrophenyl)pentanoyl-L-isoleucine methyl ester

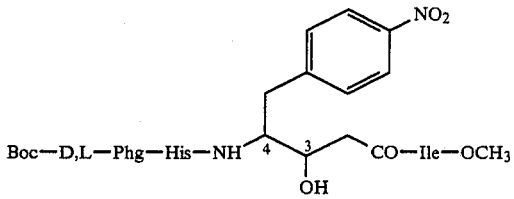

The title compound is prepared analogously to Example 12 from 4S-amino-3S-hydroxy-5-(4-nitrophenyl)-pentanoyl-L-isoleucine-methyl ester hydrochloride (Example 11) and N-tert.-butyoxycarbonyl-D,L-(phenyl)glycyl-L-histidine [obtainable by PPA coupling of N-tert.-butoxycarbonyl-D,L-phenylglycine and histidine methyl ester (analogously to Example 47) and subsequent hydrolysis (analogously to Example 48) of the product].

(+)FAB-MS: m/z 752 (M+H); m/z 766 (M+Na)
TLC system XI: R$_f$=0.52 (isomer A) and 0.50 (isomer B)
HPLC value, system II: R$_t$=5.46 minutes, cannot be differentiated

EXAMPLE 88

N-tert.-Butoxycarbonyl-L-prolyl-L-phenylalanyl-L-histidyl-4S-amino-3S-hydroxy-5-(4-nitrophenyl)pentanoyl-L-isoleucine-methyl ester

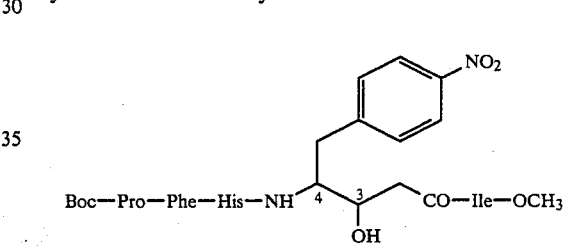

The title compound is prepared analogously to Example 12 from 4S-amino-3S-hydroxy-5-(4-nitrophenyl)-pentanoyl-L-isoleucine-methyl ester hydrochloride (Example 11) and N-tert.-butoxycarbonyl-L-prolyl-L-phenylalanyl-L-histidine [obtainable by splitting off the protective group from Example 47 (analogously to Example 11), subsequent reaction of the product with N-tert.-butoxycarbonyl-L-proline (analogously to Example 47) and subsequent hydrolysis of the coupling product (analogously to Example 48)].

(+)FAB-MS: m/z 863 (M+H)
TLC system XI: R$_f$=0.52
HPLC value, system II: R$_t$=7.87 minutes

EXAMPLE 89

N-Ethoxycarbonyl-L-phenylalanyl-L-histidyl-4S-amino-3S-hydroxy-5-(4-nitrophenyl)pentanoyl-L-isoleucine-methyl ester

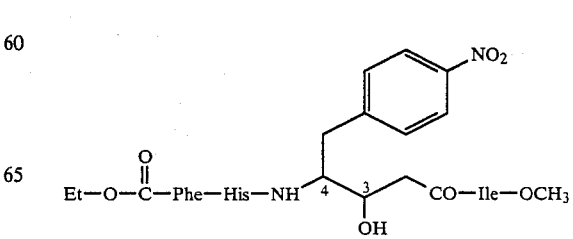

The title compound is prepared analogously to Example 12 from 4S-amino-3S-hydroxy-5-(4-nitrophenyl)-pentanoyl-L-isoleucine-methyl ester hydrochloride (Example 11) and N-ethoxycarbonyl-L-phenylalanyl-L-histidine [obtainable by PPA coupling of N-ethoxycarbonyl-L-phenylalanine and histidine methyl ester (analogously to Example 47) and subsequent hydrolysis (analogously to Example 48) of the product].

(+)FAB-MS: m/z 738 (M+H)
TLC system XI: $R_f$=0.51
HPLC value, system II: $R_t$=4.33 minutes

EXAMPLE 90

N-Benzoyl-L-phenylalanyl-L-histidyl-4S-amino-3S-hydroxy-5-(4-nitrophenyl)pentanoyl-L-isoleucine-methyl ester

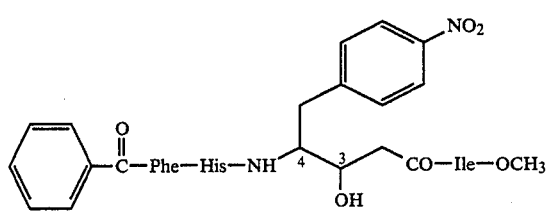

The title compound is prepared analogously to Example 12 from 4S-amino-3S-hydroxy-5-(4-nitrophenyl)-pentanoyl-L-isoleucine-methyl ester hydrochloride (Example 11) and N-benzoyl-L-phenylalanyl-L-histidine [obtainable by PPA coupling of N-benzoyl-L-phenylalanine and histidine methyl ester (analogously to Example 47) and subsequent hydrolysis (analogously to Example 48) of the product].

(+)FAB-MS: m/z 770 (M+H)
TLC system XI: $R_f$=0.48
HPLC value, system II: $R_f$=5.72 minutes

EXAMPLE 91

N-tert.-Butoxycarbonyl-D-phenylalanyl-L-histidyl-4S-amino-3S-hydroxy-5-(4-nitrophenyl)pentanoyl-L-isoleucine-methyl ester

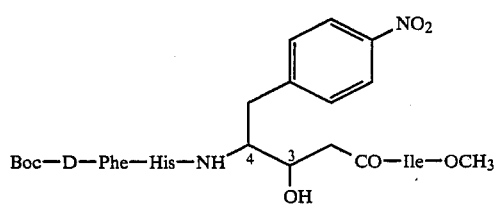

The title compound is prepared analogously to Example 12 from 4S-amino-3S-hydroxy-5-(4-nitrophenyl)-pentanoyl-L-isoleucine-methyl ester hydrochloride (Example 11) and N-tert.-butoxycarbonyl-D-phenylalanyl-L-histidine [obtainable by PPA coupling of N-tert.-butoxycarbonyl-D-phenylalanine and histidine methyl ester (analogously to Example 47) and subsequent hydrolysis (analogously to Example 48 ) of the product].

(+)FAB-MS: m/z 766 (M+H)
TLC system XI: $R_f$=0.44
HPLC value, system II: $R_t$=7.13 minutes

EXAMPLE 92

N-tert.-Butoxycarbonyl-L-phenyl-alanyl-L-histidyl-4S-amino-3RS-hydroxy-5-(3-aminophenyl)pentanoyl-L-isoleucine-methyl ester

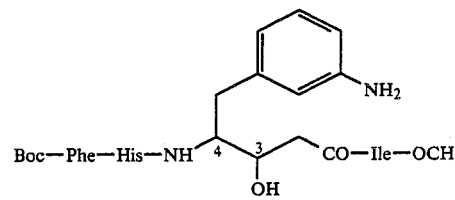

The title compound is obtained analogously to Example 42 by catalytic reduction from N-tert.-butoxycarbonyl-L-phenylalanyl-L-histidyl-4S-amino-3RS-hydroxy-5-(3-nitrophenyl)pentanoyl-L-isoleucine-methyl ester (Example 61).

(+)FAB-MS: 736 (M+H)

EXAMPLE 93

N-tert.-Butoxycarbonyl-4S-amino-3RS-hydroxy-5-(4-nitrophenyl)pentanoyl-L-isoleucine-methyl ester

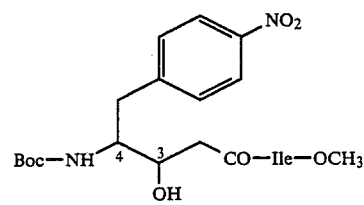

The title compound is obtained starting from N-tert.-butoxycarbonyl-4S-amino-3RS-hydroxy-5-(4-nitrophenyl)pentanoic acid (Example 64) and isoleucine methyl ester analogously to Example 10.

EXAMPLE 94

4S-Amino-3RS-hydroxy-5-(4-nitrophenyl)pentanoyl-L-isoleucine-methyl ester hydrochloride

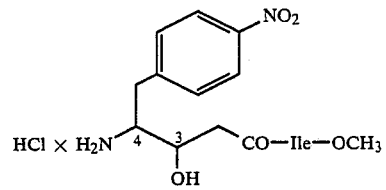

The title compound is obtained analogously to Example 11 from N-tert.-butoxycarbonyl-4S-amino-3RS-hydroxy-5-(4-nitrophenyl)pentanoyl-L-isoleucine-methyl ester (Example 93).

EXAMPLE 95

N-tert.-Butoxycarbonyl-L-tyrosyl-L-histidyl-4S-amino-3RS-hydroxy-5-(4-nitrophenyl)pentanoyl-L-isoleucine-methyl ester

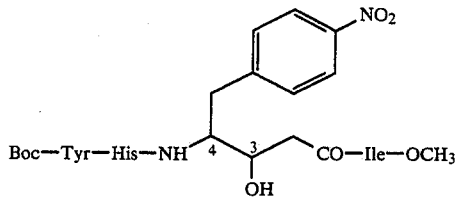

The title compound is prepared analogously to Example 12 from 4S-amino-3RS-hydroxy-5-(4-nitrophenyl)pentanoyl-L-isoleucine-methyl ester hydrochloride (Example 94) and N-tert.-butoxycarbonyl-L-tyrosyl-L-histidine [obtainable by PPA coupling of N-tert.-butoxycarbonyl-L-tyrosine and histidine methyl ester (analogously to Example 47) and subsequent hydrolysis (analogously to Example 48) of the product].

(+)FAB-MS: m/z 782 (M+H)
TLC system XII: $R_f$=0.25
HPLC value, system II: $R_t$=3.08 minutes

EXAMPLE 96

N-tert.-Butoxycarbonyl-L-(4-methoxyphenyl)alanyl-L-histidyl-4S-amino-3RS-hydroxy-5-(4-nitrophenyl)pentanoyl-L-isoleucine-methyl ester

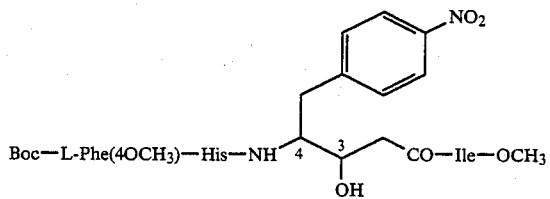

The title compound is prepared analogously to Example 12 from 4S-amino-3RS-hydroxy-5-(4-nitrophenyl)pentanoyl-L-isoleucine-methyl ester hydrochloride (Example 94) and N-tert.-butoxycarbonyl-L-(4-methoxyphenyl)alanyl-L-histidine [obtainable by PPA coupling of N-tert.-butoxycarbonyl-L-(4-methoxyphenyl)alanine and histidine methyl ester (analogously to Example 47) and subsequent hydrolysis (analogously to Example 48) of the product].

(+)FAB-MS: m/z 796 (M+H)
TLC system XII: $R_f$=0.33
HPLC value, system II: $R_t$=6.05 minutes

EXAMPLE 97

N-tert.-Butoxycarbonyl-L-prolyl-L-(4-methoxyphenyl)alanyl-L-histidyl-4S-amino-3RS-hydroxy-5-(4-nitrophenyl)pentanoyl-L-isoleucine-methyl ester

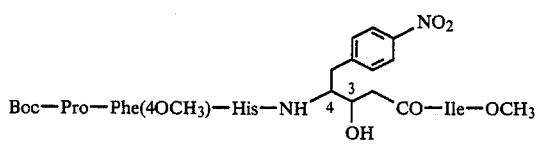

The title compound is obtained from N-tert.-butoxycarbonyl-L-(4-methoxyphenyl)alanyl-L-histidyl-4S-amino-3RS-hydroxy-(4-nitrophenyl)pentanoyl-L-isoleucine-methyl ester (Example 96) by splitting off the N-terminal protective group (analogously to Example 76) and subsequent coupling with N-tert.-butoxycarbonyl-L-proline (analogously to Example 81).

(+)FAB-MS: m/z 893 (M+H)
TLC system XI: $R_f$=0.45
HPLC value, system II: $R_t$=7.24 minutes

EXAMPLE 98

N-α-Phenoxyacetyl-L-histidyl-4S-amino-3RS-hydroxy-5-(4-nitrophenyl)pentanoyl-L-isoleucine-methyl ester

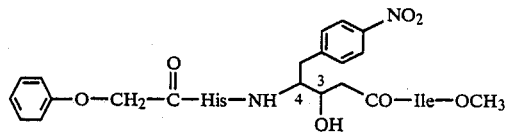

The title compound is prepared analogously to Example 12 from 4S-amino-3RS-hydroxy-5-(4-nitrophenyl)pentanoyl-L-isoleucine-methyl ester hydrochloride (Example 94) and N-α-phenoxyacetyl-L-histidine [obtainable by PPA coupling of phenoxyacetic acid and histidine methyl ester (analogously to Example 47) and subsequent hydrolysis (analogously to Example 48) of the product].

(+)FAB-MS: m/z 653 (M+H)
TLC system XII: $R_f$=0.25
HPLC value, system II: $R_t$=3.35 minutes

EXAMPLE 99

N-tert.-Butoxycarbonyl-L-(4-methoxyphenyl)alanyl-L-histidyl-4S-amino-3RS-hydroxy-5-(4-aminophenyl)pentanoyl-L-isoleucine-methyl ester

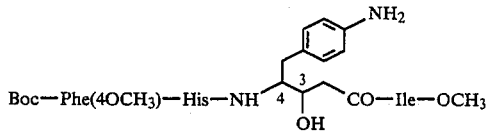

The title compound is obtained by catalytic reduction (analogously to Example 27) from N-tert.-butoxycarbonyl-L-(4-methoxyphenyl)alanyl-L-histidyl-4S-amino-3RS-hydroxy-5-(4-nitrophenyl)pentanoyl-L-isoleucine-methyl ester (Example 96).

(+)FAB-MS: m/z 766 (M+H)
HPLC value, system II: $R_t$=3.56 minutes

EXAMPLE 100

N-tert.-Butoxycarbonyl-L-tyrosyl-L-histidyl-4S-amino-3RS-hydroxy-5-(4-aminophenyl)pentanoyl-L-isoleucine-methyl ester

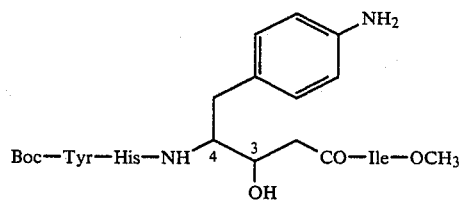

The title compound is obtained analogously to Example 99 from N-tert.-butoxycarbonyl-L-tyrosyl-L-histidyl-4S-amino-3RS-hydroxy-5-(4-nitrophenyl)pentanoyl-L-isoleucine-methyl ester (Example 95).

(+)FAB-MS: m/z 752 (M+H)
HPLC value, system II: $R_t$=2.06 minutes

EXAMPLE 101

Ethyl 4S-amino-3S-hydroxy-5-(4-nitrophenyl)pentanoate hydrochloride

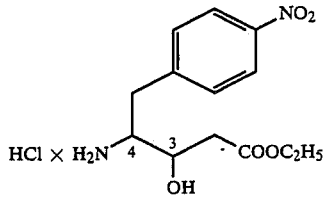

The title compound is obtained starting from ethyl N-tert.-butoxycarbonyl-4S-amino-3S-hydroxy-5-(4-nitrophenyl)pentanoate (Example 7) by splitting off the tert.-butoxycarbonyl protective group analogously to Example 11.

TLC system I: $R_f=0.19$

EXAMPLE 102

Ethyln-tert.-butoxycarbonyl-L-phenylalanyl-L-histidyl-4S-amino-3S-hydroxy-5-(4-nitrophenyl)pentanoate

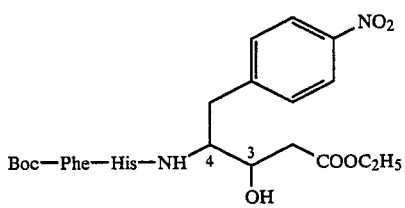

The title compound is obtained starting from N-tert.-butoxycarbonyl-L-phenylalanyl-L-histidine (Example 48) and ethyl 4S-amino-3S-hydroxy-5-(4-nitrophenyl)-pentanoate hydrochloride (Example 101) by DCC/HOBT coupling and subsequent chromatography (analogously to Example 12).

TLC system I: $R_f=0.46$
TLC system IV: $R_f=0.88$
TLC system V: $R_f=0.61$
TLC system XI: $R_f=0.43$
HPLC value, system II: $R_t=3.82$ minutes

EXAMPLE 103

N-tert.-Butoxycarbonyl-4S-amino-3S-hydroxy-5-(4-nitrophenyl)-pentanoyl-L-leucineamide

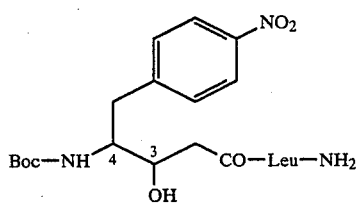

The title compound is obtained starting from N-tert.-butoxycarbonyl-4S-amino-3S-hydroxy-5-(4-nitrophenyl)pentanoic acid (Example 9) and leucineamide by the PPA coupling method analogously to Example 37.

(30)FAB-MS: m/z 467 (M+H); m/z 489 (M+Na)
TLC system I: $R_f=0.40$
HPLC value, system II: $R_f=2.57$ minutes

EXAMPLE 104

N-tert.-Butoxycarbonyl-4S-amino-3S-hydroxy-5-(4-nitrophenyl)pentanoyl-L-phenylalanine-methyl ester

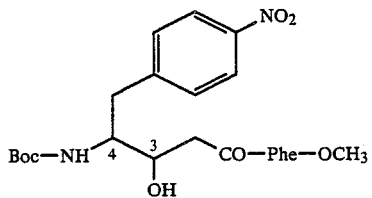

The title compound is obtained analogously to Example 103 from N-tert.-butoxycarbonyl-4S-amino-3S-hydroxy-5-(4-nitrophenyl)pentanoic acid (Example 9) and L-phenylalaninemethyl ester hydrochloride.

(+)FAB-MS: m/z 516 (M+H); m/z 538 (M+Na)
TLC system I: $R_f=0.67$
HPLC value, system II: $R_t=7.14$

EXAMPLE 105

N-tert.-Butoxycarbonyl-4S-amino-3S-hydroxy-5-(4-nitrophenyl)pentanoyl-R(+)-α-methylbenzylamide

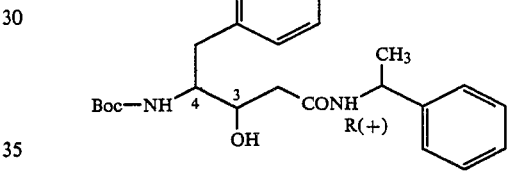

The title compound is obtained analogously to Example 103 from N-tert.-butoxycarbonyl-4S-amino-3S-hydroxy-5-(4-nitrophenyl)-pentanoic acid (Example 9) and R-(+)-α-methylbenzylamine.

(+)FAB-MS: m/z 458 (M+H); m/z 402, m/z 358
TLC system I: $R_f=0.61$
HPLC value, system II: $R_t=6.22$ minutes

EXAMPLE 106

N-tert.-Butoxycarbonyl-L-phenylalanyl-L-histidyl-4S-amino-3S-hydroxy-5-(4-nitrophenyl)pentanoyl-L-leucineamide

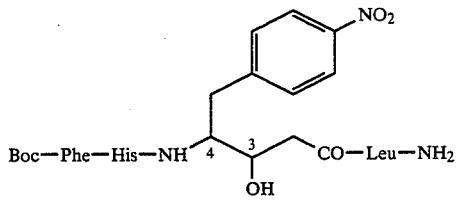

The title compound is obtained starting from N-tert.-butoxycarbonyl-4S-amino-3S-hydroxy-5-(4-nitrophenyl)pentanoyl-L-leucineamide (Example 103) analogously to Example 40 and Example 41 by splitting off the protective group and subsequent coupling with Boc-Phe-His-OH (Example 48).

(+)FAB-MS: m/z 751 (M+H)
TLC system I: $R_f=0.64$
HPLC value, system I: $R_t=3.11$

EXAMPLE 107

N-tert.-Butoxycarbonyl-L-phenylalanyl-L-histidyl-4S-amino-3S-hydroxy-5-(4-nitrophenyl)pentanoyl-L-phenylalaninemethyl ester

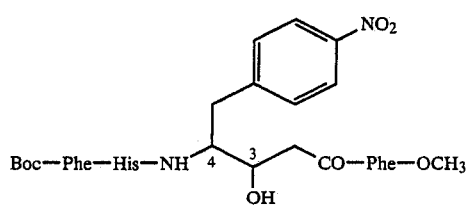

The title compound is obtained starting from N-tert.-butoxycarbonyl-4S-amino-3S-hydroxy-5-(4-nitrophenyl)pentanoyl-L-phenylalanine-methyl ester (Example 104) analogously to Example 40 and Example 41 by splitting off the protective group and subsequent coupling with Boc-Phe-His-OH (Example 48).

(+)FAB-MS: m/z 800 (M+H)
TLC system I: $R_f = 0.72$
HPLC value, system II: $R_t = 7.45$ minutes

EXAMPLE 108

N-tert.-Butoxycarbonyl-L-phenylalanyl-L-histidyl-4S-amino-3S-hydroxy-5-(4-nitrophenyl)pentanoyl-R-(+)-(α)-methylbenzylamide

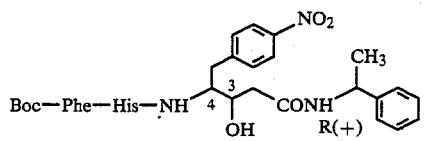

The title compound is obtained starting from N-tert.-butoxycarbonyl-4S-amino-3S-hydroxy-5-(4-nitrophenyl)pentanoyl-R(+)-α-methylbenzylamide (Example 105) analogously to Example 40 and Example 41 by splitting off the protective group and subsequent coupling with Boc-Phe-His-OH (Example 48).

TLC system I: $R_f = 0.65$
HPLC value, system II: $R_t = 6.65$

EXAMPLE 109

N-tert.-Butoxycarbonyl-4S-amino-3S-hydroxy-5-(4-nitrophenyl)pentanoyl-L-leucine-tert.-butyl ester

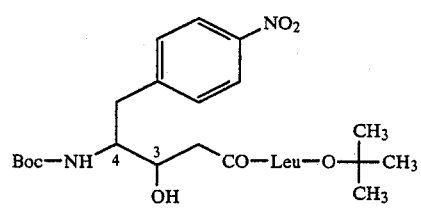

The title compound is obtained starting from N-tert.-butoxycarbonyl-4S-amino-3S-hydroxy-5-(4-nitrophenyl)pentanoic acid (Example 9) and L-leucine tert.-butyl ester hydrochloride by the PPA coupling method analogously to Example 37.

TLC system I: $R_f = 0.76$
HPLC value, system II: $R_t = 20.6$ minutes

EXAMPLE 110

N-tert.-Butoxycarbonyl-4S-amino-3S-hydroxy-5-(4-nitrophenyl)pentanoyl-L-leucine-benzyl ester

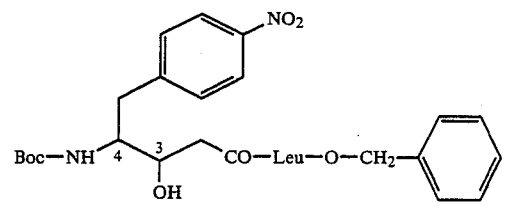

The title compound is obtained starting from N-tert.-butoxycarbonyl-4S-amino-3S-hydroxy-5-hydroxy-5-(4-nitrophenyl)pentanoic acid (Example 9) and L-leucine benzyl ester by the PPA coupling method analogously to Example 37.

TLC system I: $R_f = 0.85$
HPLC value, system II: $R_t = 19.9$ minutes

EXAMPLE 111

N-tert.-Butoxycarbonyl-L-phenylalanyl-L-histidyl-4S-amino-3S-hydroxy-5-(4-nitrophenyl)pentanoyl-L-leucine tert.-butyl ester

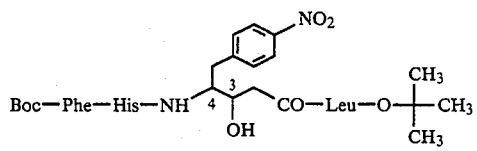

The title compound is prepared from 4S-amino-3S-hydroxy-5-(4-nitrophenyl)pentanoyl-L-leucine tert.-butyl ester (Example 113) and Boc-Phe-His-OH (Example 48) analogously to Example 12.

(+)FAB-MS: m/z 808 (M+H)
HPLC value, system II: $R_t = 13.22$ minutes

EXAMPLE 112

N-tert.-Butoxycarbonyl-L-phenylalanyl-L-histidyl-4S-amino-3S-hydroxy-5-(4-nitrophenyl)pentanoyl-L-leucine benzyl ester

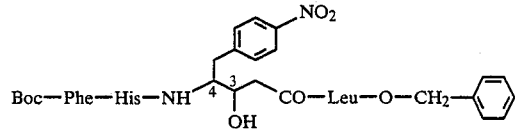

The title compound is obtained starting from N-tert.-butoxycarbonyl-4S-amino-3S-hydroxy-5-(4-nitrophenyl)pentanoyl-L-leucine benzyl ester (Example 110) analogously to Example 40 and Example 41 by splitting off the protective group and subsequent coupling with Boc-Phe-His-OH (Example 48).

(+)FAB-MS: m/z 842 (M+H)
HPLC value, system II: $R_t = 14.66$ minutes

EXAMPLE 113

4S-Amino-3S-hydroxy-5-(4-nitrophenyl)-pentanoyl-leucine tert.-butyl ester

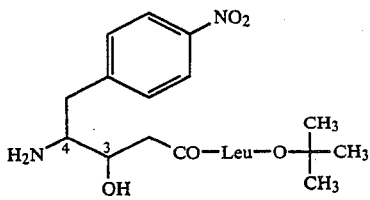

1.8 g (3.5 mmol) of N-tert.-butoxycarbonyl-4S-amino-3-S-hydroxy-5-(4-nitrophenyl)pentanoyl-L-leucine tert.-butyl ester (Example 109) are dissolved in 15 ml of CH₂Cl. The solution is cooled to 0° C., 5.2 ml (1,000 mol %) of trifluoroacetic acid are added to the mixture and the mixture is stirred at this temperature for 1 hour. The batch is poured onto 40 ml of water and the organic phase is separated off and discarded. The aqueous phase is brought to pH 9 with dilute sodium hydroxide solution and then extracted twice with 20 ml of ethyl acetate. The combined organic phase is washed with 5% strength sodium bicarbonate solution and saturated sodium chloride solution, dried with sodium sulphate and concentrated in vacuo.

Yield: 1.02 g (70% of theory)
(+)FAB-MS: m/z 424 (M+H); m/z 368
TLC system I: R$_f$=0.39

EXAMPLE 114

N-tert.-Butoxycarbonyl-L-phenylalanyl-L-histidyl-4S-amino-3R-hydroxy-5-(2-nitrophenyl)pentanoyl-L-isoleucine methyl ester

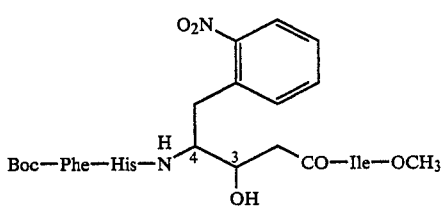

The title compound is obtained starting from N-tert.-butoxycarbonyl-4S-amino-3R-hydroxy-5-(2-nitrophenyl)pentanoyl-L-isoleucine-methylester (Example 38) analogously to Example 40 and Example 41 by splitting off the protective group and subsequent coupling with Boc-Phe-His-OH (Example 48).

TLC system I: R$_f$=0.7
HPLC value, system I: R$_t$=5.20 minutes
(+) FAB-MS: m/z 766 (M+H)

EXAMPLE 115

N-tert.-Butoxycarbonyl-4S-amino-3S-hydroxy-5-(3-nitrophenyl)pentanoic acid

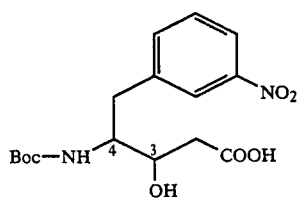

The title compound is prepared analogously to Example 9 from 6.7 g (18.2 mmol) ethyl N-tert.-butoxycarbonyl-4S-amino-3S-hydroxy-5-(3-nitrophenyl)pentanoate.

Yield: 3.6 g (70% of theory)
Melting point: 143° C.
TLC system I: R$_f$=0.25
TLC system X: R$_f$=0.70

EXAMPLE 116

N-tert.-Butoxycarbonyl-4S-amino-3S-hydroxy-5-(3-nitrophenyl)pentanoyl-L-isoleucine methyl ester

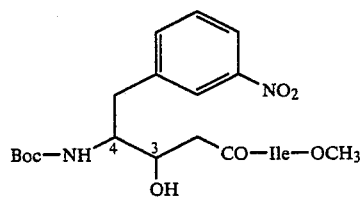

The title compound is prepared analogously to Example 37 from 2.6 g (7.3 mmol) of N-tert.-butoxycarbonyl-4S-amino-3S-hydroxy-5-(3-nitrophenyl)pentanoic acid (Example 115) and L-isoleucine methyl ester hydrochloride.

Yield: 3.25 g (92.5% of theory)
HPLC value, system II: R$_t$=6.66 minutes

EXAMPLE 117

4S-Amino-3S-hydroxy-5-(3-nitrophenyl)pentanoyl-L-isoleucine methyl ester hydrochloride

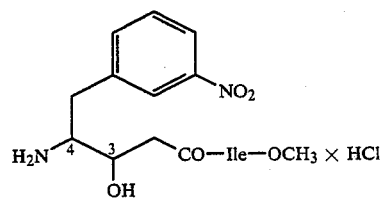

The title compound is prepared analogously to Example 11 from 2,5 g (5.2 mmol) of N-tert.-butoxycarbonyl-4S-amino-3S-hydroxy-5-(3-nitrophenyl)pentanoyl-L-isoleucine methyl ester (Example 116).

Yield: 2.97 g (95% of theory)

EXAMPLE 118

N-tert.-Butoxycarbonyl-L-phenylalanyl-L-histidyl-4S-amino-3S-hydroxy-5-(3-nitrophenyl)pentanoyl-L-isoleucine methyl ester

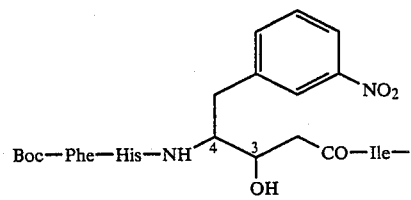

The title compound is prepared from 4S-amino-3S-hydroxy-5-(3-nitrophenyl)pentanoyl-L-isoleucine methyl ester hydrochloride (Example 117) and Boc-Phe-His-OH (Example 48) analogously to Example 12.

TLC system XI: R$_f$=0.72
HPLC value, system II: R$_t$=7.10 minutes (+) FAB-MS: m/z 766 (M+H)

EXAMPLE 119

N-tert.-Butoxycarbonyl-L-phenylalanyl-L-histidyl-4S-amino-3S-hydroxy-5-(3-aminophenyl)pentanoyl-L-isoleucine methyl ester

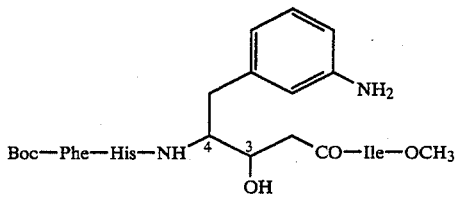

The title compound is obtained by catalytic reduction (analogously to Example 27) from N-tert.-butoxycarbonyl-L-phenylalanyl-L-histidyl-4S-amino-3S-hydroxy-5-(3-nitrophenyl)pentanoyl-L-isoleucine methyl ester (Example 118).

TLC system XI: $R_f$=0.33
HPLC value, system II: $R_t$=3.86 minutes
(+) FAB-MS: m/z 736 (M+H)

EXAMPLE 120

N-tert.-Butoxycarbonyl-4S-amino-3R-hydroxy-5-(4-nitrophenyl)pentanoyl-amide

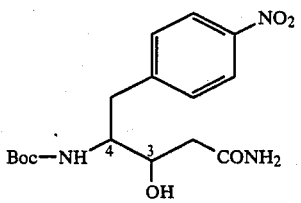

8.4 g (22 mmol) of ethyl N-tert.-butoxycarbonyl-4S-amino-3R-hydroxy-5-(4-nitrophenyl)pentanoate are dissolved in 150 ml of methanol saturated with ammonia. The solution is stirred for three days at room temperature in a flask sealed with a stopper.

The white precipitate is filtered off with suction, washed with diethylether and dried in vacuo over phosphorus pentoxide.

Yield: 4.3 g (55% of theory)
TLC system I: $R_f$=0.5
TLC system II: $R_f$=0.3
HPLC value; system II: $R_t$=1.63 minutes
$^1$H-NMR (200 MHz, DMSO): δ=8.12 (d, 2H); 7.45 (d, 2H); 7.30 (s, broad, 1H); 6.82 (s, broad, 1H); 6.69 (d, 1H); 5.10 (d, 1H); 3.78 (m, 1H); 3.53 (m, 1H); 3.16 (dd, 1H); 2.60 (dd, 1H); 2.05–2.38 (m, 2H); 1.2 (s, 9H).
(+) FAB-MS: m/z 354 (M+H); m/z 294, m/z 254.

EXAMPLE 121

N-tert.-Butoxycarbonyl-4S-amino-3S-hydroxy-5-(4-nitrophenyl)pentanoyl-amide

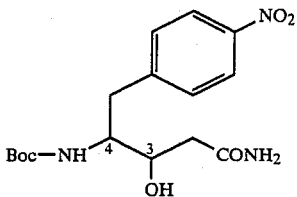

The title compound is obtained starting from Example 7 analogously to Example 120.
(+) FAB-MS: m/z 354 (M+H); m/z 294; m/z 254

EXAMPLE 122

N-tert.-Butoxycarbonyl-L-phenylalanyl-L-histidyl-4S-amino-3S-hydroxy-5-(4-nitrophenyl)pentanoyl-amide

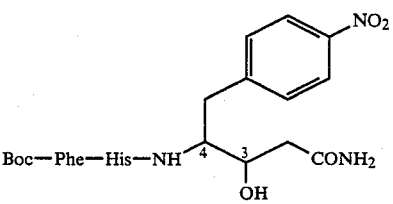

1.5 g (2.3 mmol) of ethyl N-tert.-butoxycarbonyl-L-phenylalanyl-L-histidyl-4S-amino-3S-hydroxy-5-(4-nitrophenyl)pentanoate (Example 102) are dissolved in 9 ml of methanol saturated with ammonia. The solution is stirred for two days at room temperature in a flask sealed with a stopper. The precipitate is filtered off with suction, washed with diethylether and dried. The crude product thus obtained (150 mg) is purified by preparative HPLC with the system described in Example 83. The fractions containing the pure product are combined and lyophilized.

Yield: 80 mg (5.5% of theory)
TLC system I: $R_f$=0.10
HPLC value; system II: $R_t$=2.22 minutes
(+) FAB-MS: m/z 638 (M+H); m/z 582; m/z 538

EXAMPLE 123

N-tert.-Butoxycarbonyl-L-phenylalanyl-L-histidyl-4S-amino-3S-hydroxy-5-(4-nitrophenyl)pentanoic acid

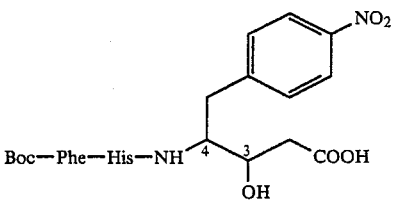

The title compound is prepared from ethyl N-tert.-butoxycarbonyl-L-phenylalanyl-L-histidyl-4S-amino-3S-hydroxy-5-(4-nitrophenyl)pentanoate (Example 102) by alkaline hydrolysis (as described in Example 48).
TLC system XIII: $R_f$=0.68
(+) FAB-MS: m/z 639 (M+H); m/z 583; m/z 539

EXAMPLE 124

N-tert.-Butoxycarbonyl-L-(4-methoxyphenyl)alanyl-L-histidyl-4S-amino-4RS-hydroxy-5-(2-nitrophenyl)-pentanoyl-L-isoleucine methyl ester

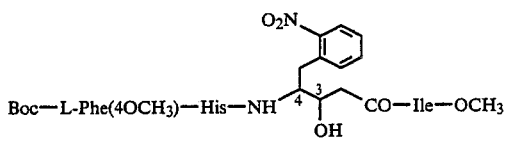

The title compound is prepared analogously to Example 12 from 4S-amino-3RS-hydroxy-5-(2-nitrophenyl)pentanoyl-L-isoleucine methyl ester hydrochloride [obtainable from Example 37 by splitting off the Boc protecting group (analogously to Example 11)] and N-tert.-butoxycarbonyl-L-(4-methxoyphenyl)alanyl-L-histidine [obtainable by PPA coupling of N-tert.-butoxycarbonyl-L-(4-methoxyphenyl)-alanine and histidine methyl ester (analogously to Example 47) and subsequent hydrolysis (analogously to Example 48) of the product], TLC system XII: $R_f$=0.48 (cannot be differentiated)
HPLC value, system II: $R_t$= =4.96 minutes (cannot be differentiated)
(+) FAB-MS: m/z 796 (M+H)

EXAMPLE 125

N-tert.-Butoxycarbonyl-L-prolyl-L-(4-methoxyphenyl)alanyl-L-histidyl-4S-amino-3RS-hydroxy-5-(2-nitrophenyl)pentanoyl-L-isoleucine methyl ester

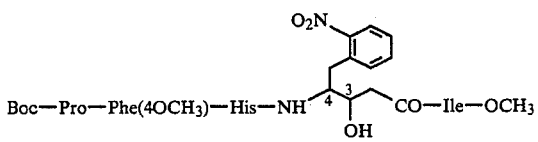

The title compound is obtained by splitting off the N-terminal protecting group (analogously to Example 76) and subsequent coupling with N-tert.-butoxycarbonyl-L-proline (analogously to Example 81) from N-tert.-butoxycarbonyl-L-(4-methoxyphenyl)alanyl-L-histidyl-4S-amino-3RS-hydroxy-(2-nitrophenyl)pentanoyl-L-isoleucine methyl ester (Example 124).

(+) FAB-MS: m/z 893 (M+H)

EXAMPLE 126

N-tert.-Butoxycarbonyl-L-prolyl-L-(4-methoxyphenyl)alanyl-L-histidyl-4S-amino-3RS-hydroxy-5-(4-aminophenyl)pentanoyl-L-isoleucine methyl ester

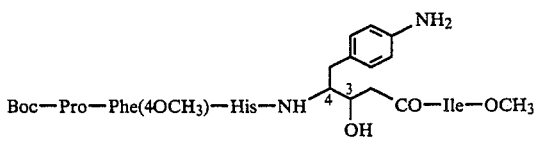

The title compound is obtained by catalytic reduction (analogously to Example 27) from N-tert.-butoxycarbonyl-L-prolyl-L-(4-methoxyphenyl)alanyl-L-histidyl-4S-amino-3RS-hydroxy-5-(4-nitrophenyl)pentanoyl-L-isoleucine methyl ester (Example 97).

TLC system XI: $R_f$=0.36 (cannot be differentiated)
HPLC value; system II: $R_t$=4.16 minutes (cannot be differentiated)
(+) FAB-MS: m/z 863 (M+H)

EXAMPLE 127

N-α-Phenoxyacetyl-L-histidyl-4S-amino-3RS-hydroxy-5-(4-aminophenyl)pentanoyl-L-isoleucine methyl ester

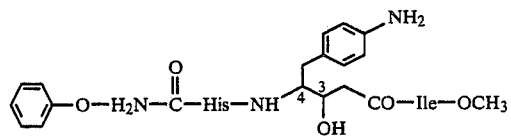

The title compound is obtained by catalytic reduction (analogously to Example 27) from N-α-Phenoxyacetyl-L-histidyl-4S-amino-3RS-hydroxy-5-(4-nitrophenyl)pentanoyl-L-isoleucine methyl ester (Example 98).

TLC system XI: $R_f$=0.31; isomer A; $R_f$=0.34; isomer B.
HPLC value; system II: $R_t$=2.09 minutes (cannot be differentiated)
(+) FAB-MS: m/z 623 (M+H)

EXAMPLE 128

N-tert.-Butoxycarbonyl-L-phenylalanyl-L-histidyl-4S-amino-3S-hydroxy-5-(4-nitrophenyl)pentanoyl-L-isoleucine-1-adamantylamide

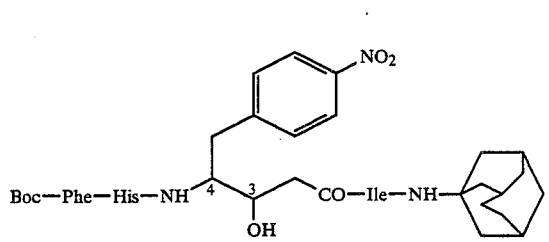

The title compound is obtained after methods already described before by the following steps:

(a) Coupling of N-tert.-butoxycarbonyl-4S-amino-3S-hydroxy-5-(4-nitrophenyl)pentanoic acid (Example 9) analogously to Example 37 with L-isoleucine-1-adamantylamide hydrochloride [obtainable by coupling of N-tert.-butoxycarbonyl-L-isoleucine with 1-adamantylamine (analogously to Example 65) and subsequent acidic cleavage of the N-tert.-butoxycarbonyl protecting group from the reaction product (analogous to Example 66)].

(b) Cleavage of the protecting group from the coupling product of step (a) and subsequent coupling of the obtained hydrochloride with Boc-Phe-His-OH (analogously to Example 40 and 41).

(c) Preparative HPLC of the coupling product from step (b) with the system described in Example 83.

TLC system I: $R_f$=0.40
HPLC value; system II: $R_t$=22.04 minutes
(+) FAB-MS: m/z 885 (M+H)

EXAMPLE 129

N-tert.-Butoxycarbonyl-L-phenylalanyl-L-histidyl-4S-amino-3S-hydroxy-5-(4-nitrophenyl)pentanoyl-L-isoleucine-2-adamatylamide

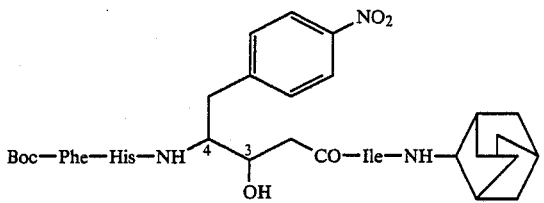

The title compound is obtained after methods already described before by the following steps:

(a) Coupling of N-tert.-butoxycarbonyl-4S-amino-3S-hydroxy-5-(4-nitrophenyl)pentanoic acid (Example 9) analogously to Example 37 with L-isoleucine-2-adamantylamide [obtainable by coupling of N-tert.-butoxycarbonyl-L-isoleucine with 2-adamantylamine (analogously to Example 65) and subsequent acidic cleavage of the N-tert.-butoxycarboyl protecting group from the reaction product (analogous to Example 66)].

(b) Cleavage of the protecting group from the coupling product of step (a) and subsequent coupling of the obtained hydrochloride with Boc-Phe-His-OH (analogously to Example 40 and 41).

(c) Preparative HPLC of the coupling product (from step (b) with the system described in Example 83.

TLC system XI: $R_f = 0.49$

HPLC value; system II: $R_t = 21.04$ minutes (+) FAB-MS: m/z 885 (M+H)

EXAMPLE 130

N-tert.-Butoxycarbonyl-L-phenylalanyl-L-histidyl-4S-amino-3S-hydroxy-5-(4-nitrophenyl)pentanoyl-(2-RS-methyl)butylamide

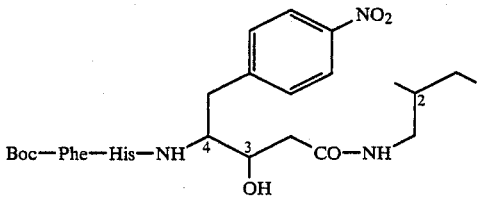

The title compound is obtained after methods already described before by the following steps;

(a) Coupling of N-tert.-butoxycarbonyl-4S-amino-3S-hydroxy-5-(4-nitrophenyl)pentanoic acid (Example 9) analogously to Example 37 with RS-2-methylbutylamine.

(b) Cleavage of the protecting group from the coupling product of step (a) and subsequent coupling of the obtained hydrochloride with Boc-Phe-His-OH (analogously to Example 40 and 41), (c) Preparative HPLC of the coupling product from step (b) with the system described in Example 83.

TLC system I: $R_f = 0.43$ (cannot be differentiated)

HPLC value; system II: $R_t = 4.83$ minutes (isomer A); $R_t = 5.13$ minutes (isomer B).

(+) FAB-MS: m/z 708 (M+H); m/z 652; m/z 608

EXAMPLE 131

N-tert.-Butoxycarbonyl-L-phenylalanyl-L-histidyl-4S-amino-3S-hydroxy-5-(4-nitrophenyl)pentanoyl-L-isoleucine-n-propylester

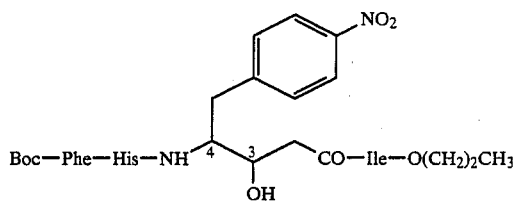

The title compound is obtained after methods already described before by the following steps:

(a) Coupling of N-tert.-butoxycarbonyl-4S-amino-3S-hydroxy-5-(4-nitrophenyl)pentanoic acid (Example 9) analogously to Example 37 with L-isoleucine-n-propylester hydrochloride.

(b) Cleavage of the protecting group from the coupling product of step (a) and subsequent coupling of the obtained hydrochloride with Boc-Phe-His-OH (analogously to Example 40 and 41).

(c) Preparative HPLC of the coupling product from step (b) with the system described in Example 83.

TLC system I: $R_f = 0.55$

HPLC value; system II: $R_t = 10.08$ minutes (+) FAB-MS: m/z 794 (M+H); m/z 694

EXAMPLE 132

N-tert.-Butoxycarbonyl-L-phenylalanyl-L-histidyl-4S-amino-3-S-hydroxy-5-(4-nitrophenyl)pentanoyl-L-leucine ethyl-esters

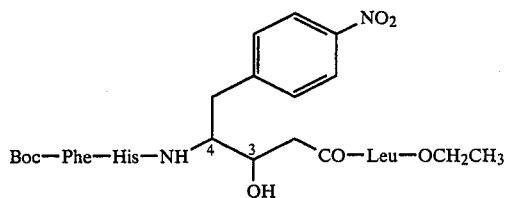

The title compound is obtained after methods already described before by the following steps:

(a) Coupling of N-tert.-butoxycarbonyl-4S-amino-3S-hydroxy-5-(4-nitrophenyl)pentanoic acid (Example 9) analogously to Example 37 with L-leucine ethylester hydrochloride.

(b) Cleavage of the protecting group from the coupling product of step (a) and subsequent coupling of the obtained hydrochloride with Boc-Phe-His-OH (analogously to Example 40 and 41).

(c) Preparative HPLC of the coupling product from step (b) with the system described in Example 83.

TLC system I: $R_f = 0.48$

HPLC value; system II: $R_t = 7.38$ minutes (+) FAB-MS: m/z 780 (M+H)

EXAMPLE 133

N-tert.-Butoxycarbonyl-L-phenylalanyl-L-histidyl-4S-amino-3R-hydroxy-5-(2-aminophenyl)pentanoyl-L-isoleucine methyl ester

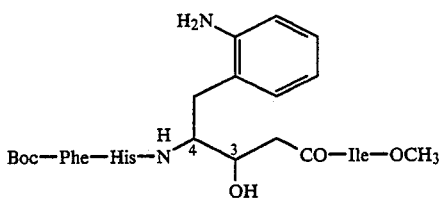

The title compound is obtained by catalytic reduction (analogously to Example 27) from N-tert.-butoxycarbonyl-L-phenylalanyl-L-histidyl-4S-amino-3R-hydroxy-5-(2-nitrophenyl)pentanoyl-L-isoleucine methyl ester (Example 114).

It is understood that the specification and examples are illustrative but not limitative of the present invention and that other embodiments within the spirit and scope of the invention will suggest themselves to those skilled in the art.

We claim:

1. A peptide containing up to either amino acid groupings of the formula

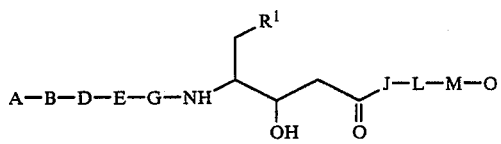

in which

A is hydrogen, $C_1$–$C_8$-alkyl, $C_7$–$C_{14}$-aralkyl, phenylsulphonyl, tolylsulphonyl or $C_1$–$C_8$-alkylsulphonyl, or is an amino-protective group, B, E, G, J, L and M each independently is a direct bond, sarcosyl, or a group of the formula

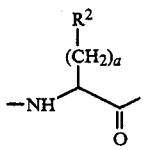

wherein a is the number 0, 1, 2, 3 or 4 and $R^2$ is hydrogen, $C_1$–$C_6$-alkyl, hydroxy-$C_1$–$C_2$-alkyl, a group of the formula —$CH_2$—CO—$NHR^3$ or —$CH_2$—NH—$R^3$, wherein $R^3$ is hydrogen, $C_1$–$C_6$-alkyl, $C_7$–$C_{14}$-aralkyl, tolylsulphonyl, phenylsulphonyl, $C_1$–$C_6$-alkylsulphonyl, or an amino-protective group, or $R^2$ is guanidinomethyl, mercaptomethyl, methylthiomethyl, carboxymethyl, $C_1$–$C_6$-alkoxycarbonylmethyl, $C_7$–$C_{14}$-aralkoxycarbonylmethyl, halogen, indolylmethyl, 4-imidazolylmethyl, pyridyl, triazolylmethyl, pyrazolylmethyl, aryl, or aryl which is substituted by $C_1$–$C_4$-alkyl, $C_1$–$C_4$-alkoxy, trifluoromethyl, halogen, hydroxyl, nitro or a group of the formula

wherein $R^4$ and $R^5$ each independently is hydrogen, $C_1$–$C_6$-alkyl, aryl, aralkyl, phenylsulphonyl, tolylsulphonyl, $C_1$–$C_6$-alkylsulphonyl, acetyl, benzoyl or an amino-protective group, D is a direct bond or a group of the formula

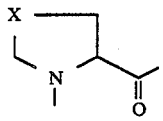

wherein

X is methylene, ethylene or sulphur, $R^1$ is a group of the formula

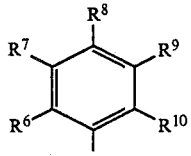

wherein $R^6$, $R^7$, $R^8$, $R^9$ and $R^{10}$ each independently is hydrogen, $C_1$–$C_6$-alkyl, $C_1$–$C_6$-alkoxy, aryl, halogen, hydroxyl, cyano, trifluoromethyl, trifluoromethoxy, trifluoromethylthio, nitro, or a group of the formula

wherein $R^{11}$ and $R^{12}$ each independently has the same meaning as $R^4$ and $R^5$, with the proviso that at least one of the substituents $R^6$, $R^7$, $R^8$, $R^9$ or $R^{10}$ is nitro or the group —$NR^{11}R^{12}$, and Q is a radical of the formula —$OR^{13}$, —$NHR^{14}$, —$NR^{14}R^{15}$ or —NH—$NHR^3$, wherein $R^{13}$ is hydrogen, $C_1$–$C_{20}$-alkyl or $C_1$–$C_{20}$-alkyl or $C_1$–$C_{20}$-alkyl which is interrupted in the chain by an oxygen atom $C_1$–$C_{20}$-alkyl which is substituted by halogen, hydroxyl, phenyl or pyridyl, $R^{14}$ represents hydrogen, $C_1$–$C_{10}$-alkyl, $C_1$–$C_{10}$-alkyl is substituted by aryl, aryl which which is substituted by nitro, $C_1$–$C_4$-alkyl, $C_1$–$C_4$-alkoxy, halogen or cyano, or $C_1$–$C_{10}$-alkyl which is substituted by halogen, adamantyl, quinuclidine, piperidine, N-methyl-piperazine, N-phenylpiperazine, N-benzylpiperazine, pyridyl or morpholine, or is aryl or aryl which is substituted by nitro, halogen, $C_1$–$C_4$-alkoxy, $C_1$–$C_4$-alkyl, or $C_1$–$C_4$-alkyl which is substituted by hydroxyl, amino, carboxyl or $C_1$–$C_4$-alkoxycarbonyl, or is adamantyl or quinuclidine, and $R^{15}$ is $C_1-C_6$-alkyl, or $R^{14}$ and $R^{15}$ together form a 5- to 7-membered ring which can contain, as a further hetero atom, an oxygen atom, a sulphur atom or the group —NH, —N—$C_1-C_6$-alkyl, —N-dimethylamino-$C_1-C_4$-alkyl, —N-aryl or —N-aralkyl, and wherein said ring is unsubstituted or substituted by $C_1-C_4$-alkyl or aralkyl, or a physiologically acceptable salt thereof.

2. A compound or salt according to claim 1, in which A is hydrogen, $C_1-C_4$-alkyl, benzyl, phenylsulphonyl, tolylsulphonyl, $C_1-C_4$-alkyl-sulphonyl, tolylsulphonyl, $C_1-C_4$-alkyl-sulphonyl, or is an aminoprotective group, B, E, G, J, L and M each independently is a direct bond or the D-Form, the L-Form or the D-L-isomer mixture a radical of the formula

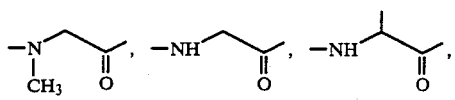

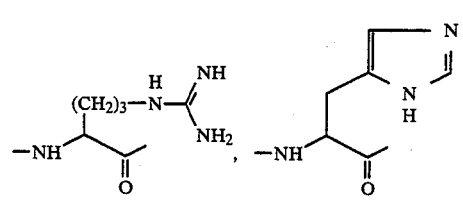

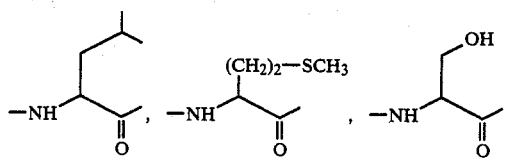

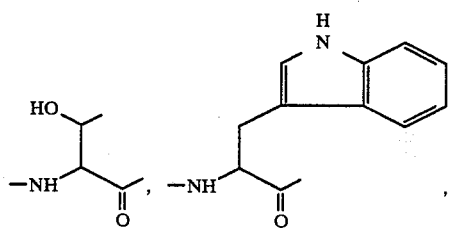

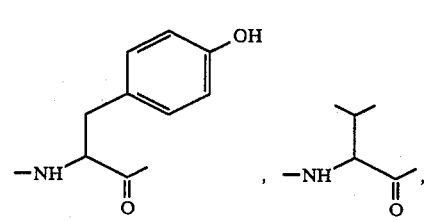

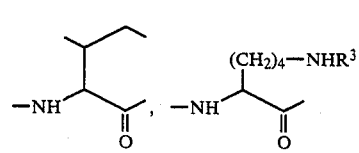

-continued

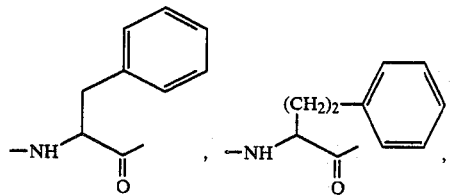

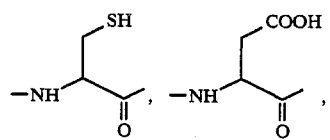

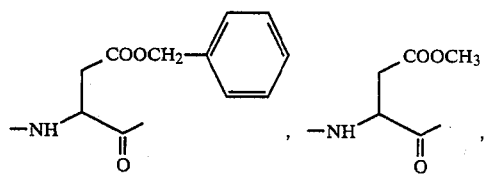

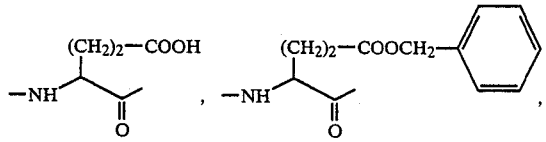

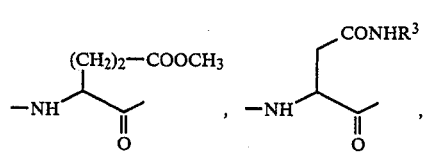

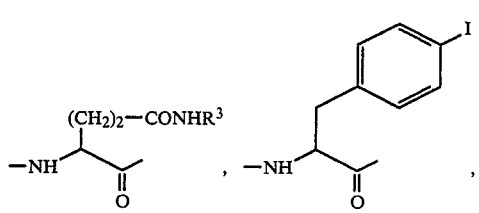

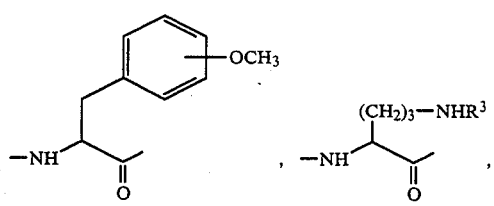

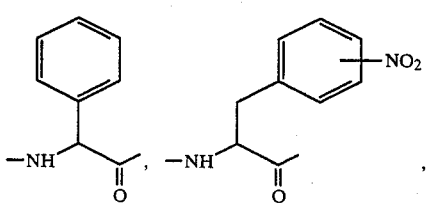

-continued

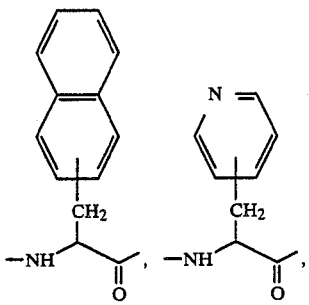
,
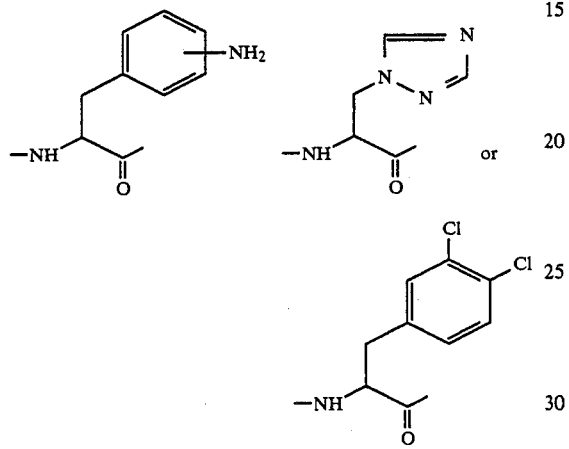
or
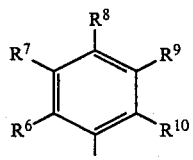

wherein
R³ is hydrogen, C₁-C₄-alkyl, benzyl, phenylsulphonyl, tolylsulphonyl or C₁-C₄-alkyl-sulphonyl, or is an amino-protective group, D is a direct bond, or is the group of the formula

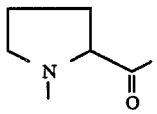

R¹ represents a group of the formula

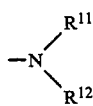

wherein
R⁶, R⁷, R⁸, R⁹ and R¹⁰ each independently is hydrogen, methyl, methoxy, fluorine, chlorine, bromine, iodine, hydroxyl, cyano, trifluoromethyl or nitro, or is a group of the formula

wherein
R¹¹ and R¹² each independently is hydrogen, C₁-C₄-alkyl, phenyl, benzyl, phenylsulphonyl, tosyl, C₁-C₄-alkylsulphonyl or acetyl, or is an amino-protective group, with the proviso that at least one of the substituents R⁶, R⁷, R⁸, R⁹ or R¹⁰ is nitro or is the group —NR¹¹R¹², and Q is a radical of the formula —OR¹³, —NH—NHR³, NHR¹⁴ or $$-N\begin{matrix}R^{14}\\R^{15}\end{matrix}$$

wherein
R¹³ is hydrogen, C₁-C₁₈-alkyl, or C₁-C₁₈-alkyl which is substituted by chlorine, bromine, hydorxyl or phenyl, R¹⁴ represents hydrogen, C₁-C₄-alkyl, or C₁-C₄-alkyl is substituted by phenyl or phenyl which is substituted by nitro, methyl or methoxy, or C₁-C₄-alkyl which is substituted fluorine, chlorine, bromine, pyridyl, adamantyl, quinuclidine, piperidine, N-methyl-, N-phenyl- or N-benzylpiperazine or benzylcyclohexyl, or R¹⁴ represents phenyl, or phenyl which is substituted by nitro, fluorine, chlorine or methoxy, C₁-C₄-alkyl or C₁-C₄-alkyl which is substituted by hydroxyl, amino, carboxyl or C₁-C₄-alkoxy-carbonyl, or R¹⁴ is adamantyl or quinuclidine and R¹⁵ is C₁-C₄-alkyl, or R¹⁴ and R¹⁵ together form a pyrrolidine, piperidine, benzylpiperidine, morpholine, piperazine or N-methyl-, N-phenyl-, N-benzyl- or N-dimethylaminoethylpiperazine.

3. A compound or salt according to claim 1 in which
A is hydrogen, methyl, ethyl, tosyl, or an amino-protective group selected from the group consisting of benzyloxycarbonyl, 4-methoxybenzyloxycarbonyl, 4-nitrobenzyloxycarbonyl, 3,4,5-trimethoxybenzyloxycarbonyl, methoxycarbonyl, ethoxycarbonyl, propoxycarbonyl, butoxycarbonyl, tert.-butoxycarbonyl, 2-bromoethoxycarbonyl, 2-chloroethoxycarbonyl, 2,2,2-trichloroethoxycarbonyl, allyloxycarbonyl, phenoxycarbonyl, 4-nitrophenoxycarbonyl, fluorenyl-9-methoxycarbonyl, acetyl, pivaloyl, isovaleroyl, phthalyl, 2,2,2-trichloroacetyl, 2,2,2-trifluoroacetyl, benzyl, tosyl, benzoyl, 4-nitrobenzoyl and phthalimido B, E, G, J, L and M each independently is a direct bond, or sarcosyl (Sar), glycyl (Gly), alanyl (Ala), arginyl (Arg), histidyl (His), leucyl (Leu), isoleucyl (Ile), seryl (Ser), threonyl (Thr), tryptophyl (Trp), tyrosyl (Tyr), valyl (Val), lysyl (Lys), ornithyl (Orn), phenylalanyl (Phe), cystyl (Cys), asparagyl (Asp), asparaginyl (Asn), glutamyl (Glu), glutaminyl (Gln), phenylglycyl (Phg), 4-nitrophenylalanyl [Phe(4NO₂)], 3-nitrophenylalanyl [Phe(3NO₂)], 2-nitrophenylalanyl, [Phe(2NO₂)], 2-, 3- or 4-aminophenylalanyl [Phe(2NH₂), Phe(3NH₂), Phe(4NH₂)], 3,4-dichlorophenylalanyl [Phe(3,4-Cl₂)], 4-iodophenylalanyl [Phe(4I)], 4-methoxyphenylalanyl [Phe(4OCH₃)], 1-triazolylalanyl [Trz(1)], 2-pyridylalanyl [Pyr(2)], 3-pyridylalanyl [Pyr(3)], 4-pyridylalanyl [Pyr(4)], 1-naphthylalanyl [Nal(1)] or 2-naphthylalanyl [Nal(2)], optionally with protective groups, D is a direct bond, or D- or L-prolyl (Pro), R¹ represents a phenyl radical which is substituted in the 2-, 3- or 4-position, a nitro group or an amino group of the formula

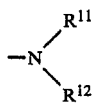

wherein

R¹¹ and R¹² each independently is hydrogen, methyl, ethyl or acetyl, or

R¹¹ is hydrogen and

R¹² is an amino-protective group, or represents 2-methyl-3-nitrophenyl, 4-methyl-3-nitrophenyl, 6-methyl-2-nitrophenyl, 3-methyl-4-nitrophenyl or 3,5-dinitrophenyl, and Q is a radical of the formula —OR¹³, —NH—NHR³, NHR¹⁴ or

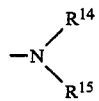

wherein

R³ is hydrogen, tert-butoxycarbonyl or benzyloxycarbonyl,

R¹³ is hydrogen, benzyl or $C_1$-$C_4$-alkyl,

R¹⁴ is hydrogen, $C_1$-$C_4$-alkyl, benzyl, 1-phenylethyl, 2-phenylethyl, adamantyl, quinuclidyl, pyridylmethyl or 4-benzylcyclohexylmethyl and R¹⁵ is $C_1$-$C_4$-alkyl, or R¹⁴ and R¹⁵ together form 4-benzylpiperidino, N-benzyl- or N-phenethylpiperazine or N-dimethylaminoethylpiperazine.

4. A compound or salt according to claim 1 of the formula

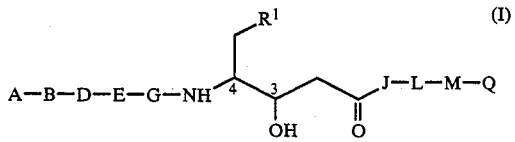

in which

A is hydrogen, tert-butoxycarbonyl, benzyloxycarbonyl, ethoxycarbonyl, acetyl, chloroacetyl, isovaleroyl, benzoyl, tosyl, phenoxycarbonyl, phthaloyl or phthalimido, B is a direct bond or phenylalanyl (Phe), D is a direct bond or prolyl (Pro), E is a direct bond, tyrosyl (Tyr), phenylalanyl (Phe), 1-naphthylalanyl [Nal(1)], 4-nitrophenylalanyl [Phe(4NO₂)], 3,4-dichlorophenylalanyl [Phe(3,4-Cl₂)], 4-aminophenylalanyl [Phe(4NH₂)], 4-iodophenylalanyl [Phe(4I)], 4-methoxyphenylalanyl [Phe(4OCH₃)] or phenylglycyl (Phg), G is a direct bond, phenylalanyl (Phe), histidyl (His), 3-pyridylalanyl [Pyr(3)] or 4-aminophenylalanyl [Phe(4NH₂)], wherein the amino group is unprotected or protected by benzyloxycarbonyl (Z), tert-butyloxycarbonyl (Boc) or fluorenyl-9-methoxycarbonyl (Fmoc), or is 1-triazolylalanyl [Trz(1)], R¹ is 2-, 3- or 4-nitrophenyl or 2-, 3- or 4-aminophenyl, J is a direct bond, leucyl (Leu) or isoleucyl (Ile), L is a direct bond, phenylalanyl (Phe), histidyl (His) or 4-nitrophenylalanyl [Phe(4NO₂)], M is a direct bond and Q is hydroxyl, methoxy, ethoxy, n-propoxy, isopropoxy, tert.-butoxy or benzyloxy, or is amino, benzylamino, 1-phenylethylamino, 2-phenylethylamino, α-pyridylmethylamino, β-pyridylmethylamino, γ-pyridylmethylamino, 4-benzylpiperazino, N-dimethylaminoethylpiperazino, 1-adamantylamino, 2-adamantylamino or 3-quinuclidineamino.

5. A compound according to claim 1, wherein such compound is N-tert.-butoxycarbonyl-L-phenylalanyl-L-histidyl-4S-amino-3S-hydroxy-5-(4-nitrophenyl)pentanoyl-L-isoleucine methyl ester of the formula

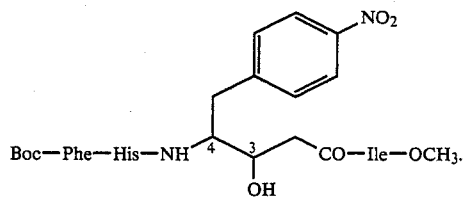

6. A compound according to claim 1, wherein such compound is N-tert.-butoxycarbonyl-L-phenylalanyl-L-histidiyl-4S-amino-3S-hydroxy-5-(2-nitrophenyl)pentanoyl-L-isoleucine methyl ester of the formula

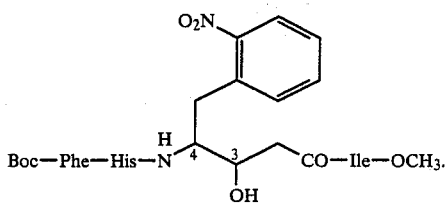

7. A compound according to claim 1, wherein such compound is N-tert.-butoxycarbonyl-L-phenylalanyl-L-histidyl-4S-amino-3RS-hydroxy-5-(3-nitrophenyl)-pentanoyl-L-isoleucine methyl ester of the formula

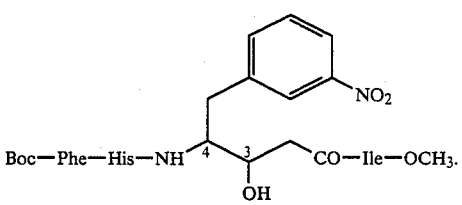

8. A compound according to claim 1, wherein such compound is N-p-tolylsulphonyl-L-phenylalanyl-L-histidyl-4S-amino-3S-hydroxy-5-(4-nitrophenyl)pentanoyl-L-isoleucine-methyl ester of the formula

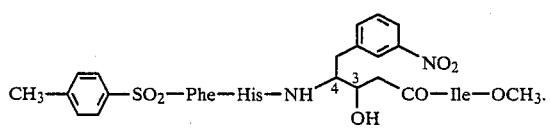

9. A compound according to claim 1, wherein such compound is N-tert.-butoxycarbonyl-L-(3,4-dichlorophenyl)alanyl-L-histidyl-4S-amino-3S-hydroxy-5-(4-nitrophenyl)pentanoyl-L-isoleucine-methyl ester of the formula

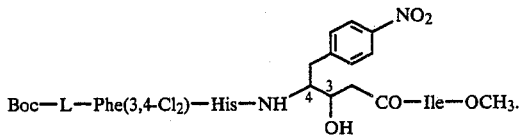

10. An antihypertensive composition comprising an amount effective therefor of a compound or salt according to claim 1 and a diluent.

11. A method of reducing blood pressure which comprises administering to a patient in need thereof an amount effective therefor of a compound or salt according to claim 1.

12. The method according to claim 11, wherein such compound is
N-tert.-butoxycarbonyl-L-phenylalanyl-L-histidyl-4S-amino-3S-hydroxy-5-(4-nitrophenyl)pentanoyl-L-isoleucine methyl ester,
N-tert.-butoxycarbonyl-L-phenylalanyl-L-histidyl-4S-amino-3RS-hydroxy-5-(2-nitrophenyl)pentanoyl-L-isoleucine methyl ester,
N-tert.-butoxycarbonyl-L-phenylalanyl-L-histidyl-4S-amino-3RS-hydroxy-5-(3-nitrophenyl)pentanoyl-L-isoleucine methyl ester,
N-p-tolylsulphonyl-L-phenylalanyl-L-histidyl-4S-amino-3S-hydroxy-5-(4-nitrophenyl)pentanoyl-L-isoleucine-methyl ester or
N-tert.-butoxycarbonyl-L-(3,4-dichlorophenyl) alanyl-L-histidyl-4S-amino-3S-hydroxy-5-(4-nitrophenyl)pentanoyl-L-isoleucine-methyl ester.

13. A compound or salt according to claim 1, wherein the group

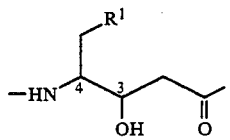

is in the 3S, 4S-configuration.

14. A compound or salt according to claim 1, wherein the group

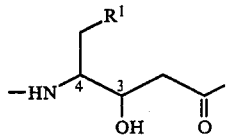

is a 3RS-4S-isomer mixture.

* * * * *

UNITED STATES PATENT AND TRADEMARK OFFICE
CERTIFICATE OF CORRECTION

PATENT NO. : 4,818,748

DATED : April 4, 1989

INVENTOR(S) : Wolfgang Bender, et al

Page 1 of 3

It is certified that error appears in the above-identified patent and that said Letters Patent is hereby corrected as shown below:

| | |
|---|---|
| Title Page, Abstract, lines 5-6 | Correct spelling of --alkyl-sulphonyl-- |
| Col. 2, line 17 | Delete "amino-protecting" and substitute --amino-protective-- |
| Col. 30, line 21 | Delete "carbonyl" and substitute --carboxyl-- |
| Col. 30, lines 58-59 | Correct spelling of --dimethylsulphoxide-- |
| Col. 32, line 60 | Delete "fracions" and substitute --fractions-- |
| Col. 32, line 61 | Correct spelling of --dimethylformamide-- |
| Col. 34, last line | Delete "LiAlH" and substitute --$LiAlH_4$-- |
| Col. 35, line 46 | Before "described" insert --is-- |
| Col. 36, line 31 | Delete "resin" and substitute --renin-- |
| Col. 37, lines 3-4 | Correct spelling of --Arzneimittelforschung-- |
| Col. 37, line 29 | Delete "cna" and substitute --can-- |
| Col. 41, line 2 | Delete "toary" and substitute --rotary-- |
| Col. 41, line 41 | Delete "7.23" substitute --7.3-- |
| Col. 44, line 1 | After "EXAMPLE NO. 8" insert --:-- |
| Col. 44, line 3 | Before "3.19" delete ";b" |
| Col. 45, line 19 | Before "482" delete "m/x" and substitute --m/z-- |

UNITED STATES PATENT AND TRADEMARK OFFICE
CERTIFICATE OF CORRECTION

PATENT NO. : 4,818,748

DATED : April 4, 1989

INVENTOR(S) : Wolfgang Bender, et al

It is certified that error appears in the above-identified patent and that said Letters Patent is hereby corrected as shown below:

| | |
|---|---|
| Col. 45, line 65 | Before "M+Na)" insert --504-- |
| Col. 48, line 65 | Delete "N9" and substitute --N-9-- |
| Col. 48, line 67 | Delete "nitrophenylpentanoyl" and substitute --nitrophenyl)pentanoyl- |
| Col. 51, line 66 | Delete "4-S" and substitute --4S-- |
| Col. 53, line 16 | Delete "(1972)" and substitute --(1972))-- |
| Col. 56, line 31 | Delete "dired" and substitute --dried-- |
| Col. 59, line 27 | Delete "(1958)" and substitute --(1958))-- |
| Col. 65, line 33 | After "pentanoic" insert --acid-- |
| Col. 67, line 34 | Correct spelling of --isoleucine-- |
| Col. 69, line 37 | Delete "$CH_2CL_2$" and substitute --$CH_2Cl_2$-- |
| Col. 71, line 68 | Delete "$F_f$" and substitute --$R_f$-- |
| Col. 72, line 31 | Delete "(110 mil%) and substitute --(110 mol%)-- |
| Col. 73, line 33 | Delete "916" and substitute --816-- |
| Col. 73, line 55 | Correct spelling of --butoxycarbonyl- |
| Col. 79, line 66 | Before "FAB-MS:" delete "(30)" and substitute --(+)-- |
| Col. 80, line 68 | Delete "system I" and substitute --system II-- |
| Col. 82, line 16 | Delete "hydroxy-5-" second instance |
| Col. 87, line 20 | After "product]" delete "," and substitute --.-- |

UNITED STATES PATENT AND TRADEMARK OFFICE
CERTIFICATE OF CORRECTION

PATENT NO. : 4,818,748

DATED : April 4, 1989

INVENTOR(S) : Wolfgang Bender, et al

It is certified that error appears in the above-identified patent and that said Letters Patent is hereby corrected as shown below:

| | |
|---|---|
| Col. 89, line 20 | Correct spelling of --butoxycarbonyl-- |
| Col. 90, line 33 | Delete "3-S" and substitute --3S-- |
| Col. 91, line 25 | Delete "either" and substitute --eight-- |

Signed and Sealed this

Twenty-ninth Day of May, 1990

Attest:

HARRY F. MANBECK, JR.

*Attesting Officer*  *Commissioner of Patents and Trademarks*